United States Patent
Amin et al.

(10) Patent No.: US 10,160,688 B2
(45) Date of Patent: Dec. 25, 2018

(54) FRACTURE-RESISTANT LAYERED-SUBSTRATES AND ARTICLES INCLUDING THE SAME

(71) Applicant: CORNING INCORPORATED, Corning, NY (US)

(72) Inventors: Jaymin Amin, Corning, NY (US); Alexandre Michel Mayolet, Corning, NY (US); Charles Andrew Paulson, Painted Post, NY (US); James Joseph Price, Corning, NY (US); Kevin Barry Reiman, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 598 days.

(21) Appl. No.: 14/482,250

(22) Filed: Sep. 10, 2014

(65) Prior Publication Data

US 2015/0079398 A1 Mar. 19, 2015

Related U.S. Application Data

(60) Provisional application No. 61/877,371, filed on Sep. 13, 2013.

(51) Int. Cl.
*B32B 15/04* (2006.01)
*B32B 17/06* (2006.01)
(Continued)

(52) U.S. Cl.
CPC ........ *C03C 17/3435* (2013.01); *C01B 21/068* (2013.01); *C01B 21/072* (2013.01);
(Continued)

(58) Field of Classification Search
USPC ....... 428/426, 428, 432, 433, 434, 688, 689, 428/697, 698, 699, 701, 702, 409, 410
See application file for complete search history.

(56) References Cited

U.S. PATENT DOCUMENTS

| 4,310,595 A | 1/1982 | Beall et al. ............... 428/332 |
| 4,995,684 A | 2/1991 | Tustison et al. ............ 350/1.6 |

(Continued)

FOREIGN PATENT DOCUMENTS

| CA | 2141536 C | 2/1994 | ............. B32B 17/06 |
| CN | 101356455 A | 1/2009 | ............... G02B 5/28 |

(Continued)

OTHER PUBLICATIONS

CN102942308 English machine translation.*
(Continued)

*Primary Examiner* — Lauren R Colgan
(74) *Attorney, Agent, or Firm* — Payal A. Patel; Jeffrey A. Schmidt

(57) ABSTRACT

Embodiments of a layered-substrate comprising a substrate and a layer disposed thereon, wherein the layered-substrate is able to withstand fracture when assembled with a device that is dropped from a height of at least 100 cm onto a drop surface, are disclosed. The layered-substrate may exhibit a hardness of at least about 10 GPa or at least about 20 GPa. The substrate may include an amorphous substrate or a crystalline substrate. Examples of amorphous substrates include glass, which is optionally chemically strengthened. Examples of crystalline substrates include single crystal substrates (e.g. sapphire) and glass ceramics. Articles and/or devices including such layered-substrate and methods for making such devices are also disclosed.

20 Claims, 21 Drawing Sheets

(51) Int. Cl.

| | |
|---|---|
| C03C 17/34 | (2006.01) |
| C01B 21/068 | (2006.01) |
| C01B 21/072 | (2006.01) |
| C01B 21/082 | (2006.01) |
| C03C 17/22 | (2006.01) |
| C03C 21/00 | (2006.01) |
| C03C 3/091 | (2006.01) |
| G01N 3/42 | (2006.01) |
| H04M 1/18 | (2006.01) |

(52) U.S. Cl.
CPC ...... *C01B 21/0823* (2013.01); *C01B 21/0825* (2013.01); *C03C 3/091* (2013.01); *C03C 17/22* (2013.01); *C03C 17/225* (2013.01); *C03C 21/002* (2013.01); *C03C 2217/28* (2013.01); *C03C 2217/281* (2013.01); *C03C 2217/78* (2013.01); *G01N 3/42* (2013.01); *G01N 2203/0098* (2013.01); *H04M 1/185* (2013.01); *Y10T 428/30* (2015.01)

(56) References Cited

U.S. PATENT DOCUMENTS

| | | | |
|---|---|---|---|
| 5,178,911 A | 1/1993 | Gordon et al. | 427/255 |
| 5,393,574 A | 2/1995 | Sulzback | 427/530 |
| 5,643,638 A | 7/1997 | Otto et al. | 427/569 |
| 5,773,148 A | 6/1998 | Charrue et al. | 428/410 |
| 6,114,043 A | 9/2000 | Joret | 428/428 |
| 6,238,781 B1 | 5/2001 | Anderson et al. | 428/216 |
| 6,344,288 B1 | 2/2002 | Oyama et al. | 428/701 |
| 6,355,334 B1 | 3/2002 | Rondeau et al. | 428/212 |
| 6,495,251 B1 | 12/2002 | Arbab et al. | 428/336 |
| 6,570,709 B2 | 5/2003 | Katayama et al. | 359/586 |
| 6,572,990 B1 | 6/2003 | Oyama et al. | 428/698 |
| 6,746,775 B1 | 6/2004 | Boire et al. | 428/432 |
| 6,838,179 B1 | 1/2005 | Legrand | 428/410 |
| 6,875,468 B2 | 4/2005 | Kunz et al. | 427/255.28 |
| 7,018,727 B2 | 3/2006 | Dzick | 428/699 |
| 7,055,954 B2 | 6/2006 | Marechal | 351/159 |
| 7,541,102 B2 | 6/2009 | Klippe et al. | 428/701 |
| 7,910,215 B2 | 3/2011 | Reymond et al. | 428/428 |
| 8,062,749 B2 | 11/2011 | Shelestak et al. | 428/410 |
| 8,118,896 B2 | 2/2012 | Can et al. | 51/295 |
| 8,187,671 B2 | 5/2012 | Sol | 427/165 |
| 8,304,078 B2 | 11/2012 | Varshneya | 428/410 |
| 8,383,214 B2 | 2/2013 | Schaepkens et al. | 428/34.7 |
| 8,409,716 B2 | 4/2013 | Schultz et al. | 428/428 |
| 8,434,951 B2 | 5/2013 | Wittenberg et al. | 396/448 |
| 8,561,429 B2 | 10/2013 | Allan et al. | |
| 8,679,631 B2 | 3/2014 | Murata | 428/410 |
| 2001/0016262 A1 | 8/2001 | Toyoshima et al. | 428/428 |
| 2002/0017452 A1 | 2/2002 | Zimmermann et al. | 204/192.1 |
| 2002/0032073 A1 | 3/2002 | Rogers et al. | 473/324 |
| 2002/0136908 A1 | 9/2002 | Komatsu et al. | 428/446 |
| 2003/0035044 A1 | 2/2003 | Nakayama et al. | 347/203 |
| 2004/0028906 A1 | 2/2004 | Anderson et al. | 428/408 |
| 2005/0233091 A1 | 10/2005 | Kumar et al. | 427/569 |
| 2006/0115651 A1 | 6/2006 | Merfeld et al. | 428/410 |
| 2006/0139783 A1 | 6/2006 | Decroupet | 359/883 |
| 2006/0165963 A1 | 7/2006 | Fleury et al. | 428/212 |
| 2006/0197096 A1 | 9/2006 | Kerdiles et al. | 257/79 |
| 2006/0240266 A1 | 10/2006 | Schicht et al. | 428/426 |
| 2007/0030569 A1 | 3/2007 | Lu et al. | 359/586 |
| 2009/0017314 A1 | 1/2009 | Nadaud et al. | 428/446 |
| 2009/0155490 A1 | 6/2009 | Bicker et al. | 427/576 |
| 2009/0202808 A1* | 8/2009 | Glaesemann | C03C 3/091 428/220 |
| 2009/0298669 A1 | 12/2009 | Akiba et al. | 501/70 |
| 2009/0324844 A1 | 12/2009 | Haoto et al. | 427/527 |
| 2010/0009154 A1 | 1/2010 | Allan et al. | 428/220 |
| 2010/0028607 A1 | 2/2010 | Lee et al. | |
| 2010/0047521 A1 | 2/2010 | Amin et al. | 428/141 |
| 2010/0196685 A1* | 8/2010 | Murata | C03C 17/3435 428/216 |
| 2010/0215950 A1 | 8/2010 | Schultz et al. | 428/336 |
| 2010/0291353 A1 | 11/2010 | Dejneka et al. | 428/192 |
| 2010/0304090 A1 | 12/2010 | Henn et al. | 428/172 |
| 2011/0129648 A1 | 6/2011 | Gu | 428/157 |
| 2012/0135153 A1 | 5/2012 | Osakabe et al. | 427/399 |
| 2012/0135852 A1 | 5/2012 | Ellison et al. | 501/66 |
| 2012/0164454 A1* | 6/2012 | Sung | C23C 16/26 428/408 |
| 2012/0171497 A1* | 7/2012 | Koyama | C03C 3/085 428/428 |
| 2012/0212826 A1 | 8/2012 | Henn et al. | 359/586 |
| 2012/0219792 A1 | 8/2012 | Yamamoto et al. | 428/336 |
| 2012/0251743 A1 | 10/2012 | Amin et al. | 428/34.4 |
| 2012/0321898 A1 | 12/2012 | Meinhardt et al. | 428/410 |
| 2012/0327568 A1 | 12/2012 | Shedletsky et al. | 361/679.01 |
| 2013/0022798 A1 | 1/2013 | Fukawa et al. | 428/212 |
| 2013/0127202 A1 | 5/2013 | Hart | 296/146.1 |
| 2013/0169950 A1 | 7/2013 | Wickboldt et al. | G06F 3/045 |
| 2013/0209762 A1 | 8/2013 | Damm et al. | 428/212 |
| 2014/0106146 A1 | 1/2014 | Zeng et al. | |
| 2014/0106141 A1 | 4/2014 | Bellman et al. | |
| 2014/0106150 A1 | 4/2014 | Decker et al. | |
| 2014/0193606 A1* | 7/2014 | Kwong | C30B 29/20 428/138 |

FOREIGN PATENT DOCUMENTS

| | | | |
|---|---|---|---|
| CN | 102807330 A | 12/2012 | |
| CN | 102942308 | * 2/2013 | |
| EP | 1407714 | 7/1973 | G01N 3/42 |
| EP | 0566271 A2 | 10/1993 | C03C 17/22 |
| EP | 592986 B1 | 8/1998 | B32B 15/04 |
| EP | 1289898 B1 | 8/2012 | C03C 17/22 |
| EP | 1490715 B1 | 2/2013 | G02B 5/08 |
| GB | 1407714 A | 9/1975 | |
| JP | 63238260 A | 10/1988 | C23C 14/06 |
| JP | 1998231147 A | 9/1998 | |
| JP | 02974879 B2 | 11/1999 | C23C 16/06 |
| JP | 2000113510 | 4/2000 | G11B 7/254 |
| JP | 2000171601 A | 6/2000 | C03C 17/34 |
| JP | 2000171605 A | 6/2000 | H04N 5/65 |
| JP | 2001303246 A | 10/2001 | C03C 17/22 |
| JP | 2002174810 A | 6/2002 | G02F 1/1333 |
| JP | 2003131011 A | 5/2003 | G02F 1/1335 |
| JP | 2005274527 | 10/2005 | G04B 39/00 |
| JP | 2007099557 A | 4/2007 | C03C 21/00 |
| JP | 04250834 B2 | 4/2009 | C23C 14/34 |
| JP | 2009116218 A | 5/2009 | G02B 1/11 |
| JP | 2009265601 A | 11/2009 | G02B 6/40 |
| JP | 2010202514 A | 9/2010 | C03C 3/083 |
| JP | 2011057547 A | 3/2011 | C03C 3/083 |
| JP | 2011093728 A | 5/2011 | C03B 23/203 |
| JP | 04707656 B2 | 6/2011 | G02B 1/11 |
| JP | 2011133800 A | 7/2011 | G09F 9/00 |
| JP | 04765069 B2 | 9/2011 | C23C 24/08 |
| JP | 04790396 B2 | 10/2011 | G02B 1/11 |
| JP | 2012064765 A | 3/2012 | |
| JP | 5110723 B1 | 12/2012 | |
| JP | 2013015872 A | 1/2013 | G02F 1/1333 |
| JP | 2016517381 A | 6/2016 | |
| KR | 1103041 B1 | 1/2012 | G02B 1/11 |
| WO | 1998037254 A2 | 8/1998 | C23C 14/00 |
| WO | 2006099765 A1 | 9/2006 | C03C 17/00 |
| WO | 2013/088856 A1 | 6/2013 | G09F 9/00 |
| WO | 2013/160233 | 10/2013 | G02B 1/10 |
| WO | WO2014055491 A1 | 4/2014 | B32B 17/10 |
| WO | WO2014124206 A1 | 8/2014 | C09D 5/00 |

OTHER PUBLICATIONS

Oliver, W.C.; Pharr, G. M. An improved technique for determining hardness and elastic modulus using load and displacement sensing indentation experiments. J. Mater. Res., vol. 7, No. 6, 1992, 1564-1583.

(56) References Cited

OTHER PUBLICATIONS

Oliver, W.C.; Pharr, G.M. Measurement of Hardness and Elastic Modulus by Instrument Indentation: Advances in Understanding and Refinements to Methodology. J. Mater. Res., vol. 19, No. 1, Mar. 20, 2004.
XP002405973, Advanced Materials and Processes Technology, Transparent Armor, vol. 4, No. 4, 2000.
Jonghoon Back, James Ma, Michael F. Becker, John W.Keto, Desiderio Kovar. "Correlations between optical properties, microstructure, and processing conditions of Aluminum nitride thin films fabricated by pulsed laser deposition." Elsevier, Thin Solid Films 515 (2007) 7096-7104.
B. Bitterlich, K. Friederich. "Particle-reinforced SiAlONs for Cutting Tools." Materials Science Forum vol. 554 (2007) pp. 129-134.
R. Boichot, N. Coudurier, F. Mercier, S. Lay, A. Crisci, S. Coindeau, A. Claudel, E. Blanquet, M. Pons. "Epitaxial growth of AlN on c-plane sapphire by High Temperature Hydride Vapor Phase Epitaxy: Incluence of the gas phase N/Al ratio and low temperature protective layer." Elsevier, Surface & Coatings Technology 237 (2013) 118-125.
D. Chen, X.L. Ma, Y.M. Wang. "Thickness-dependent structural transformation in the AlN film." Elsevier, Acta Materialia 53 (2005) 5223-5227.
Cinzia Caliendo and Patrizia Imperatori. "Structural, optical, and acoustic characterization of high-quality AlN thick films sputtered on Al2O3 (001) at temperature for GHz-band electroacoustic devices applications." Journal of Applied Physics 96, No. 5, 2610 (2004).
K. Ait Aissa, A. Achour, J. Camus, L. Le Brizoual, P.-Y. Jouan, M.-A. Djouadi. "Comparison of the structural properties and residual stress of AlN films deposited by dc magnetron sputtering and high power impulse magnetron sputtering at different working pressures." Elsevier, Thin Solid Films, 550 (2014) 264-267.
T. Easwarakhanthan, S.S. Hussain, and P. Pigeat. "Spectroellipsometric investigation of optical, morphological, and structural properties of reactively sputtered polycrystalline AlN films." J. Vac. Sci. Technology A 28 (3), pp. 495-501, May/Jun. 2010.
J. Gazda, J. Zhao, P.Smith, and R.A. White. "Formation of ALN films on Ti/TiN Arc-Layer Interface with Al-0.5% Cu Interconects evaluated by XPS and Energy-filtered-TEM." Mat. Res. Soc. Symp. Proc. vol. 589, 365-370, 2001.
Fatemeh Hajakbari, Majid Mojtahedzadeh Larijani, Mahmood Ghoranneviss, Morteza Aslaninejad, and alireza Hojabri. "Optical Properties of Amorphous AlN Thin Films on Glass and Silicon Substrates Grown by Single Ion Beam Sputtering." Jpn. J. Appl. Phys. 49, 095802 (2010).
VN Inkin, GG Kirpilenko, AJ Kolpakov. "Properties of aluminium nitride coating obtained by vacuum arc discharge method with plasma flow separation." Elsevier, Diamond and Related Materials, 10 (2001) 1314-1316.
Takashi Ishiguro, Masato Nishimura and Takashi Yamazaki. "Solar Light Absorption Property of Sputtered Al—N Films with Enhanced Surface Roughness during Film Growth." Jpn. J. Appl. Phys. vol. 41 (2002) pp. 292-300.
XS Miao and YC Chan. "Optical Properties and Reactive Sputtering Conditions of AlN and AlSiN Thin Films for Magneto-Optical Applications." Journal of Electronic Materials, vol. 26, No. 1, 1997.
JA Savage. "Preparation and properties of hard crystalline materials for optical applications—a review." Journal of Crystal Growth 113 (1991) 698-715.
Krupitskaya, Auner. "Optical Characatization of AlN Films Grown by Plasma Source Molecular Beam Epitaxy." Journal of Applied Physices 84, 2861-2865, 1998.
Yamashita, Michihiro; Okuda, Kazuhid; Watanabe, Yasumitsu. "Preparation and Properties of AlON—SiAlON Composites." Jpn. Kokai Tokkyo Koho, 109, 434-439, 2001.
Pantano, Carlo G. "Al2O3 Coating by Atomic Layer Deposition (ALD) on various glass substrates for Surface Strength Improvement." Published by Penn State.

Bernd Schroter, Aimo Winkelmann, Wolfgang Richter. "X-ray photoelectron diffraction on SiC and AlN epitaxial films: polytype structure and polarity." Elsevier, Journal of Electron Spectroscopy and Related Phenomena. 114-116 (2001) 443-450.
Atul Vir Singh, Sudhir Chandra, AK Srivastava, BR Chakroborty, G Sehgal, MK Dalai, G Bose. "Structural and optical properties of RF magnetron sputtered aluminium nitride films without external substrate heating." Elsevier, Applied Surface Sceince 257 (2011) 9568-9573.
Tsui, et al., "Effects of Adhesion on the Measurement of Thin Film Mechanical Properties by Nanoindentation." Mat. Res. Soc. Symp. Proc. vol. 473 1997.
X Wang, A Kolitsch, and W Moller. "Roughness Improvement and Hardness Enhancement in Nanoscale Al/AlN Multilayered Thin Films." Applied Physics Letters vol. 71, No. 14, 1951-1953, Oct. 6, 1997.
Yoshihisa Watanabe, Yuji Hara, Takeshi Tokuda, Nobuaki Kitazawa, and Yoshikazu Nakamura. "Surface Oxidation of Aluminum Nitride Thin Films." Surface Modification Technologies XIII, Edited by Sudarshan, Khor, Jeandin, ASM International, Materials Park, Ohio, 1999. pp. 209-215.
Hiroshi Yamashita and Akira Yamaguchi. "Preparation and Properties of AlON—SiAlON Composites." Journal of the Ceramic Society of Japan 109, pp. 434-439, 2001.
JS Zabinski, JJ Hu, JE Bultman, NA Pierce, AA Voevodin. "Stoichiometry and characterization of aluminium oxynitride thin films grown by ion-beam assisted pulsed laser deposition." Elsevier, Thin Solid Films, 516, pp. 6215-6219, 2008.
Shyang-ho Chi, Yen-Ling Chung. "Cracking in coating-substrate composites with multi-layered and FGM coatings." Engineering Fracture Mechanics, vol. 70, 1227-1243, 2003.
B. Reinhold, H.J. Spies. "Plasma Nitriding of Aluminum Alloys." Proceedings of the 1st Internat onal Automotive Heat Treating Conference. Jul. 13-15, 1998.
Wang,Qimin;Wu, Yingna; Ji, Ailing; Ke, Peiling; Sun, Chao; Huang, Rongfang; Wen, Lishi. "Study of ALON and CRON films deposited by arc ion plating as diffusion barriers." Jinshu Xuebao (2004), 40, 1, 83-87.
Hirai, Shinji; Miwa, Tetsuya; Iwata, Tsutomu; Ozawa, Masayoshi; Katayama, Hiroshi G. "Fomiation of Aluminum Nitride by Carbothermic Reduction of Alumina in a Flowing Nitrogen Atmosphere." Nippon Kinzoku Gakkaishi (1989, 53 (10), 1035-40.
Xi, Zhong-hong, Li, Hai-Yi. "The Preparation and Optical properties of AlN Thin Films." Diwen Wuli Xuebao (2012), 34)6), 467-470.
Urushidani, Tanio; Kasahara, Takashi. "Etalon-Type Optical Filters, Their Modules, Spectrometers, and Optical Devices." Jpn. Kokai Tokkyo Koho, 2012.
Urushidani, Tanio; Kigahara, Koji. "Optical Filters Including Optical Films Covered with Thickness-Controlled Dielectric Films, and Optical Filter Modules, Spectrometers and Optical Apparatus Containing Them." 2012.
Yamamoto, Yuji; Hashizume, Haruo. "Manufacture of IR-Reflecting Bent Plate Glass." Jpn. Kokai Tokkyo Koho, 1988.
Xi, Zhong-hong; Li, Hai-yi. "The Preparation and Optical Properties of AlN Thin Films." Diwen Wuli Xuebao, 34, 467-470, 2012.
Wen, Mao et al. "The AlN layer thickness dependent coherent epitaxial growth, stress and hardness in NbN/AlN nanostructured multilayer films." Surface and Coatings Technology 235 (2013) 367-375.
Yan, Feng , Liu, Zhengtang, Liu, Wenting. "The Preparation and Properties of Y2O3/AlN Anti-Reflection Films on Chemical Vapor Deposition Diamond." Elsevier, Thin Solid Films, 520, pp. 734-738, 2011.
Huang, Meidong; Zhang, Linlin; Wang, Lige; Tong, Lina; Li, Xiaona; Dong, Chuang. "Effects of Substrate Temperature on Aluminum Nitride Films by Reactive Magnetron Sputtering." Xiyou Jinshu, 35 (5), pp. 715-718, 2011.
Borges, J.; Alves, E.: Vax, F.; Marques, L. "Optical Properties of AlNxOy Thin Films Deposited by DC Magnetron Sputtering." Proceedings of SPIE, 2011.

(56) References Cited

OTHER PUBLICATIONS

Yang, Shi-cai; Abduleziz, Ablat; Jian, Ji-Kang; Zheng, Yu-feng; Sun, Yan-fei; Wu, Rong. "Preparation and Properties of AlN Thin Films by Pure Nitrogen Reactive Sputtering." Rengong Jingti Xuebao, 39 (1), pp. 190-196, 2010.

Yang, Shi-cai; Abduleziz, Ablat; Jian, Ji-kang; Zheng, Yu-feng; Sun, Yan-fei; Wu, Rong. "Preparation and Properties of C-Axis Preferred Orientation AlN Thin Films by Pure Nitrogen Reactive Sputtering." Xianjiang Daxue Xuebao, Ziran Kexueban, 26 (4), pp. 444-449, 2009.

Zayats, Boiko, Gentsar, Litvin, Papusha, Sopinskii. "Optical Studies of AlN/n-Si(100) Films Obtained by the Method of High-Frequency Magnetron Sputtering."

M.B. Assouar; O. Elmazria; M El Hakiki; and P. Alnot. "Study of Acoustical and Optical Properties of AlN Films for SAW and BAW Devices: Correlation Between These Properties." Integrated Ferroelectrics, 82: 45-54, 2006.

Chen, Skromme, Chen, Sun, Yang, Khan, Nakarmi, Lin, Jiang, Reitmeyer, Davis, Dalmau, Schlesser, and Sitar. "Optical Reflectance of Bulk AlN Crystals and AlN Epitaxial Films." AIP Conference Proceedings, 772, 297-298, 2005.

Yun, F., et al.. "Optical and Structural Investigation of AlN Grown on Sapphire with Reactive MBE Using RF Nitrogen or Ammonia." Mat. Res. Soc. Symp. Proc., vol. 764, 2003.

Danylyuk, et al.. "Optical and Electrical Properties of Al 1-x InxN Films Grown on Sapphire (0001) by Plasma Source Molecular Beam Epitaxy." Mat. Res. Soc. Symp., vol. 639, 2001.

Mania, Ryszard. "Magnetron Sputtering for Deposition of Aluminum Nitride Thin Films." Prace Komisji Nauk Ceramiczynych, 54, 429-433, 1997.

English Translation of CN201480062442.7 First Office Action dated Dec. 25, 2017, China Patent Office, 10 Pgs.

English Translation of JP2016542805 Office Action dated May 15, 2018; 2 Pages; Japanese Patent Office.

* cited by examiner

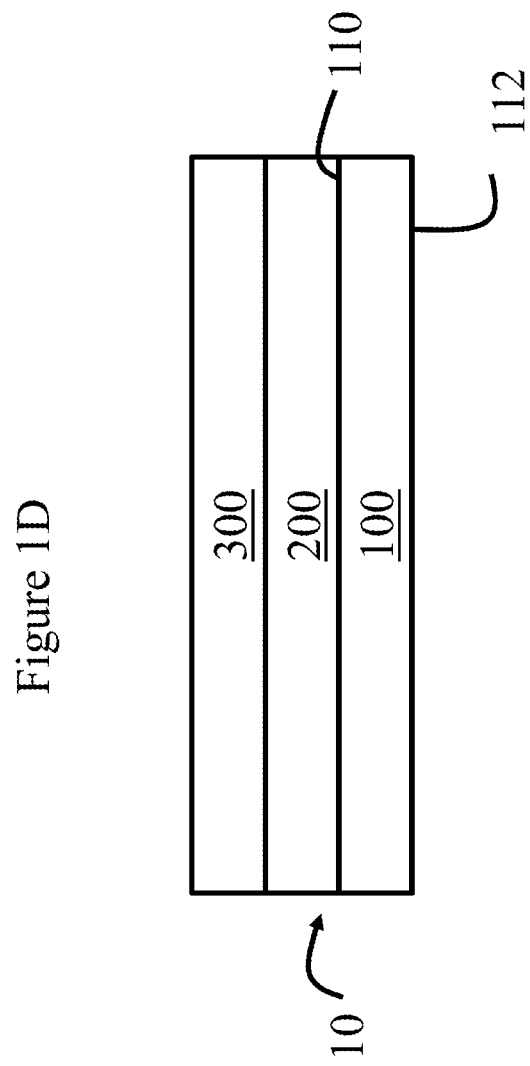

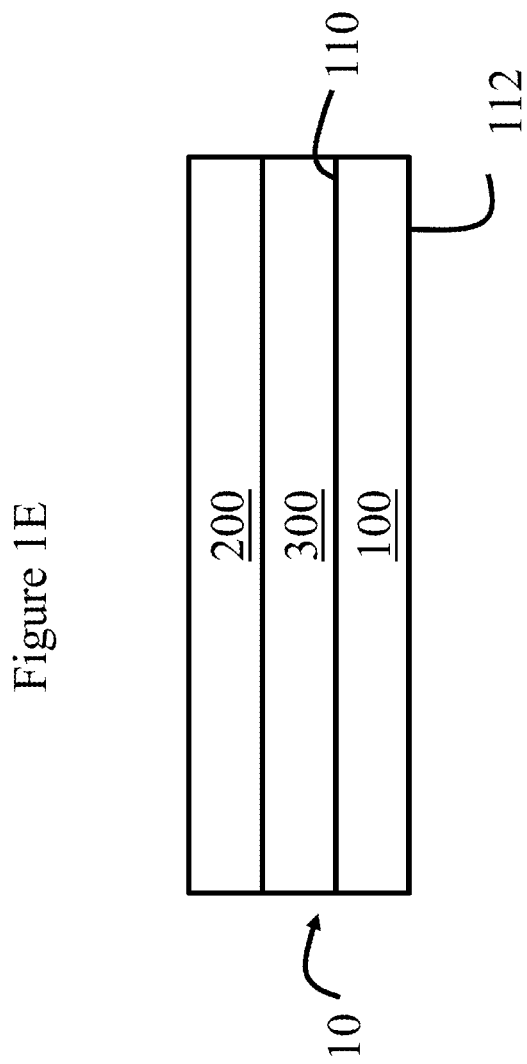

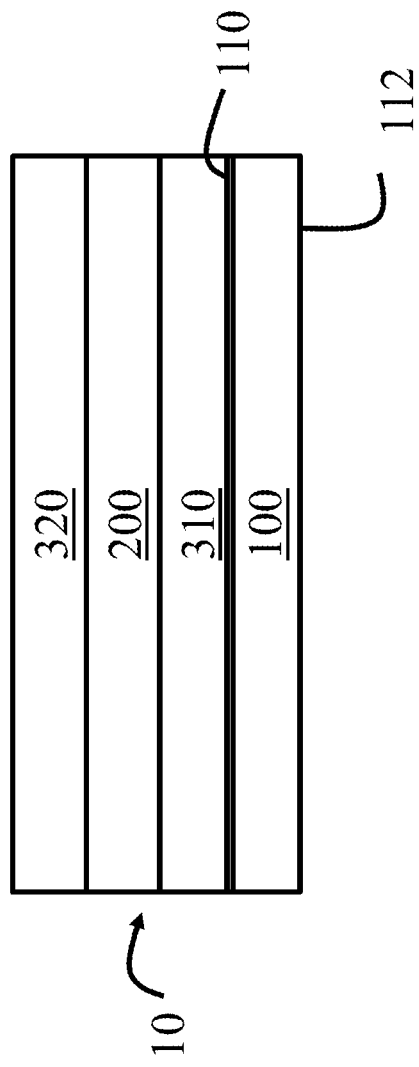

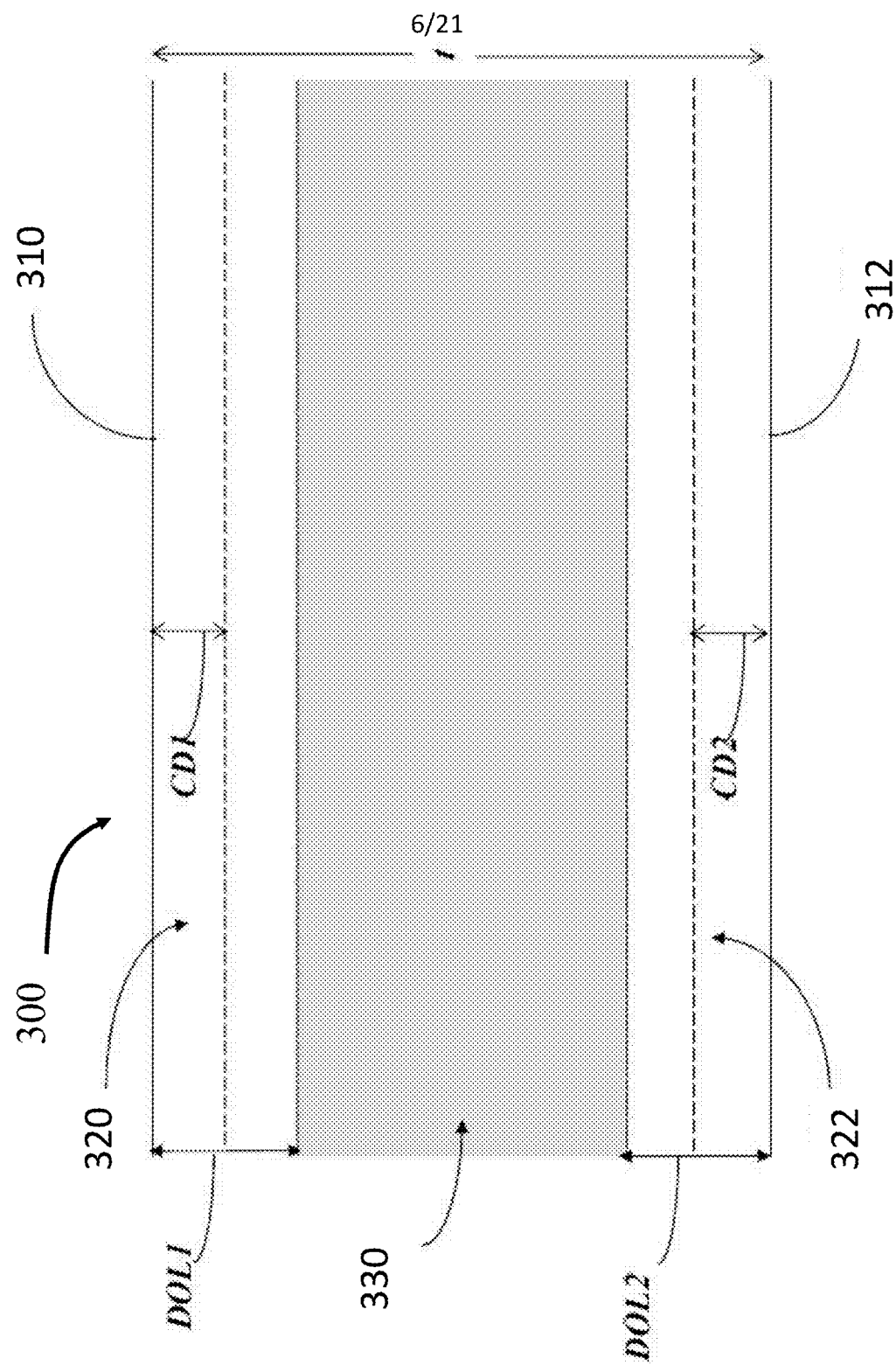

abraded ROR - SiC

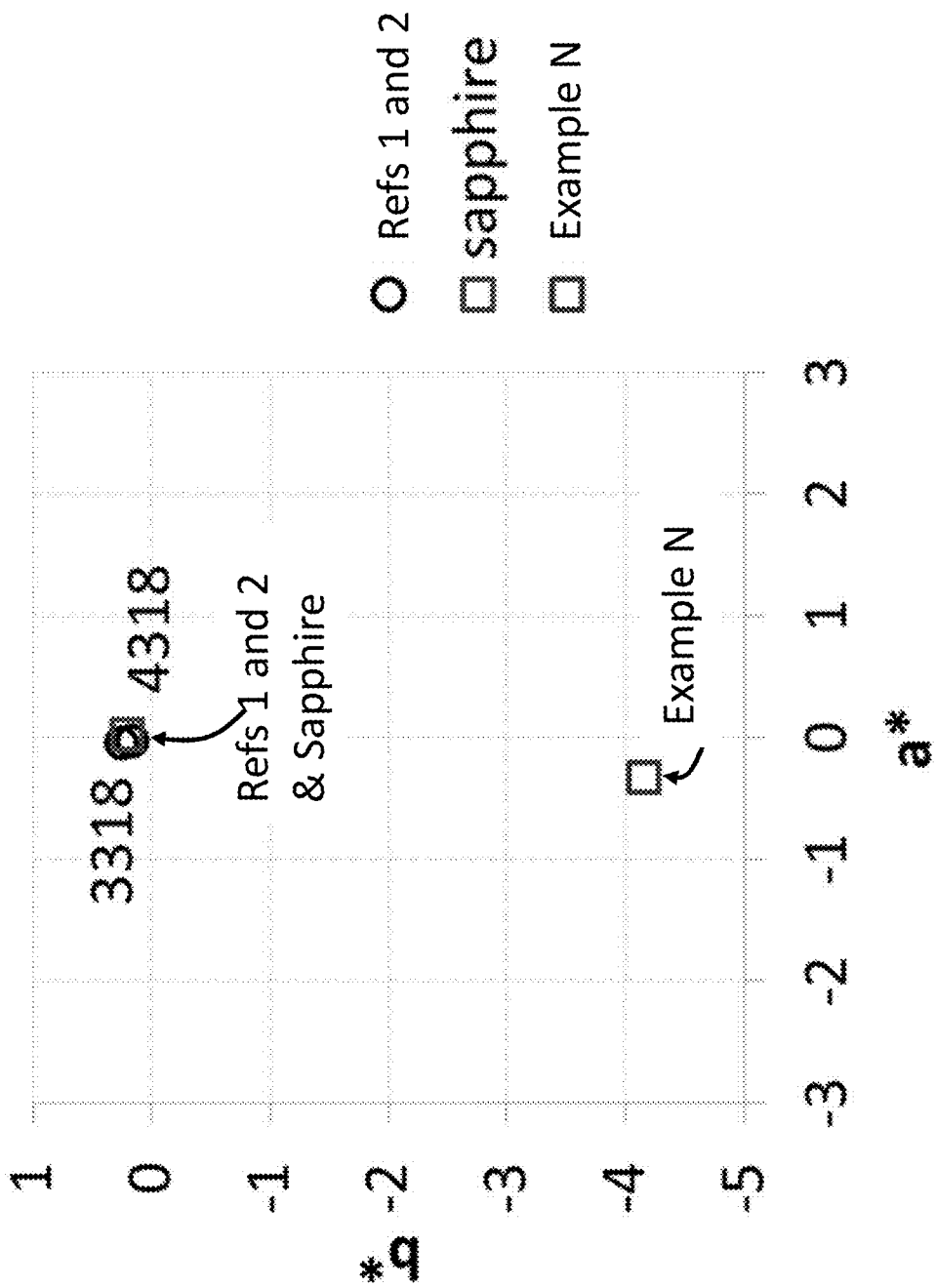

FRACTURE-RESISTANT LAYERED-SUBSTRATES AND ARTICLES INCLUDING THE SAME

CROSS-REFERENCE TO RELATED APPLICATIONS

This application claims the benefit of priority under 35 U.S.C. § 119 of U.S. Provisional Application Ser. No. 61/877,371, filed on Sep. 13, 2013, the contents of which re relied upon and incorporated herein by reference in their entirety.

BACKGROUND

This disclosure relates to fracture-resistant layered-substrates, articles and devices including such layered-substrates and methods for making such layered-substrates, articles and/or devices. More particularly, this disclosure relates to layered-substrates including a substrate and a layer that are able to withstand fracture when assembled with an article (e.g., electronic device, architectural structures, appliances, automotive components, etc.) that is dropped onto a drop surface or that exposed to other objects being dropped thereon.

Articles such as electronic devices (e.g., mobile phones, smart phones, tablets, video players, information terminal devices, laptop computer, etc.), architectural structures (e.g., countertops or walls), appliances (e.g., cooktops, refrigerator and dishwasher doors, etc.), information displays (e.g., whiteboards), and automotive components (e.g., dashboard panels, windshields, window components, etc.) incorporate various substrates as internal components or external components. When used in such articles, the substrate can be part of a housing or a display. When used in a display, the substrate may be referred to as a cover substrate and, in some instances, may form part of a touch module. Cover substrates are often transparent and scratch-resistant. Substrates used as housing can form the sides, back and front portions of housing and may exhibit scratch-resistance and opacity, instead of exhibiting transparency.

With continuing efforts to make some articles or components of articles lighter and thinner and to include even greater functionality, substrates, whether used as cover substrates or housing substrates, are becoming thinner. As substrates become thinner, they are also more susceptible the damage that can occur during normal use of articles incorporating such substrates. It has become more important to develop substrates having improved survivability, especially when subjected to tensile stresses caused by contact with hard/sharp surfaces, such as asphalt or concrete and/or falling objects, experienced in "real world" use and applications.

Moreover, there is a need for such substrates to exhibit resistance to scratches that cause abrasion damage and/or scratches that cause single event scratch damage. Single event scratch damage can be contrasted with abrasion damage. In some cases, substrates used as external components in devices, such as electronic devices, do not typically experience abrasion damage because abrasion damage is generally caused by reciprocating sliding contact from hard counter face objects (e.g., sand, gravel and sandpaper). Instead, cover substrates typically endure only reciprocating sliding contact from soft objects, such as fingers. In addition, where such substrates are combined with layers (or coatings), abrasion damage can generate heat, which can degrade chemical bonds in such layers and can cause flaking and other types of damage. As abrasion damage is often experienced over a longer term, the layer disposed on the substrate that experiences the abrasion damage can also oxidize, which further degrades the durability of the layer and thus the layered-substrate. The single events that cause scratch damage generally do not involve the same conditions as the events that cause abrasion damage and therefore, the solutions often utilized to prevent abrasion damage may not prevent single event scratch damage in substrates or layered-substrates. Moreover, known scratch and abrasion damage solutions often compromise the optical properties, which is not acceptable in most uses of substrates, layered-substrates or articles incorporating the same.

SUMMARY

One or more embodiments of this disclosure pertain to a device or article that includes a fracture resistant layered-substrate that is able to withstand fracture when the device or article is dropped from a height of at least 100 cm onto a drop surface (e.g., asphalt or 180 grit sandpaper). The layered-substrate may include a substrate having opposing major surfaces and a layer disposed on a first opposing major surface. In one or more embodiments, the layered-substrate exhibits a first average flexural strength and exhibits a second average flexural strength after abrading, wherein the second average flexural strength is at least 80% of the first average flexural strength. The layered-substrate may be substantially transparent and/or may exhibit a transmittance of at least 90%. In one or more embodiments, the layered-substrate may be substantially opaque and/or exhibit a transmittance of less than 20% or less than 10%.

In one or more embodiments, the layered-substrate may exhibit resistance to flaw penetration of one or more flaws from the layer into the substrate. The flaws may be introduced into the layer by contact between the layered-substrate and the drop surface or may be present in the layer prior to being subjected to impact tests. Impact tests include drop tests and tests in which objects are dropped onto the layered-substrate. In one or more alternative embodiments, the layer may substantially prevent the introduction of new flaws into the substrate.

In one or more embodiments, the substrate may be transparent or opaque, and may include an amorphous substrate (e.g., soda lime glass, alkali aluminosilicate glass, alkali containing borosilicate glass and/or alkali aluminoborosilicate glass), a crystalline substrate (e.g., single crystal substrates such as sapphire and/or glass-ceramic substrates) or a combination thereof. In some embodiments, the substrate exhibits a refractive index in the range from about 1.45 to about 1.55. In yet other embodiments, the substrate exhibits an average strain-to-failure at a surface of one or more of the opposing major surfaces that is 0.5% or greater. Where amorphous substrates are utilized, the substrate may be glass which is optionally strengthened or chemically strengthened. For example, some glass substrates may include a compressive stress (CS) layer extending within the chemically strengthened glass from a surface of the chemically strengthened glass to a depth of layer DOL (in μm). The CS may be at least 250 MPa and the DOL may be at least 10 μm or even ≥75 μm. In one or more specific embodiments, the ratio $CS_s$/DOL ratio may be ≤15, where $CS_s$ is the compressive stress at the surface of the substrate. In even more specific embodiments, a strengthened glass substrate may have a stress profile such that the compressive stress $CS_D$ at an intermediate critical depth of 50 μm below the surface is at least 5% of $CS_s$. In one or more alternative embodiments, the strengthened glass substrate may exhibit a spike in compressive stress at the surface $CS_s$.

In one or more embodiments, the layered—substrate includes a layer that either alone or in combination with the substrate provides scratch resistance to the substrate and can exhibit a specific hardness, as measured by a Berkovich Indenter Hardness Test (as described herein), such as, for example greater than about 8 GPa along an indentation depth of about 100 nm or greater (e.g., from about 100 nm to about 300 nm, from about 100 nm to about 400 nm, from about 100 nm to about 500 nm, or from about 100 nm to about 600 nm). In some embodiments, the hardness of the layer or the layer in combination with the substrate (i.e., the layered-substrate), as measured by the Berkovich Indenter Hardness Test, is at least about 10 GPa, at least about 15 GPa, at least about 20 GPa or at least about 23 GPa along an indentation depth of about 100 nm or greater (e.g., from about 100 nm to about 300 nm, from about 100 nm to about 400 nm, from about 100 nm to about 500 nm, or from about 100 nm to about 600 nm). The layer can include a metal oxide, a metal nitride, a metal oxynitride, a metal carbide, a metal boride, diamond-like carbon or a combination thereof. Exemplary metals include B, Al, Si, Ti, V, Cr, Y, Zr, Nb, Mo, Sn, Hf, Ta and W. The layer may be formed by atomic layer deposition, chemical vapor deposition, physical vapor deposition or thermal evaporation. In one or more embodiments, the layer may also improve the optical properties of the layered-substrate. In one example, the layer may reduce the reflectivity of the substrate.

In one or more embodiments, the layered-substrate may include one or more additional layers. The additional layer may be disposed on layer, between the layer and the substrate or both on the layer and between the layer and the substrate. In some embodiments, the one or more additional layers may manage one or more optical properties of the layered-substrate (e.g., reflectivity, transmission, reflectance, transmittance, color in reflectance and/or color in transmittance). For example, the one or more additional layers may exhibit a refractive index that is less than the refractive index of the layer. In another embodiment, the additional layer may have a thickness that also differs or is the same as the layer. The thickness and the refractive index of the one or more additional layers may modify the reflectivity, transmission, reflectance, transmittance, color in reflectance and/or color in transmittance of the layered-substrate.

In one variant, the one or more additional layers may include a metal oxide, a metal nitride, a metal oxynitride and/or a combination thereof. Exemplary metals include B, Al, Si, Ti, V, Cr, Y, Zr, Nb, Mo, Sn, Hf, Ta and W. In one or more specific embodiments, the layer may include AlOxNy and the additional layer may include $SiO_2$ or $Al_2O_3$. In another variant, the layered-substrate may include two additional layers and the first additional layer may include one of $SiO_2$ or $Al_2O_3$ and the second additional layer may include the other of $SiO_2$ or $Al_2O_3$. The first additional layer and the second additional layer may also include the same layered-substrates. The first and second additional layers may exhibit the same or different thicknesses as each other or the same or different thicknesses (each or together) as the layer.

In some embodiments, the additional layer may include a crack mitigating layer and such layer may be disposed between the layer and the substrate. Examples of crack mitigating layers are described in U.S. patent application Ser. No. 14/052,055, filed on Oct. 11, 2013, U.S. patent application Ser. No. 14/053,093, filed on Oct. 14, 2013, and U.S. patent application Ser. No. 14/053,139, filed on Oct. 14, 2013, the contents of which are incorporated herein by reference in their entirety.

Methods of a device are also provided. In one or more embodiments, the method includes providing a substrate comprising opposing major surfaces, disposing a layer as described herein on a first opposing major to form a layered-substrate that is able to withstand fracture when assembled with the device and the device is in a drop test from a height of at least 100 cm onto a drop surface, and assembling the layered-substrate with the device.

Another aspect of the present invention pertains to a portable device including a substrate providing a user interface and having an initial scratch resistance and an initial impact resistance and a layer disposed thereon to form a layered-substrate that exhibits an enhanced scratch resistance and enhanced impact resistance. In one or more embodiments, the enhanced impact resistance includes an average flexural strength after abrading the layered-substrate that is at least 80% of the average flexural strength of the layered-substrate before the layered-substrate is abraded. The enhanced scratch resistance can include a hardness, as measured by the Berkovich Indenter Hardness Test, of at least about 20 GPa along an indentation depth of about 100 nm or greater.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiment(s), and together with the description serve to explain principles and operation of the various embodiments.

BRIEF DESCRIPTION OF THE DRAWINGS

FIG. 1D is a side view illustration of a layered-substrate according to one or more embodiments.

FIG. 1E is a side view illustration of a layered-substrate according to one or more embodiments.

FIG. 1F is a side view illustration of a layered-substrate according to one or more embodiments.

FIG. 2 is an illustration of a substrate according to one or more embodiments.

FIG. 15A is a plot of the transmittance color coordinates a* and b* in the L*a*b* color space of select substrates and Example N, according to Example 6.

DETAILED DESCRIPTION

Figure 1:
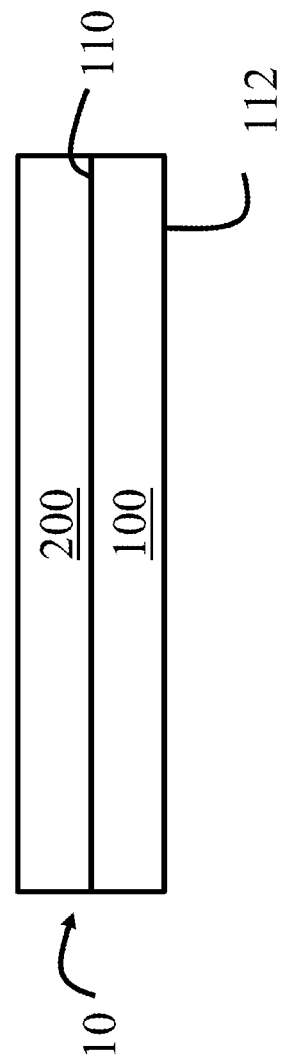
FIG. 1 is a side view illustration of a layered-substrate according to one or more embodiments.

Reference will now be made in detail to the embodiment(s), examples of which are illustrated in the accompanying drawings. Whenever possible, the same reference numerals will be used throughout the drawings to refer to the same or like parts.

A first aspect of this disclosure pertains to layered-substrates with improved survivability. As used herein, "survivability" refers to the ability of the layered-substrates to resist or withstand fracture during drop tests, or after an object is dropped on the layered-substrate, as described herein. As shown in FIG. 1, a layered-substrate 10 can include a substrate 100, which may be described as a cover substrate or housing substrate depending on its use in an article and/or device, and a layer 200 disposed thereon. The substrate 100 includes opposing major surfaces 110, 112 and opposing minor surfaces (not shown). The layer 200 is shown in FIG. 1 as being disposed on a first opposing major surface 110; however, the layer 200 may be disposed on the second opposing major surface 112 and/or one or both of the opposing minor surfaces, in addition to or instead of being disposed on the first opposing major surface 110.

In one embodiment, the layered-substrate can include the substrate 100 and the layer 200, different layers bonded to each other (including the layer 200, other layered-substrate layers and/or thin film layers), the substrate and a discontinuous layer 200, as described herein, and/or the layer 200 and discontinuous other layers.

The term "layer" may include a single layer or may include one or more sub-layers. Such sub-layers may be in direct contact with one another. The sub-layers may be formed from the same material or more than one different material. In one or more alternative embodiments, such sub-layers may have intervening layers of different materials disposed therebetween. In one or more embodiments a layer may include one or more contiguous and uninterrupted layers and/or one or more discontinuous and interrupted layers (i.e., a layer having different materials formed adjacent to one another). A layer or sub-layers may be formed by any known method in the art, including discrete deposition or continuous deposition processes. In one or more embodiments, the layer may be formed using only continuous deposition processes, or, alternatively, only discrete deposition processes.

As used herein, the term "dispose" includes coating, depositing and/or forming a material onto a surface using any known method in the art. The disposed material may constitute a layer, as defined herein. The phrase "disposed on" includes the instance of forming a material onto a surface such that the material is in direct contact with the surface and also includes the instance where the material is formed on a surface, with one or more intervening material(s) is between the disposed material and the surface. The intervening material(s) may constitute a layer, as defined herein.

Figure 1B:
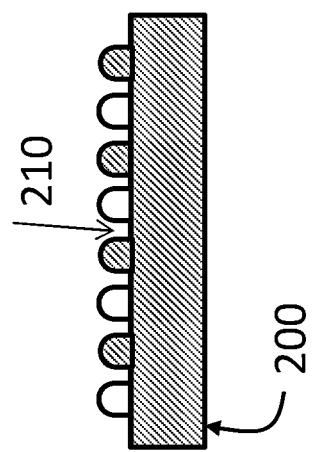
FIG. 1B is a cross-sectional view illustration of the layer shown in FIG. 1A taken along lines 1B-1B.
Figure 1C:
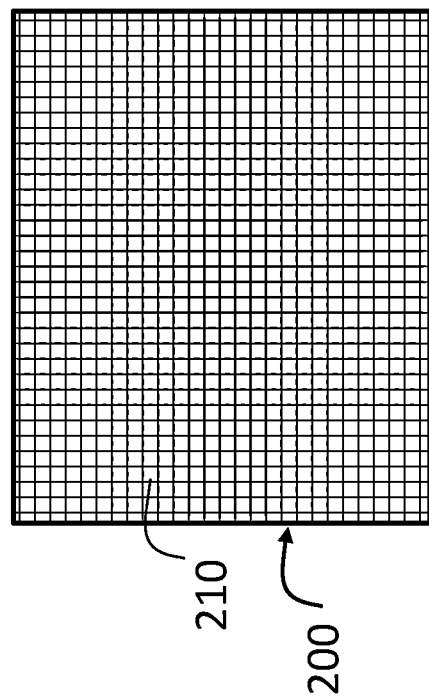
FIG. 1C is a top view illustration of a layer according to one or more embodiments.
Figure 1A:
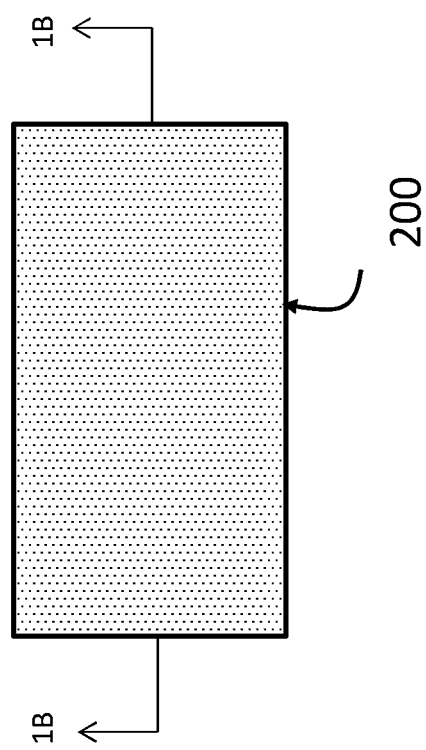
FIG. 1A is a top view illustration of a layer according to one or more embodiments.

With respect to "discontinuous layers", such layers may include layer(s) that do not cover the entire surface of the substrate 100 or include area(s) where the substrate 100 that are not covered by the layer(s). For example, as shown in FIGS. 1A and 1B, the layer 200 may be disposed as discrete islands of material on the substrate 100 that may be unconnected to one another, leaving uncovered space 210 on the substrate 100 between the islands of the layer 200. Alternatively, as shown in FIG. 1C, the layer 200 may be disposed in discrete lines across the surface of the substrate 100 such that there is uncovered space 210 between the lines of layer 200. In some instances, the discrete lines of the layer 200 may intersect such that the layer 200 forms a cohesive layer on the substrate 100 despite the presence of uncovered space 210 between the lines.

Substrate

As otherwise described herein, the substrate 100 may be used in articles and/or devices as a housing substrates or as a cover substrate (e.g., in a display). When used in a display, the substrate 100 may form part of a touch module. Substrates 100 used as housing substrates in articles and/or devices may form at least a portion of the sides, back and/or front surface of the housing.

The substrate 100 may include an amorphous substrate, a crystalline substrate or a combination thereof. The substrate 100 may be formed from man-made materials and/or naturally occurring materials. In some specific embodiments, the substrate 100 may specifically exclude plastic and/or metal substrates. In one or more embodiments, the substrate exhibits a refractive index in the range from about 1.45 to about 1.55. In specific embodiments, the substrate 100 may exhibit an average strain-to-failure at a surface on one or more opposing major surface that is 0.5% or greater, 0.6% or greater, 0.7% or greater, 0.8% or greater, 0.9% or greater, 1% or greater, 1.1% or greater, 1.2% or greater, 1.3% or greater, 1.4% or greater 1.5% or greater or even 2% or greater, as measured using ball-on-ring testing using at least 5, at least 10, at least 15, at least 20 samples. In specific embodiments, the substrate 100 may exhibit an average strain-to-failure at its surface on one or more opposing major surface of about 1.2%, about 1.4%, about 1.6%, about 1.8%, about 2.2%, about 2.4%, about 2.6%, about 2.8%, or about 3% or greater.

In one or more embodiments, the amorphous substrate may include glass, which may be strengthened or non-strengthened. Examples of suitable glass include soda lime glass, alkali aluminosilicate glass, alkali containing borosilicate glass and alkali aluminoborosilicate glass. In some variants, the glass may be free of lithia. In one or more alternative embodiments, the substrate 100 may include crystalline substrates such as glass ceramic substrates (which may be strengthened or non-strengthened) or may include a single crystal structure, such as sapphire. In one or more specific embodiments, the substrate 100 includes an amorphous base (e.g., glass) and a crystalline cladding (e.g., sapphire layer, a polycrystalline alumina layer and/or or a spinel ($MgAl_2O_4$) layer).

The substrate 100 may be substantially planar or sheet-like, although other embodiments may utilize a curved or otherwise shaped or sculpted substrate. The substrate 100 may be substantially optically clear, transparent and free from light scattering. In such embodiments, the substrate may exhibit an average transmittance over the visible spectrum (e.g., 380 nm-780 nm) of about 85% or greater, about 86% or greater, about 87% or greater, about 88% or greater, about 89% or greater, about 90% or greater, about 91% or greater or about 92% or greater. In one or more alternative embodiments, the substrate 100 may be opaque or exhibit an average transmittance over the visible spectrum (e.g., 380 nm-780 nm) of less than about 10%, less than about 9%, less than about 8%, less than about 7%, less than about 6%, less than about 5%, less than about 4%, less than about 3%, less than about 2%, less than about 1%, or less than about 0%. In substrate 100 may optionally exhibit a color, such as white, black, red, blue, green, yellow, orange etc. As used herein, the term "light transmission" refers to the amount of light that is transmitted through a medium. The measure of light transmission is the difference between the amount of light that enters the medium and the amount of light that exits the medium (that is not reflected or absorbed by the medium). The term "average light transmission" refers to spectral average of the light transmission multiplied by the luminous efficiency function, as described by CIE standard observer. As used herein, the term "transmittance" is defined as the percentage of incident optical power within a given wavelength range transmitted through a material (e.g., the article, the inorganic oxide substrate or the layered substrate or portions thereof). The term "reflectance" is similarly defined as the percentage of incident optical power within a given wavelength range that is reflected from a material (e.g., the article, the inorganic oxide substrate or the layered substrate or portions thereof). Transmittance and reflectance are measured using a specific linewidth. In one or more embodiments, the spectral resolution of the characterization of the transmittance and reflectance is less than 5 nm or 0.02 eV.

Additionally or alternatively, the thickness of the substrate 100 may vary along one or more of its dimensions for aesthetic and/or functional reasons. For example, the edges of the substrate 100 may be thicker as compared to more central regions of the substrate 100. The length, width and thickness dimensions of the substrate 100 may also vary according to the layered-substrate 10 application or use.

The substrate 100 may be provided using a variety of different processes. For instance, where the substrate 100 includes an amorphous substrate such as glass, various forming methods can include float glass processes and down-draw processes such as fusion draw and slot draw.

A glass substrate prepared by a float glass process may be characterized by smooth surfaces and uniform thickness is made by floating molten glass on a bed of molten metal, typically tin. In an example process, molten glass that is fed onto the surface of the molten tin bed forms a floating glass ribbon. As the glass ribbon flows along the tin bath, the temperature is gradually decreased until the glass ribbon solidifies into a solid glass substrate that can be lifted from the tin onto rollers. Once off the bath, the glass substrate can be cooled further and annealed to reduce internal stress.

Down-draw processes produce glass substrates having a uniform thickness that possess relatively pristine surfaces. Because the average flexural strength of the glass substrate is controlled by the amount and size of surface flaws, a relatively pristine surface that has had minimal contact has a higher initial strength. When this high strength glass substrate is then further strengthened (e.g., chemically), the resultant strength can be higher than that of a glass substrate with a surface that has been lapped and polished. Down-drawn glass substrates may be drawn to a thickness of less than about 2 mm. In addition, down drawn glass substrates have a very flat, smooth surface that can be used in its final application without costly grinding and polishing.

The fusion draw process, for example, uses a drawing tank that has a channel for accepting molten glass raw material. The channel has weirs that are open at the top along the length of the channel on both sides of the channel. When the channel fills with molten material, the molten glass overflows the weirs. Due to gravity, the molten glass flows down the outside surfaces of the drawing tank as two flowing glass films. These outside surfaces of the drawing tank extend down and inwardly so that they join at an edge below the drawing tank. The two flowing glass films join at this edge to fuse and form a single flowing glass substrate. The fusion draw method offers the advantage that, because the two glass films flowing over the channel fuse together, neither of the outside surfaces of the resulting glass substrate comes in contact with any part of the apparatus. Thus, the surface properties of the fusion drawn glass substrate are not affected by such contact.

The slot draw process is distinct from the fusion draw method. In slot draw processes, the molten raw material glass is provided to a drawing tank. The bottom of the drawing tank has an open slot with a nozzle that extends the length of the slot. The molten glass flows through the slot/nozzle and is drawn downward as a continuous substrate and into an annealing region.

Once formed, a glass substrate may be strengthened to form a strengthened glass substrate. As used herein, the term "strengthened glass substrate" may refer to a glass substrate that has been chemically strengthened, for example through ion-exchange of larger ions for smaller ions in the surface of the glass substrate. However, other strengthening methods known in the art, such as thermal tempering, or utilizing a mismatch of the coefficient of thermal expansion between portions of the substrate to create compressive stress and central tension regions, may be utilized to form strengthened glass substrates.

The glass substrates may be chemically strengthened by an ion exchange process. In this process, ions in the surface layer of the glass substrate are replaced by—or exchanged with—larger ions having the same valence or oxidation state. In those embodiments in which the glass substrate comprises an alkali aluminosilicate glass, ions in the surface layer of the glass and the larger ions are monovalent alkali metal cations, such as $Li^+$ (when present in the glass), $Na^+$, $K^+$, $Rb^+$ and $Cs^+$. Alternatively, monovalent cations in the surface layer may be replaced with monovalent cations other than alkali metal cations, such as $Ag^+$ or the like.

Ion exchange processes are typically carried out by immersing a glass substrate in a molten salt bath containing the larger ions to be exchanged with the smaller ions in the glass substrate. It will be appreciated by those skilled in the art that parameters for the ion exchange process, including, but not limited to, bath composition and temperature, immersion time, the number of immersions of the glass in a salt bath (or baths), use of multiple salt baths, additional steps such as annealing, washing, and the like, are generally determined by the composition of the glass substrate and the desired depth of compression layer and compressive stress of the glass substrate that result from the strengthening operation. By way of example, ion exchange of alkali metal-containing glass substrates may be achieved by immersion in at least one molten bath containing a salt such as, but not limited to, nitrates, sulfates, and chlorides of the larger alkali metal ion. The temperature of the molten salt bath typically is in a range from about 380° C. up to about 450° C., while immersion times range from about 15 minutes up to about 40 hours. However, temperatures and immersion times different from those described above may also be used.

In addition, non-limiting examples of ion exchange processes in which glass substrates are immersed in multiple ion exchange baths, with washing and/or annealing steps between immersions, are described in U.S. patent application Ser. No. 12/500,650, filed Jul. 10, 2009, by Douglas C. Allan et al., entitled "Glass with Compressive Surface for Consumer Applications" and claiming priority from U.S. Provisional Patent Application No. 61/079,995, filed Jul. 11, 2008, in which glass substrates are strengthened by immersion in multiple, successive, ion exchange treatments in salt baths of different concentrations; and U.S. Pat. No. 8,312,739, by Christopher M. Lee et al., issued on Nov. 20, 2012, and entitled "Dual Stage Ion Exchange for Chemical Strengthening of Glass," and claiming priority from U.S. Provisional Patent Application No. 61/084,398, filed Jul. 29, 2008, in which glass substrates are strengthened by ion exchange in a first bath is diluted with an effluent ion, followed by immersion in a second bath having a smaller concentration of the effluent ion than the first bath. The contents of U.S. patent application Ser. No. 12/500,650 and U.S. Pat. No. 8,312,739 are incorporated herein by reference in their entirety.

The degree of chemical strengthening achieved by ion exchange may be quantified based on the parameters of central tension (CT), compressive stress (CS), depth of layer (DOL) and depth of compression layer (DOC). Compressive stress, DOL and DOC are measured using those means known in the art. Such means include, but are not limited to, measurement of surface stress (FSM) using commercially available instruments such as the FSM-6000, manufactured by Luceo Co., Ltd. (Tokyo, Japan), or the like, and methods of measuring compressive stress and depth of layer are described in ASTM 1422C-99, entitled "Standard Specification for Chemically Strengthened Flat Glass," and ASTM 1279.19779 "Standard Test Method for Non-Destructive Photoelastic Measurement of Edge and Surface Stresses in Annealed, Heat-Strengthened, and Fully-Tempered Flat Glass," the contents of which are incorporated herein by reference in their entirety. Surface stress measurements rely upon the accurate measurement of the stress optical coefficient (SOC), which is related to the birefringence of the glass substrate. SOC in turn is measured by those methods that are known in the art, such as fiber and four point bend methods, both of which are described in ASTM standard C770-98 (2008), entitled "Standard Test Method for Measurement of Glass Stress-Optical Coefficient," the contents of which are incorporated herein by reference in their entirety, and a bulk cylinder method.

CS may be measured near the surface or within the strengthened glass at various depths. A maximum compressive stress value may include the measured compressive stress at the surface ($CS_s$) of the strengthened glass substrate. The thickness of the compressive stress layer characterized as DOL, may be determined by surface stress meter (FSM) measurements using commercially available instruments such as the FSM-6000. The compressive stress may also be characterized in terms of DOC, which refers to the depth at which the stress within the glass changes from compressive to tensile stress. At the DOC, the stress crosses from a positive (compressive) stress to a negative (tensile) stress and thus has a value of zero. In some instances, the CT, which is computed for the inner region adjacent the compressive stress layer within a glass substrate, can be calculated from the compressive stress CS, the thickness t, and the DOL. The relationship between CS and central tension CT is given by the expression (1):

$$CT=(CS \cdot DOL)/(t-2DOL) \qquad (1),$$

wherein t is the thickness, expressed in microns (μm), of the glass article. In various sections of the disclosure, central tension CT and compressive stress CS are expressed herein in megaPascals (MPa), thickness t is expressed in either microns (μm) or millimeters (mm) and depth of layer DOL is expressed in microns (μm). Where DOC is utilized, it may also be expressed in microns (μm).

In one embodiment, a strengthened glass substrate 100 can have a surface compressive stress of 250 MPa or greater, 300 MPa or greater, e.g., 400 MPa or greater, 450 MPa or greater, 500 MPa or greater, 550 MPa or greater, 600 MPa or greater, 650 MPa or greater, 700 MPa or greater, 750 MPa or greater or 800 MPa or greater. The strengthened glass substrate may have a compressive depth of layer of 10 μm or greater, 15 μm or greater, 20 μm or greater (e.g., 25 μm, 30 μm, 35 μm, 40 μm, 45 μm, 50 μm or greater) and/or a central tension of 10 MPa or greater, 20 MPa or greater, 30 MPa or greater, 40 MPa or greater (e.g., 42 MPa, 45 MPa, or 50 MPa or greater) but less than 100 MPa (e.g., 95, 90, 85, 80, 75, 70, 65, 60, 55 MPa or less). In one or more specific embodiments, the strengthened glass substrate has one or more of the following: a surface compressive stress greater than 500 MPa, a depth of compressive layer greater than 15 μm, and a central tension greater than 18 MPa.

A cross-sectional schematic view of one or more particular embodiments of a strengthened glass substrate is shown in FIG. 2. The strengthened glass substrate 300 has a thickness t, first surface 310, and second surface 312. The strengthened glass substrate 300 has a first compressive layer 320 extending from first surface 310 to a depth of layer $DOC_1$ into the bulk of the glass substrate 300. In the embodiment shown in FIG. 2, the strengthened glass substrate 300 also has a second compressive layer 322 extending from second surface 312 to a second depth of layer $DOL_2$. The strengthened glass substrate 300 also has a central region 330 between compressive layers 320 and 322. Central region 330 is under a tensile stress or central tension (CT), which balances or counteracts the compressive stresses of layers 320 and 322, respectively.

In the embodiment shown in FIG. 2, the strengthened glass substrate 300 includes intermediate critical depths $CD_1$ and $CD_2$ within compressive stress layers 320 and 322. Without being bound by theory, these intermediate critical depths $CD_1$ and $CD_2$ and the compressive stresses at these critical depths may be sufficient to increase survivability of the strengthened glass substrate 300, with or without the layer 200 (not shown).

In one or more embodiments, the strengthened glass substrate 300 may include a surface CS ($CS_s$) and a DOL of greater than or equal to 75 μm, wherein the ratio $CS_s$/DOL≤15, or even ≤12. In some instances, the ratio $CS_s$/DOL may be in the range from about 0.1 to about 12. In a specific embodiment, the strengthened glass substrate 300 may include a stress profile such that compressive stress $CS_D$ at an intermediate critical depth of 50 μm below the surface is at least 5% of $CS_s$, at least 10% of $CS_s$, at least 25% of $CS_s$, or in the range from about 25% to about 75% of $CS_s$. In some embodiments, DOL may be in the range from about 80 to about 120 μm. $CS_s$ may be ≥250 MPa or in the range from about 350 MPa to about 500 MPa. In some instances, $CS_s$ may be ≥500 MPa (e.g., from about 700 to about 1200 MPa). In one or more embodiments, $CS_D$ may be in the range from about 70 MPa to about 200 MPa.

Figure 3:
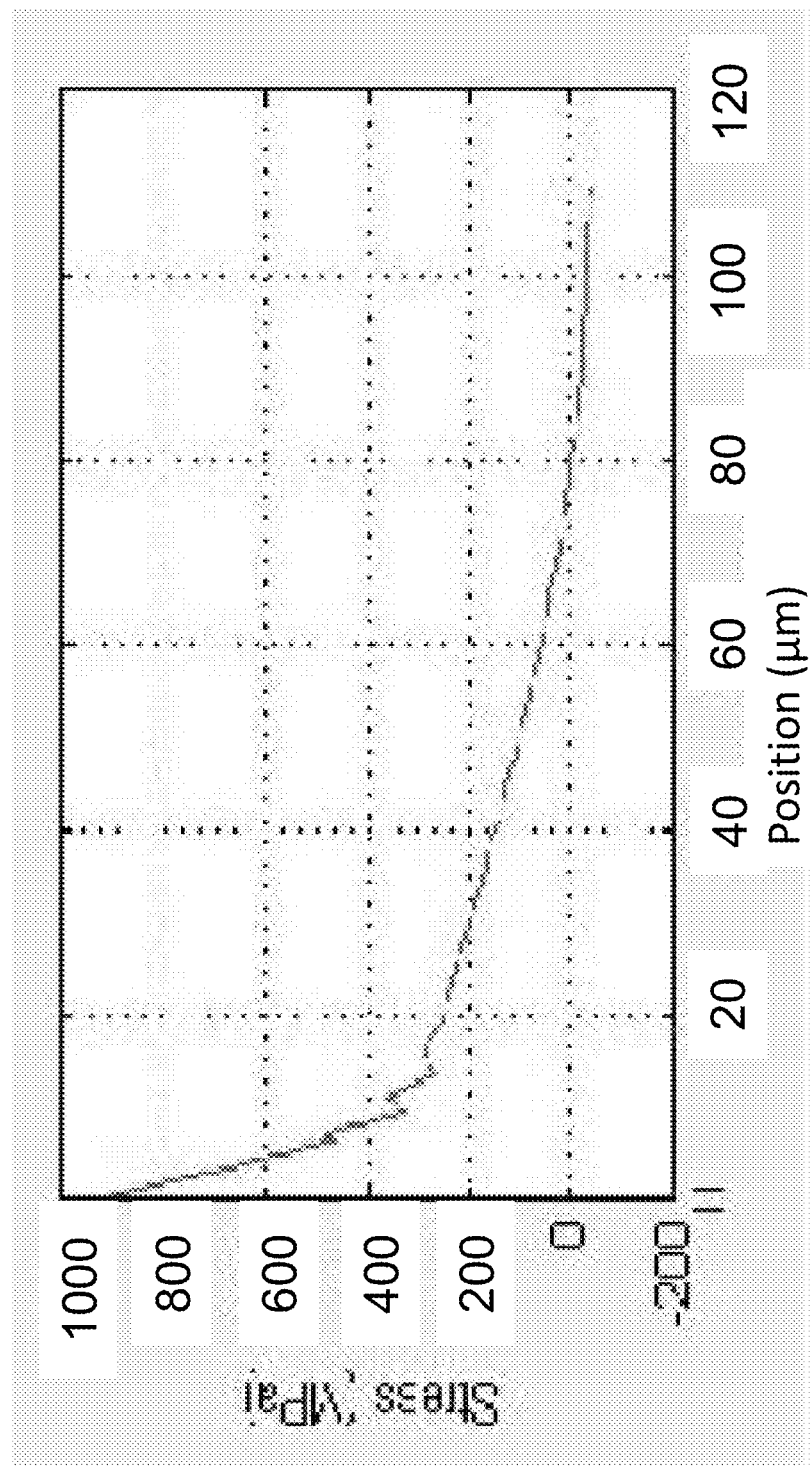
FIG. 3 is a graphical illustration of the stress profile of a 1 mm thick strengthened glass substrate having a $CS_s$ of 936 MPa and a DOL of 80 μm according to one or more embodiments.
Figure 4:
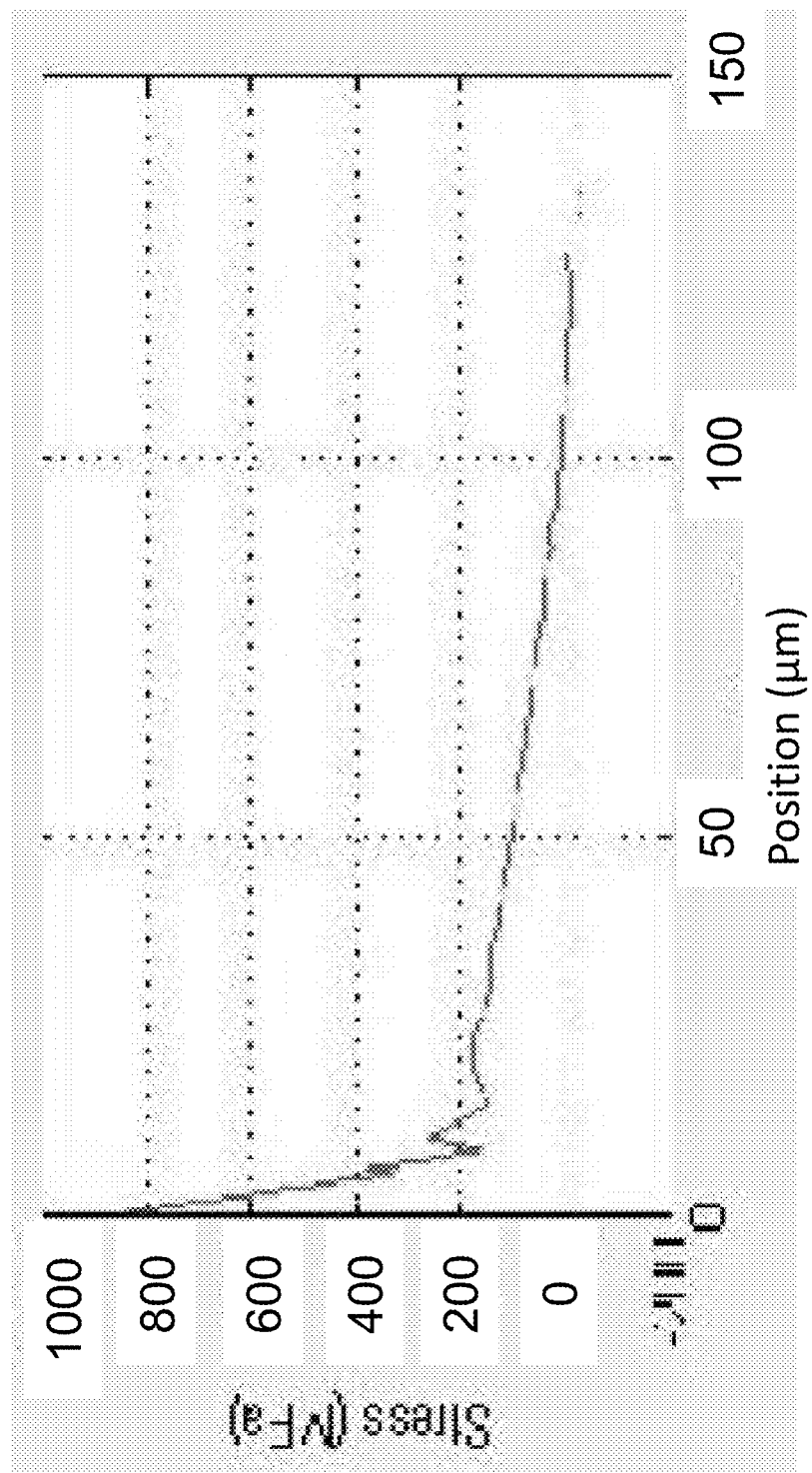
FIG. 4 is a graphical illustration of the stress profile of a 1 mm thick strengthened glass substrate having a $CS_s$ of 897 MPa and a DOL of 108 μm according to one or more embodiments.
Figure 5:
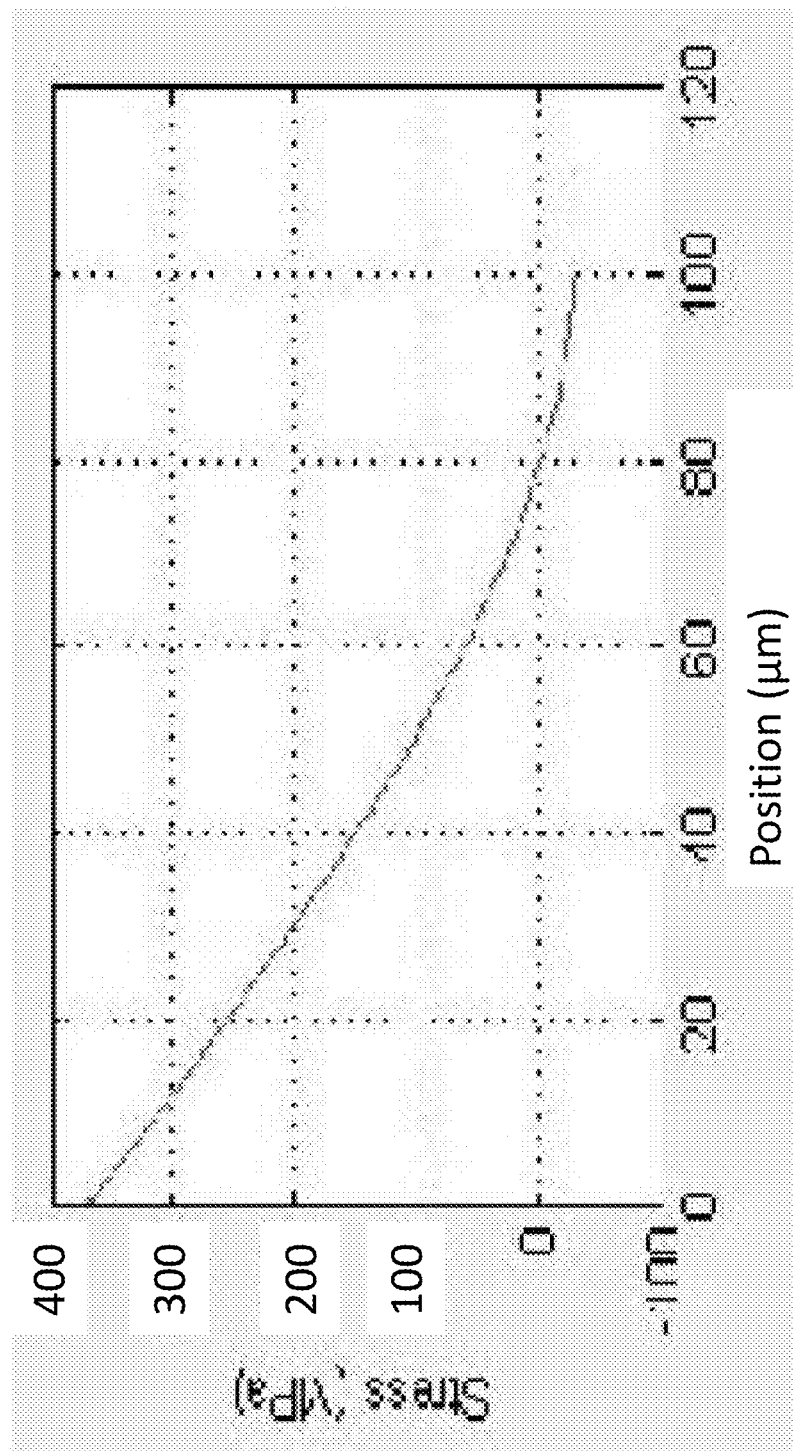
FIG. 5 is a graphical illustration of the stress profile of a 1 mm thick strengthened glass substrate having a $CS_s$ of 372 MPa and a DOL of 80 μm according to one or more embodiments.
Figure 6:
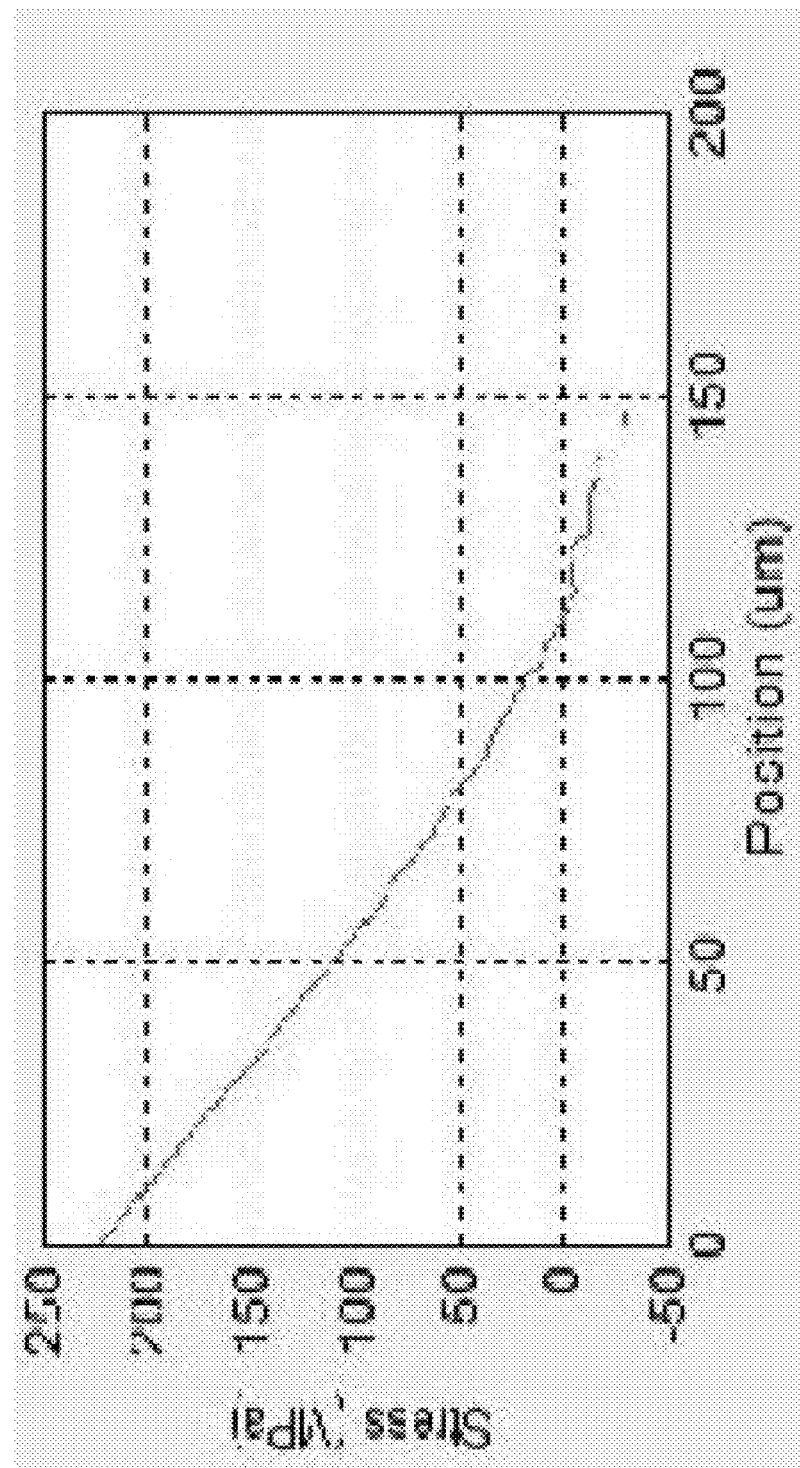
FIG. 6 is a graphical illustration of the stress profile of a 1 mm thick strengthened glass substrate having a $CS_s$ of 225 MPa and a DOL of 112 μm according to one or more embodiments.

As further illustration, FIGS. 3-6 show the stress profiles of 1 mm thick strengthened alkali aluminosilicate glass substrates having a deep DOL (i.e., DOL≥75 μm). As shown in FIG. 3, a strengthened glass substrate having a $CS_s$ of 936 MPa and a DOL of 80 μm has a spike or increase of compressive stress at the surface of the glass substrate. At an intermediate depth of 50 μm, there is a compressive stress $CS_D$ of approximately 100 MPa. Similar to the glass substrate depicted in FIG. 3, FIG. 4 depicts a strengthened glass substrate having a compressive stress spike on the surface. The strengthened glass substrate, which has a $CS_s$ of 897 MPa and a DOL of 108 μm, has a compressive stress of about 100 MPa at a depth of 50 μm. FIGS. 5 and 6 depict strengthened glass substrates which do not include compressive stress spikes at the surface. The strengthened glass substrate shown in FIG. 5 has a $CS_s$ of 372 MPa and a DOL of 80 μm, and includes a $CS_D$ of about 100 MPa at a CD of 50 μm. The strengthened glass substrate of FIG. 6 has a $CS_s$ of 225 MPa and a DOL of 112 μm, and includes a $CS_D$ of about 110 MPa at a CD of 50 μm.

In one or more embodiments, the strengthened glass substrate may have at least one deep compressive layer extending from a surface of the substrate to a DOC of at least about 45 μm within the substrate. In one embodiment, the compressive stress profile of the strengthened glass substrate includes a single linear segment extending from the surface to the depth of compression DOC. Alternatively, the compressive stress profile of the strengthened glass substrate includes two approximately linear portions: the first portion extending from the surface to a relatively shallow depth and having a steep slope; and a second portion extending from the shallow depth to the depth of compression. In the embodiments, the strengthened glass substrates described herein have a maximum compressive stress $CS_s$ of at least about 150 MPa. In some embodiments, the maximum compressive stress $CS_s$ is at least about 210 MPa and, in other embodiments, at least about 300 MPa. In some embodiments, the maximum compressive stress $CS_s$ is located at the surface (310, 312 in FIG. 2). In other embodiments, however, the maximum compressive $CS_s$ may be located in the compressive region (320, 322) at some depth below the surface of the strengthened glass substrate. The compressive region extends from the surface of the strengthened glass substrates to a depth of compression DOC of at least about 45 microns (μm). In some embodiments, DOC is at least about 60 μm. In other embodiments, DOC is at least about 70 μm, in some embodiments, at least about 80 μm, and, in still other embodiments, DOC is at least about 90 μm. In certain embodiments, the depth of compression DOC is at least 100 μm and, in some embodiments at least about 140 μm. In certain embodiments, the depth of compression has a maximum value of about 100 μm.

Figure 7:
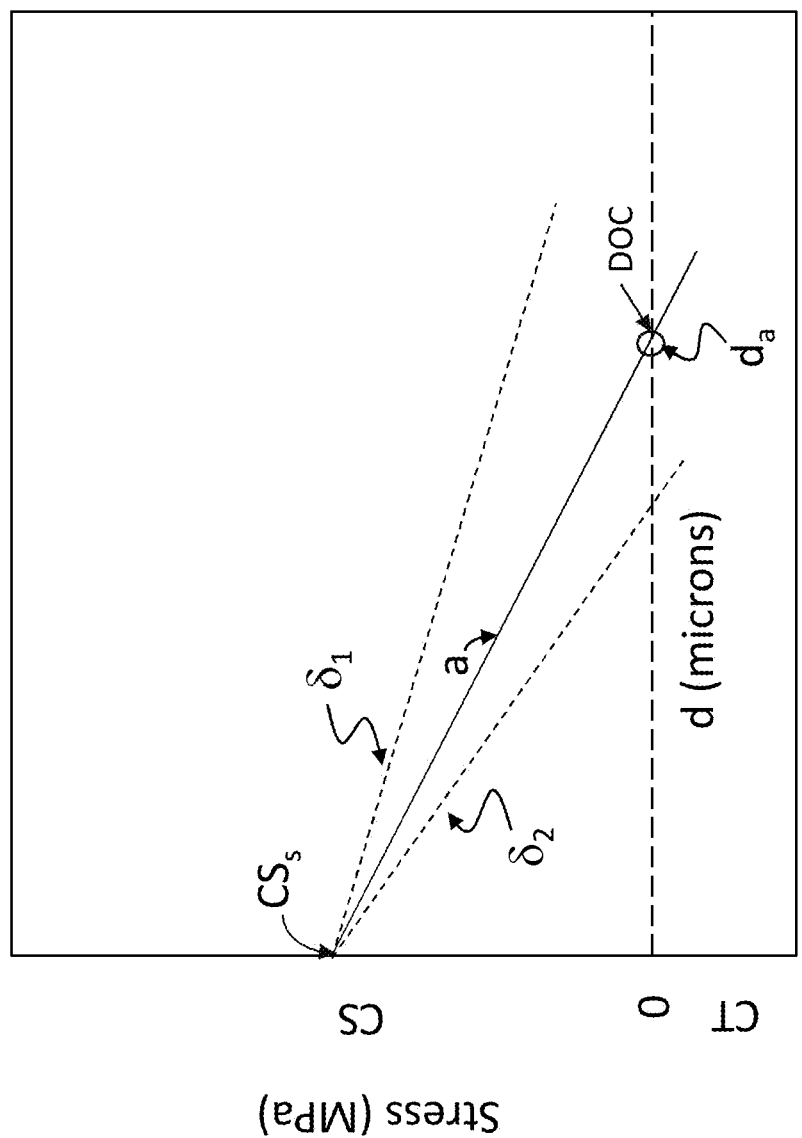
FIG. 7 is a schematic representation of a compressive stress profile of a substrate according to one or more embodiments.

The compressive stress varies as a function of depth below the surface of the strengthened glass substrate, producing a compressive stress profile in the compressive region (330, in FIG. 2). The strengthened glass substrate may exhibit a specific compressive stress, as described in U.S. Patent Application No. 62/014,464, entitled "Strengthened Glass with Deep Depth of Compression", and filed on Jun. 19, 2014, which is incorporated herein by reference. In some embodiments, the compressive stress profile is substantially linear within the compression region, as schematically shown in FIG. 7. In FIG. 7, the compressive stress behaves substantially linearly, resulting in a straight line a having a slope $m_a$, expressed in MPa/μm, that intercepts the vertical y (CS) axis at $CS_s$. CS profile a intercepts the x axis at the depth of compression DOC. At this point, the total stress is zero. Below DOC, the glass article is in tension CT, reaching a central value CT. In one non-limiting example, there may be a sub-region over which the tension varies from 0 up to a maximum (by absolute value) tension equal to CT, and a region over which the tension is substantially constant, equal to CT.

In some embodiments, the compressive stress profile a of the glass article described herein has a slope $m_a$ that is within a specified range. In FIG. 7, for example, slope $m_a$ of line a lies between upper boundary $δ_2$ and lower boundary $δ_1$; i.e., $δ_2 ≥ m_a ≥ δ_1$. In some embodiments, 2 MPa/μm≤$m_a$≤200 MPa/μm. In some embodiments, 2 MPa/μm≤$m_a$≤8 MPa/μm, in some embodiments, 3 MPa/μm≤$m_a$≤6 MPa/μm, and in still other embodiments, 2 MPa/μm≤$m_a$≤4.5 MPa/μm.

In certain embodiments, the slope $m_a$ is less than about 1.5 MPa/μm and, in some embodiments, from about 0.7 MPa/μm to about 2 MPa/μm. When the slope $m_a$ has such values and the depth of compression DOC is at least about 100 μm, the resistance of the strengthened glass to at least one type of failure modes (e.g., very deep puncture) that may be prevalent in field failures certain device designs is particularly advantageous.

Figure 8:
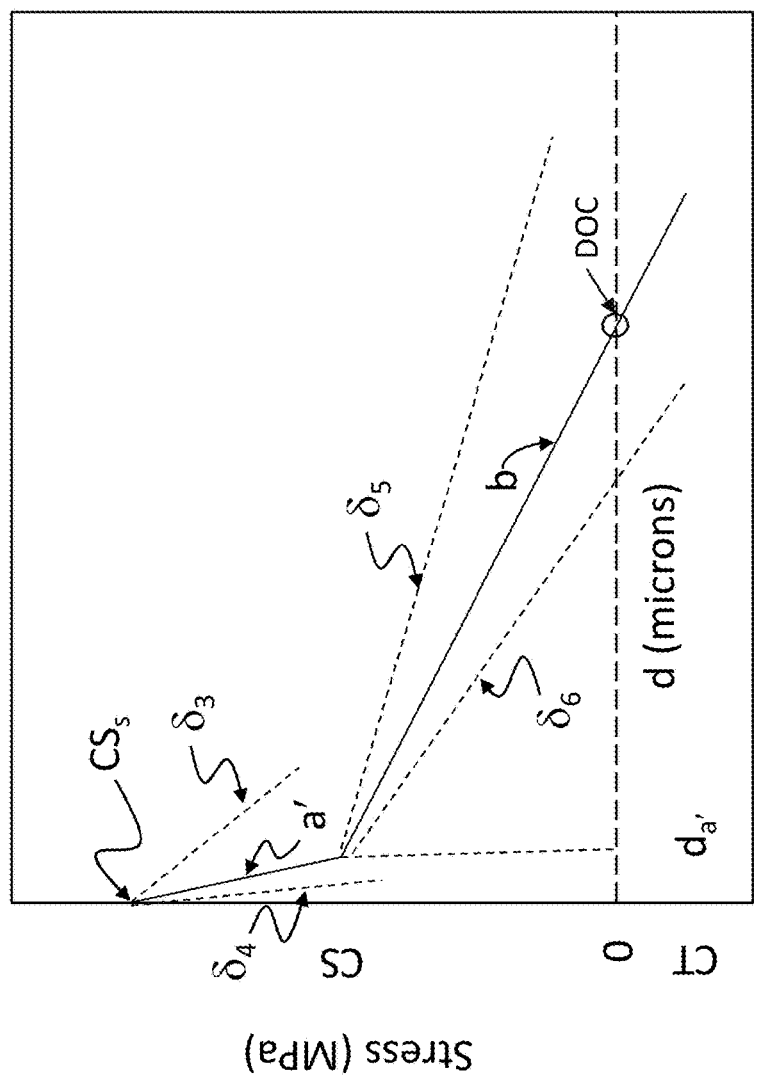
FIG. 8 is a schematic representation of a compressive stress profile of a substrate according to one or more embodiments.

In other embodiments, the compressive stress profile is a combination of more than one substantially linear function, as schematically shown in FIG. 8. As seen in FIG. 8, the compressive stress profile has a first segment or portion a' and a second segment or portion b. First portion a exhibits substantially linear behavior from the strengthened surface of the glass article to a depth $d_a$. Portion a' has a slope $m_{a'}$ and y intercept $CS_s$. Second portion b of the compressive stress profile extends from approximately depth $d_a$ to depth of compression DOC, and has a slope $m_b$. The compressive stress $CS(d_a)$ at depth $d_a$ is given by the expression $$CS(d_a) \approx CS_s - d_a(m_{a'}) \qquad (7).$$

In some embodiments, depth $d_a$ is in a range from about 3 μm to about 8 μm; i.e., 3 μm≤$d_a$≤8 μm. In other embodiments, 3 μm≤$d_a$≤10 μm. In yet other embodiments, 3 μm≤$d_a$≤12 μm.

In some embodiments, the compressive stress profile may include additional segments. In some embodiments, different linear portions or segments of the compressive stress profile may be joined by a transitional region (not shown) in which the slope of the profile transitions from a first slope to a second slope (e.g., from $m_{a'}$ to $m_{b'}$).

As shown in FIG. 8, the slope of portion a' of the compressive stress profile is much steeper than the slope of portion b—i.e., $|m_{a'}| \geq |m_b|$. This corresponds to a condition in which a compressive stress profile having a "spike" at the surface of the glass article is created by multiple ion exchange processes carried out in succession in order to provide the surface with sufficient compressive stress to withstand the introduction or growth of some flaws produced through impact.

In some embodiments, the compressive stress profiles a and b of the glass article described herein have slopes $m_{a'}$ and $m_b$, respectively, that are within specified ranges. In FIG. 8, for example, slope $m_{a'}$ of line a' lies between upper boundary $\delta_3$ and lower boundary $\delta_4$ and slope $m_b$ of line b lies between upper boundary $\delta_5$ and lower boundary $\delta_6$; i.e., $\delta_4 \geq m_{a'} \geq \delta_3$ and $\delta_6 \geq m_b \geq \delta_5$. In some embodiments, 40 MPa/µm≤$m_{a'}$≤200 MPa/µm, and 2 MPa/µm≤$m_b$≤8 MPa/µm. In some embodiments, 40 MPa/µm≤$m_{a'}$≤120 MPa/µm and, in some embodiments, 50 MPa/µm≤$m_{a'}$≤120 MPa/µm.

In some embodiments, the glass substrate has a compressive region having a compressive stress $CS_s$ of at least about 150 MPa at a surface of the glass article, wherein the compressive region extends from the surface to a depth of compression DOC of at least about 45 µm and has a compressive stress profile with a first portion a extending to a depth $d_a$ of at least about 45 µm from the surface and having a slope $m_a$, wherein 2 MPa/µm≤$m_a$≤8 MPa/µm, and optionally a second portion a' extending from the surface to a depth $d_{a'}$ of at least about 3 µm, wherein 40 MPa/µm≤$m_{a'}$≤200 MPa/µm (or 40 MPa/µm≤$m_{a'}$≤120 MPa/µm or 3 MPa/µm≤$m_{a'}$≤6 MPa/µm). In some embodiments, the compressive stress profile comprises: a first portion a extending from the surface to a depth $d_a$ and having a slope $m_a$, wherein 3 µm≤$d_a$≤8 µm and 40 MPa/µm≤$m_a$≤200 MPa/µm (or 40 MPa/µm≤$m_a$≤120 MPa/µm or 50 MPa/µm≤$m_a$≤120 MPa/µm); and a second portion b extending from $d_a$ to up to the depth of compression DOC and having a slope $m_b$, wherein 2 MPa/µm≤$m_b$≤8 MPa/µm.

The depth $d_a$ may be equal to the depth of compression and first portion a extends from the surface to $d_a$. In some embodiments, the second portion a' extending from the surface to a depth $d_{a'}$ and the first portion a extending from $d_{a'}$ up to the depth $d_a$. The thickness may be in a range from about 0.1 mm up to about 1.5 mm.

Exemplary ion-exchangeable glasses that may be used in the strengthened glass substrates described herein may include alkali aluminosilicate glass compositions or alkali aluminoborosilicate glass compositions, though other glass compositions are contemplated. As used herein, "ion exchangeable" means that a glass substrate is capable of exchanging cations located at or near the surface of the glass substrate with cations of the same valence that are either larger or smaller in size. In one or more embodiments, the glass compositions utilized to form the glass substrates may be exhibit a liquidus viscosity of at least 130 kilopoise. One exemplary glass composition comprises $SiO_2$, $B_2O_3$ and $Na_2O$, where ($SiO_2+B_2O_3$)≥66 mol. %, and $Na_2O$≥9 mol. %. In an embodiment, the strengthened glass substrate includes a glass composition with at least 6 wt. % aluminum oxide. In a further embodiment, the strengthened glass substrate (or non-strengthened glass substrate) includes a glass composition with one or more alkaline earth oxides, such that a content of alkaline earth oxides is at least 5 wt. %. Suitable glass compositions, in some embodiments, further comprise at least one of $K_2O$, MgO, and CaO. In a particular embodiment, the glass compositions used in the strengthened glass substrate (or non-strengthened glass substrate) can comprise 61-75 mol. % SiO2; 7-15 mol. % $Al_2O_3$; 0-12 mol. % $B_2O_3$; 9-21 mol. % $Na_2O$; 0-4 mol. % $K_2O$; 0-7 mol. % MgO; and 0-3 mol. % CaO.

A further example glass composition suitable for the strengthened glass substrate or non-strengthened glass substrate comprises: 60-70 mol. % $SiO_2$; 6-14 mol. % $Al_2O_3$; 0-15 mol. % $B_2O_3$; 0-15 mol. % $Li_2O$; 0-20 mol. % $Na_2O$; 0-10 mol. % $K_2O$; 0-8 mol. % MgO; 0-10 mol. % CaO; 0-5 mol. % $ZrO_2$; 0-1 mol. % $SnO_2$; 0-1 mol. % $CeO_2$; less than 50 ppm $As_2O_3$; and less than 50 ppm $Sb_2O_3$; where 12 mol. %≤($Li_2O+Na_2O+K_2O$)≤20 mol. % and 0 mol. %≤(MgO+CaO)≤10 mol. %.

A still further example glass composition suitable for the strengthened glass substrate or non-strengthened glass substrate comprises: 63.5-66.5 mol. % $SiO_2$; 8-12 mol. % $Al_2O_3$; 0-3 mol. % $B_2O_3$; 0-5 mol. % $Li_2O$; 8-18 mol. % $Na_2O$; 0-5 mol. % $K_2O$; 1-7 mol. % MgO; 0-2.5 mol. % CaO; 0-3 mol. % $ZrO_2$; 0.05-0.25 mol. % $SnO_2$; 0.05-0.5 mol. % $CeO_2$; less than 50 ppm $As_2O_3$; and less than 50 ppm $Sb_2O_3$; where 14 mol. %≤($Li_2O+Na_2O+K_2O$)≤18 mol. % and 2 mol. %≤(MgO+CaO)≤7 mol. %.

In a particular embodiment, an alkali aluminosilicate glass composition suitable for the strengthened glass substrate or non-strengthened glass substrate comprises alumina, at least one alkali metal and, in some embodiments, greater than 50 mol. % $SiO_2$, in other embodiments at least 58 mol. % $SiO_2$, and in still other embodiments at least 60 mol. % $SiO_2$, wherein the ratio $$\frac{Al_2O_3 + B_2O_3}{\Sigma \text{ modifiers}} > 1,$$

where in the ratio the components are expressed in mol. % and the modifiers are alkali metal oxides. This glass composition, in particular embodiments, comprises: 58-72 mol. % $SiO_2$; 9-17 mol. % $Al_2O_3$; 2-12 mol. % $B_2O_3$; 8-16 mol. % $Na_2O$; and 0-4 mol. % $K_2O$, wherein the ratio $$\frac{Al_2O_3 + B_2O_3}{\Sigma \text{ modifiers}} > 1.$$

In still another embodiment, the strengthened glass substrate or non-strengthened glass substrate may include an alkali aluminosilicate glass composition comprising: 64-68 mol. % $SiO_2$; 12-16 mol. % $Na_2O$; 8-12 mol. % $Al_2O_3$; 0-3 mol. % $B_2O_3$; 2-5 mol. % $K_2O$; 4-6 mol. % MgO; and 0-5 mol. % CaO, wherein: 66 mol. %≤$SiO_2+B_2O_3+CaO$≤69 mol. %; $Na_2O+K_2O+B_2O_3+MgO+CaO+SrO$>10 mol. %; 5 mol. %≤MgO+CaO+SrO≤8 mol. %; ($Na_2O+B_2O_3$)–$Al_2O_3$≤2 mol. %; 2 mol. %≤$Na_2O–Al_2O_3$≤6 mol. %; and 4 mol. %≤($Na_2O+K_2O$)–$Al_2O_3$≤10 mol. %.

In an alternative embodiment, the strengthened glass substrate or non-strengthened glass substrate may comprise an alkali aluminosilicate glass composition comprising: 2 mol % or more of $Al_2O_3$ and/or $ZrO_2$, or 4 mol % or more of $Al_2O_3$ and/or $ZrO_2$.

In some embodiments, the compositions used for the glass substrate may be batched with 0-2 mol. % of at least one fining agent selected from a group that includes $Na_2SO_4$, NaCl, NaF, NaBr, $K_2SO_4$, KCl, KF, KBr, and $SnO_2$.

Where the substrate 100 includes a crystalline substrate, the substrate may include a single crystal, which may include $Al_2O_3$. Such single crystal substrates are referred to as sapphire. Other suitable materials for a crystalline substrate include polycrystalline alumina layer and/or or a spinel ($MgAl_2O_4$).

Optionally, the crystalline substrate 100 may include a glass ceramic substrate, which may be strengthened or non-strengthened. Examples of suitable glass ceramics may include $Li_2O$—$Al_2O_3$—$SiO_2$ system (i.e. LAS-System) glass ceramics, MgO—$Al_2O_3$—$SiO_2$ System (i.e. MAS-System) glass ceramics, and/or glass ceramics that include a predominant crystal phase including β-quartz solid solution, β-spodumene ss, cordierite, and lithium disilicate. The glass ceramic substrates may be strengthened using the glass substrate strengthening processes disclosed herein. In one or more embodiments, MAS-System glass ceramic substrates may be strengthened in $Li_2SO_4$ molten salt, whereby $2Li^+$ for $Mg^{2+}$ exchange can occur.

The substrate 100 according to one or more embodiments can have a thickness ranging from about 100 μm to about 5 mm. Example substrate 100 thicknesses range from about 100 μm to about 500 μm (e.g., 100, 200, 300, 400 or 500 μm). Further example substrate 100 thicknesses range from about 500 μm to about 1000 μm (e.g., 500, 600, 700, 800, 900 or 1000 μm). The substrate 100 may have a thickness greater than about 1 mm (e.g., about 2, 3, 4, or 5 mm). In one or more specific embodiments, the substrate 100 may have a thickness of 2 mm or less or less than 1 mm. The substrate 100 may be acid polished or otherwise treated to remove or reduce the effect of surface flaws.

Layer

Embodiments of the layer 200 described herein may be utilized to impart scratch-resistance, fracture-resistance or damage resistance to the substrate 100 and/or layered-substrate 10. Optionally, the layer 200 may be utilized to improve the optical properties of the substrate 100 and/or the layered-substrate 10. These attributes of the layer 200 may be used in combination. Accordingly, the layer 200 may be referred to herein as a "scratch-resistant" layer, a "fracture-resistant" layer, or more generally, a "damage-resistant" layer. The layer 200 may be continuous or discontinuous layer.

In one or more embodiments, the layered substrate 10 and/or the layer 200 and/or the hardness of one or more of the sub-layers that form the layer may be characterized by its measured hardness. As used herein, hardness is measured using a "Berkovich Indenter Hardness Test", which includes measuring the hardness of a material on a surface thereof by indenting the surface with a diamond Berkovich indenter. The Berkovich Indenter Hardness Test includes indenting the surface with the diamond Berkovich indenter to form an indent having an indentation depth in the range from about 50 nm to about 1000 nm (or the entire thickness of the material or layer, whichever is less) and measuring the maximum hardness from this indentation along the entire indentation depth range or a segment of this indentation depth), generally using the methods set forth in Oliver, W. C.; Pharr, G. M. An improved technique for determining hardness and elastic modulus using load and displacement sensing indentation experiments. *J. Mater. Res.*, Vol. 7, No. 6, 1992, 1564-1583; and Oliver, W. C.; Pharr, G. M. Measurement of Hardness and Elastic Modulus by Instrument Indentation: Advances in Understanding and Refinements to Methodology. *J. Mater. Res.*, Vol. 19, No. 1, 2004, 3-20. The indentation depth is made and measured from the surface material or layer. As used herein, hardness refers to a maximum hardness, and not an average hardness.

Typically in nanoindentation measurement methods (such as by using a Berkovich indenter) of a coating that is harder than the underlying substrate, the measured hardness may appear to increase initially due to development of the plastic zone at shallow indentation depths and then increases and reaches a maximum value or plateau at deeper indentation depths. Thereafter, hardness begins to decrease at even deeper indentation depths due to the effect of underlying the substrate.

The indentation depth range and the hardness values at certain indentation depth range(s) are selected to identify a particular hardness response of the material or layer, described herein, without the effect of the underlying substrate. When measuring hardness of a material or layer (when disposed on a substrate) with a Berkovich indenter, the region of permanent deformation (plastic zone) of a material is associated with the hardness of the material. During indentation, an elastic stress field extends well beyond this region of permanent deformation. As indentation depth increases, the apparent hardness and modulus are influenced by stress field interactions with the underlying substrate. The substrate influence on hardness occurs at deeper indentation depths (i.e., typically at depths greater than about 10% of the material or layer thickness). Moreover, a further complication is that the hardness response requires a certain minimum load to develop full plasticity during the indentation process. Prior to that certain minimum load, the hardness shows a generally increasing trend.

At small indentation depths (which also may be characterized as small loads) (e.g., up to about 100 nm, or less than about 70 nm) the apparent hardness of a material appears to increase dramatically versus indentation depth. This small indentation depth regime does not represent a true metric of hardness but instead, reflects the development of the aforementioned plastic zone, which is related to the finite radius of curvature of the indenter. At intermediate indentation depths, the apparent hardness approaches maximum levels. At deeper indentation depths, the influence of the substrate becomes more pronounced as the indentation depths increase. Hardness begins to drop dramatically once the indentation depth exceeds about 30% of the layer thickness.

It has been observed that the measurement at intermediate indentation depths (at which hardness approaches and is maintained at maximum levels) and deeper indentation depths depends on the thickness of a material or layer. When the hardness response of four layers of the same material having different thicknesses (e.g., 500 nm, 1000 nm, 1500 nm and 2000 nm) was evaluated using the Berkovich Indenter Hardness Test, the 500 nm-thick layer exhibited its maximum hardness at indentation depths from about 100 nm to 180 nm, followed by a dramatic decrease in hardness at indentation depths from about 180 nm to about 200 nm (indicating the hardness of the substrate influencing the hardness measurement), the 1000 nm-thick layer exhibited a maximum hardness at indentation depths from about 100 nm to about 300 nm, followed by a dramatic decrease in hardness at indentation depths greater than about 300 nm, the 1500 nm-thick layer exhibited a maximum hardness at indentation depths from about 100 nm to about 550 nm, and the 2000-nm thick layer exhibited a maximum hardness at indentation depths from about 100 nm to about 600 nm.

In some embodiments, having the maximum hardness at indentation depths greater than about 200 nm provides a material or a layer thereof having sufficient hardness to provide scratch resistance, that is not influenced by the substrate. In some embodiments, having a maximum hardness at such indentation depths provides resistance to specific scratches such as microductile scratches (which typically have depths of about 200 nm to about 400 nm). As used herein, the phrase "microductile scratch" includes a single groove in a material having extended length. For example, the article (or the surface of the article) may be resistant to microductile scratches because the article exhibits the hardness values recited herein along specific indentation depths, as measured by a Berkovich Indenter Hardness Test.

In one or more specific embodiments, the layer 200 has a hardness of about greater than 8 GPa, as measured by the Berkovich Indenter Hardness Test along an indentation depth of about 50 nm or greater or about 100 nm or greater (e.g., from about 100 nm to about 300 nm, from about 100 nm to about 400 nm, from about 100 nm to about 500 nm, from about 100 nm to about 600 nm, from about 200 nm to about 300 nm, from about 200 nm to about 400 nm, from about 200 nm to about 500 nm, or from about 200 nm to about 600 nm). In one or more embodiments, the layer 200 has a hardness of about 16 GPa or greater, about 17 GPa or greater, about 18 GPa or greater, about 19 GPa or greater, about 20 GPa or greater, about 22 GPa or greater along such indentation depths. The layer 200 may have at least one sub-layer having a hardness of about 16 GPa or greater, about 17 GPa or greater, about 18 GPa or greater, about 19 GPa or greater, about 20 GPa or greater, about 22 GPa or greater, as measured by the Berkovich Indenter Hardness Test along indentation depths of about 50 nm or greater or about 100 nm or greater (from about 100 nm to about 300 nm, from about 100 nm to about 400 nm, from about 100 nm to about 500 nm, from about 100 nm to about 600 nm, from about 200 nm to about 300 nm, from about 200 nm to about 400 nm, from about 200 nm to about 500 nm, or from about 200 nm to about 600 nm). In one or more specific embodiments, the layer 200 (or at least one sub-layer forming the same) may have a hardness in the range from about 15 GPa to about 25 GPa, from about 16 GPa to about 25 GPa, from about 18 GPa to about 25 GPa, from about 20 GPa to about 25 GPa, from about 22 GPa to about 25 GPa, from about 23 GPa to about 25 GPa and all ranges and sub-ranges therebetween, as measured by the Berkovich Indenter Hardness Test along an indentation depth of about 50 nm or greater or about 100 nm or greater (e.g., from about 100 nm to about 300 nm, from about 100 nm to about 400 nm, from about 100 nm to about 500 nm, from about 100 nm to about 600 nm, from about 200 nm to about 300 nm, from about 200 nm to about 400 nm, from about 200 nm to about 500 nm, or from about 200 nm to about 600 nm). As will be described below, the layer 200 imparts a hardness to the layered-substrate 10. The hardness of the layer 200 may be selected to be greater than the hardness of the substrate 100.

Embodiments of the layer 200 described herein may be characterized by its modulus and/or the modulus of one or more of the sub-layers that form the layer. As used herein, "modulus" refers to Young's modulus. In one or more specific embodiments, the layer 200 has a modulus of 150 GPa or greater. In one or more embodiments, the layer 200 has a modulus of about 160 GPa or greater, about 170 GPa or greater, about 180 GPa or greater, about 190 GPa or greater, about 200 GPa or greater, about 220 GPa or greater, as measured according to known methods, including using nano-indentation methods using a diamond Berkovich indenter. In one or more embodiments, the layer 200 exhibits a modulus in the range from about 100 GPa to about 250 GPa or from about 150 GPa to about 240 GPa, and all ranges and sub-ranges therebetween.

In some embodiments, the layer 200 may exhibit a scratch resistance that is measured by a reduction in scratch depth and/or scratch width. In this manner, the layer 200 according to one or more embodiments specifically prevents or mitigates single event scratch damage by reducing the scratch width and/or depth. Layered-substrate 10 that include the layer 200 may exhibit a reduction in scratch depth and/or scratch width, when compared to the scratch depth and/or scratch width exhibited by the substrate 100 (experiencing the same scratch conditions) without the layer 200. This reduction in scratch depth and/or width may be exhibited whether the substrate 100 is amorphous and/or crystalline and/or whether the substrate 100 is strengthened or not strengthened, as applicable.

In one or more embodiments, when the layered-substrate 10 is scratched using a diamond Berkovich indenter, using a load of 160 mN at a speed of 10 µm/second for a length of at least 100 µm along the surface of the layered-substrate (on the side of the layered-substrate on which the layer 200 is disposed), the resulting scratch has a depth that is at least 20% less and in some cases, at least 30% less, than the depth of a scratch formed identically (i.e., using the same indenter, load, speed, and length) on a substrate 100, without the layer 200 disposed thereon. When the load is reduced to 120 mN, 60 mN or 30 mN, the scratch depth reduction increases even more. In other words, at lower loads, the resulting scratch depth may be even shallower in the layered-substrate 10 according to one or more embodiments than exhibited in substrate 100 without the layer 200 disposed thereon. In addition, this scratch resistance may be exhibited when the layered-substrate 10 is scratched using the diamond Berkovich indenter, at a speed of 10 nm/second for a length of at least 1 mm, at least 2 mm, at least 3 mm, at least 4 mm or at least 5 mm. In one or more embodiments, the layer 200 exhibits scratch resistance such that, when a layered-substrate 10 including the layer 200 is scratched by a diamond Berkovich indenter using a load of 160 mN at a speed of 10 µm/seconds for at least a length of 100 µm along the surface of the layered-substrate, the resulting scratch has a scratch depth of less than 300 nm, less than 290 nm, less than 280 nm, less than 270 nm, less than 260 nm, less than 250 nm, less than 240 nm, less than 230 nm, less than 220 nm, less than 210 nm, less than 200 nm, less than 180 nm, less than 170 nm, less than 160 nm, less than 150 nm, less than 140 nm, less than 130 nm, less than 120 nm, less than 110 nm, less than 100 nm, less than 90 nm, less than 80 nm, less than 70 nm, less than 60 nm, less than 50 nm, less than 40 nm, less than 30 nm, less than 20 nm, less than 10 nm and all ranges and sub-ranges therebetween. The scratch depths described herein may be measured from the original and undisturbed surface of the layer 200. In other words, the scratch depth does not include any amount of layer 200 that may be built up around the edges of the scratch due to displacement of the layer materials caused by the penetration of the diamond Berkovich indenter into the layer.

In one or more embodiments, when the layered-substrate 10 is scratched using a diamond Berkovich indenter, using a load of 160 mN at a speed of 10 µm/second for a length of at least 100 µm along the surface of the layered-substrate (on the side of the layered-substrate on which the layer 200 is disposed), the resulting scratch has a width that is at least 10% less and in some cases, at least 30% less or even 50% less, than the width of a scratch formed identically (i.e., using the same indenter, load, speed, and length) on a substrate 100, without the layer 200 disposed thereon. When the load is reduced to 120 mN, 60 mN or 30 mN, the scratch width reduction increases even more. In other words, at lower loads, the resulting scratch width may be even narrower in the layered-substrate 10 according to one or more embodiments than exhibited in substrate 100 without the layer 200 disposed thereon. In addition, this scratch resistance may be exhibited when the layered-substrate 10 is scratched using the diamond Berkovich indenter, at a speed of 10 μm/second for a length of at least 1 mm, at least 2 mm, at least 3 mm, at least 4 mm or at least 5 mm. In one or more embodiments, the layer 200 exhibits scratch resistance such that, when a layered-substrate 10 including the layer 200 is scratched by a diamond Berkovich indenter using a load of 160 mN at a speed of 10 μm/seconds for at least a length of 100 μm along the surface of the layered-substrate, the resulting scratch has a scratch width of less than 10 nm, less than 9.5 nm, less than 9 nm, less than 8.5 nm, less than 8 nm, less than 7.5 nm, less than 7 nm, less than 6.5 nm, less than 6 nm, less than 5.5 nm, less than 5 nm, less than 4.5 nm, less than 4 nm, less than 3.5 nm, less than 3 nm, less than 2.5 nm, less than 2 nm, less than 1.5 nm, less than 1 nm, less than 0.5 nm, and all ranges and sub-ranges therebetween. The scratch widths described herein may be measured from the original and undisturbed surface of the layer 200. In other words, the scratch width does not include any amount of layer 200 that may be built up around the edges of the scratch due to displacement of the layer materials caused by the penetration of the diamond Berkovich indenter into the layer.

In one or more embodiments, the layer 200 described herein may exhibit scratch resistance when evaluated using a garnet sandpaper test. The garnet sandpaper test is intended to replicate or imitate the day-to-day conditions of use of the materials described herein, when incorporated into mobile electronic devices, such as mobile phones. In one or more embodiments, the materials described herein are substantially free of any scratches on the surface including the layer, when observed with the naked eye, after the surface has been swiped a single time with 150-grit garnet sandpaper (supplied by 3M) by hand.

The layer 200 may have a thickness of 0.05 μm or 0.1 μm or greater. In one or more specific embodiments, the thickness of layer 200 may be 2 μm or greater, or 3 μm or greater. Specific layers 200 may have a thickness of 0.05 μm, 0.06 μm, 0.07 μm, 0.08 μm, 0.09 μm, 0.1 μm, 0.2 μm, 0.3 μm, 0.4 μm, 0.5 μm, 0.6 μm, 0.7 μm, 0.8 μm, 0.9 μm, 1.0 μm, 1.1 μm, 1.3 μm, 1.4 μm, 1.5 μm, 1.6 μm, 1.7 μm, 1.8 μm, 1.9 μm, 2.1 μm, 2.2 μm, 2.3 μm, 2.4 μm, 2.5 μm, 2.6 μm, 2.7 μm, 2.8 μm, 2.9 μm, 3.0 μm and all ranges and sub-ranges therebetween. The thickness of the layer 200 may be substantially uniform.

The layer 200 in accordance with one or more embodiments may be substantially clear or transparent in the optical regime (i.e., the wavelength range from about 380 nm to about 780 nm). In one or more embodiments, the layer 200 maintains or reduces the reflectivity of the layered-substrate 10 and does not include any materials for intentionally increasing the reflectivity of the layered-substrate 10. In one or more alternative embodiments, the layer 200 may be substantially opaque. In one or more embodiments, the layer 200 has an average refractive index in the range from about 1.8 to 2.2. In one or more embodiments, the layer 200 and/or the layered-substrate 10 do not provide a reflectance or transmittance color tone (or, in other words, the reflectance color tone provided is neutral or colorless). In one or more embodiments, the layered-substrate 10 has a color presented in CIELAB color space coordinates in transmittance, determined from specular reflectance measurements using a spectrophotometer, with illuminant D65, of CIE a* in the range from about −2 to about 2 (e.g., from −1.5 to 1.5, from −1 to 1, from −0.5 to 0.5, −0.25 to 0.25, −0.1 to 0.1, and all ranges an sub-ranges therebetween); CIE b* in the range from about −4 to about 4 (e.g., from about −3.5 to 3.5, −3 to 3, −2.5 to 2, −2 to 2, −1.5 to 1.5, −1 to 1, −0.5 to 0.5, −0.1 to 0.1, −0.05 to 0.05, and all ranges an sub-ranges therebetween); and CIE L* in the range from about 90 to about 100 (e.g., 91 to 100, 92 to 100, 93 to 100, 94 to 100, 95 to 100, 96 to 100, 97 to 100, 98 to 100, and all ranges an sub-ranges therebetween). In one or more embodiments, the layered-substrate 10 has a reflectance color presented in CIELAB color space coordinates, determined from specular reflectance measurements using a spectrophotometer, with illuminant D65, of CIE a* in the range from about −2 to about 2 (e.g., from −1.5 to 1.5, from −1 to 1, from −0.5 to 0.5, −0.25 to 0.25, −0.1 to 0.1, and all ranges an sub-ranges therebetween); CIE b* in the range from about −4 to about 4 (e.g., from about −3.5 to 3.5, −3 to 3, −2.5 to 2, −2 to 2, −1.5 to 1.5, −1 to 1, −0.5 to 0.5, −0.1 to 0.1, −0.05 to 0.05, and all ranges an sub-ranges therebetween); and CIE L* of 50 or less (e.g., 45 or less, 40 or less, 35 or less, 30 or less, 25 or less, 20 or less, or 15 or less and all ranges an sub-ranges therebetween).

In one or more embodiments, the layer 200 may include a metal oxide, a metal nitride, a metal carbide, a metal boride, diamond-like carbon or a combination thereof. In some embodiments, layer 200 may include metal oxynitrides and/or oxycarbides. In one or more specific embodiments, the metal(s) utilized in the metal oxides, metal nitrides, metal oxynitrides, metal carbides, metal oxycarbides, and/or metal borides may include B, Al, Si, Ti, V, Cr, Y, Zr, Nb, Mo, Sn, Hf, Ta, W and combinations thereof. Examples of suitable materials that may be included in the layer 200 include $Si_3N_4$, AlN, $AlO_xN_y$, $SiO_xN_y$, $Al_xSi_yN$, SiC and other similar materials. In one or more embodiments, the layer 200 includes the same material throughout the layer.

In one or more embodiments, the layer 200 may include an oxygen content gradient, a nitrogen content gradient, a silicon content gradient and aluminum content gradient and various combinations thereof. As used herein, the term "gradient" refers to a variation in atomic % of an element in the composition of a layer. The variation in atomic % of an element may occur among a plurality of sub-layers (not shown) of the layer 200. In some instances, up to 10, 20, 30, 40, 50, 60, 70, 80, 90, 100, 110, 120 or even 130 sub-layers having a different atomic % of an element from one another may be utilized to form a layer having a gradient. In a layer that includes an oxygen gradient, the amount of oxygen (atomic %) in the composition of the layer at or near the interface between the layer and the substrate 100 may differ from the amount of oxygen (atomic %) in the composition of the layer at or near the opposite side of the layer (or near the interface between the layer 200 and an additional layer, as described herein) and other areas therebetween.

In one or more embodiments, the composition gradient in the layer 200 may include a silicon/aluminum composition gradient, where the atomic % of silicon and aluminum change along the thickness of the layer independently of one another or in relation to one another. In other embodiments, the compositional gradient may include an oxygen/nitrogen composition gradient, where the atomic % of oxygen and nitrogen change along the thickness of the layer independently of one another or in relation to one another. In one or more embodiments, the ratio of oxygen to nitrogen at or near the interface between the substrate 100 and the layer 200 may be greater than the ratio of oxygen to nitrogen at the opposite side of the layer 200 (or near the interface between the layer 200 and an additional layer, as described herein) and other areas therebetween. For example, there may be very little or no nitrogen present in the layer 200 at or near the interface between the substrate 100 and the layer 200 and/or there may be very little or no oxygen present in the layer 200 at the opposite side of the layer 200 (or near the interface between the layer 200 and an additional layer, as described herein). In one or more embodiments, the ratio of silicon to aluminum at or near the interface between the substrate 100 and the layer 200 may be greater than the ratio of silicon to aluminum at the opposite side of the layer 200 (or near the interface between the layer 200 and an additional layer, as described herein). For example, there may be very little or no aluminum present in the layer 200 at or near the interface between the substrate 100 and the layer 200 and/or there may be very little or no silicon present in the layer at the opposite side of the layer 200 (or near the interface between the layer 200 and an additional layer, as described herein).

In one or more embodiments, the oxygen content gradient and/or the nitrogen content gradient may be controlled by the flow rate of oxygen gas and/or nitrogen gas introduced into the deposition process (i.e., into the deposition chamber in which the layer 200 is deposited onto the substrate 100). To increase the oxygen or nitrogen content, the flow rate of oxygen or nitrogen is increased. In some embodiments, the aluminum and/or silicon gradient may be controlled by controlling the power directed at the aluminum and/or silicon source materials (e.g., where sputtering is used to form the layer, the power directed at the aluminum and/or silicon sputtering targets is controlled). To increase the aluminum or silicon content, the power directed to the aluminum and/or silicon source materials is increased.

In one or more embodiments, the layered-substrate 10 may include one or more additional layers 300. The additional layer 300 may be disposed on layer 200 (as shown in FIG. 1D) or between the layer 200 and the substrate 100 (as shown in FIG. 1E). Where multiple layers are utilized, a first additional layer 310 may be disposed between the layer 200 and the substrate 100 (as shown in FIG. 1F) and a second additional layer 320 may be disposed on the layer 200. In some embodiments, the one or more additional layers 300 may manage one or more optical properties of the layered-substrate (e.g., average light reflectivity, average light transmission, reflectance, transmittance, color inreflectance and/or color in transmittance) and/or may impart scratch-resistance properties to the layered-substrate. For example, the one or more additional layers 300 may exhibit a refractive index that is less than the refractive index of the layer. In another embodiment, the one or more additional layers 300 may have a thickness that also differs or is the same as the layer and, in combination with the refractive index thereof, the one or more additional layers may modify the average light reflectivity, average light transmission, reflectance, transmittance, color in transmittance and/or color in reflectance of the layered-substrate. In another embodiment, one or more additional layers may have a specific hardness and/or thickness to modify the scratch-resistance of the layered-substrate.

In one variant, the one or more additional layers 300 may include a metal oxide, a metal nitride, a metal oxynitride or a combination thereof. Exemplary metals include B, Al, Si, Ti, V, Cr, Y, Zr, Nb, Mo, Sn, Hf, Ta and W. In one or more specific embodiments, the layer 200 may include AlOxNy and the additional layer 300 may include $SiO_2$ or $Al_2O_3$. In another variant, the layered-substrate may include a first additional layer of $SiO_2$ or $Al_2O_3$ and a second additional layer including the other of $SiO_2$ and $Al_2O_3$. The first additional layer and the second additional layer may include different materials or the same materials. The first and second additional layers may exhibit the same or different thicknesses as each other or the same or different thicknesses (each or together) as the layer.

In some embodiments, the additional layer may include a crack mitigating layer and such layer may be disposed between the layer and the substrate. Examples of crack mitigating layers are described in U.S. patent application Ser. No. 14/052,055, filed on Oct. 11, 2013, U.S. patent application Ser. No. 14/053,093, filed on Oct. 14, 2013, and U.S. patent application Ser. No. 14/053,139, filed on Oct. 14, 2013, the contents of which are incorporated herein by reference in their entirety.

In one or more embodiments, the materials utilized in the layer 200 may be selected to optimize the various properties thereof. In some embodiments, the oxygen content of the layer 200 may be modified to tune its optical properties and/or mechanical properties (e.g., hardness, modulus etc.). Oxygen-containing materials such as $Al_2O_3$, $SiO_2$, $SiO_xN_y$, $AlO_xN_y$, can be utilized to minimize the variation on the reflectance color points as the viewing angle is changed from normal incidence (i.e., 0 degrees) to oblique incidence (e.g., 70 degrees or greater, 75 degrees or greater, 80 degrees or greater, 85 degrees or greater, 86 degrees or greater, 87 degrees or greater, 88 degrees or greater, 89 degrees or greater or 89.5 degrees or greater; however oblique incidence may be less than 90 degrees). In one or more specific embodiments, the amount of oxygen in the layer 200 or in any of its sub-layers may be tuned to control the refractive index of the layer 200 and/or other properties thereof.

In one or more embodiments, the materials utilized in the layer 200 may be selected to optimize the scratch resistance of the layer. For example, $Si_3N_4$, AlN, SiC and the like may be used for specific properties (e.g., hardness) and may comprise at least 50% by weight of the materials utilized in the layer 200. These materials may optionally comprise 55% by weight or more, 60% by weight or more, 65% by weight or more, 70% by weight or more or 75% by weight or more of the materials utilized in the layer 200.

The layer 200 may be formed using any known methods in the art. For example, suitable methods include discontinuous or continuous vacuum deposition processes, such as chemical vapor deposition (e.g., plasma enhanced chemical vapor deposition), physical vapor deposition (e.g., reactive or nonreactive sputtering or laser ablation), thermal or e-beam evaporation and/or atomic layer deposition. In one or more specific embodiments, the layer 200 may be formed by methods other than atomic layer deposition. The layer 200 may be less conformal than if the layer was formed by atomic layer deposition or may be less conformal than other layers formed by atomic layer deposition. In some instances, the substrate 100 may include microcracks; however, the layer 200 does not fill in a significant number of the microcracks found in the glass.

Layered-Substrate

In one or more embodiments, the layered-substrate 10 has a hardness of about greater than 8 GPa, as measured by the Berkovich Indenter Hardness Test along an indentation depth of about 50 nm or greater or about 100 nm or greater (e.g., from about 100 nm to about 300 nm, from about 100 nm to about 400 nm, from about 100 nm to about 500 nm, from about 100 nm to about 600 nm, from about 200 nm to about 300 nm, from about 200 nm to about 400 nm, from about 200 nm to about 500 nm, or from about 200 nm to about 600 nm). In one or more embodiments, the layered-substrate 10 has a hardness of about 16 GPa or greater, about 17 GPa or greater, about 18 GPa or greater, about 19 GPa or greater, about 20 GPa or greater, about 22 GPa or greater along such indentation depths. In one or more specific embodiments, the layered-substrate 10 may exhibit a measured hardness in the range from about 15 GPa to about 25 GPa, from about 16 GPa to about 25 GPa, from about 18 GPa to about 25 GPa, from about 20 GPa to about 25 GPa, from about 22 GPa to about 25 GPa, from about 23 GPa to about 25 GPa and all ranges and sub-ranges therebetween, as measured by the Berkovich Indenter Hardness Test along an indentation depth of about 50 nm or greater or about 100 nm or greater (e.g., from about 100 nm to about 300 nm, from about 100 nm to about 400 nm, from about 100 nm to about 500 nm, from about 100 nm to about 600 nm, from about 200 nm to about 300 nm, from about 200 nm to about 400 nm, from about 200 nm to about 500 nm, or from about 200 nm to about 600 nm). The hardness of the layered-substrate 10 is greater than the hardness of the underlying substrate 100 in some instances, due to the presence of the layer 200.

In one or more embodiments, the layered-substrate may be characterized by its average flexural strength. As used herein, the term "average flexural strength" is intended to refer to the flexural strength of a layered-substrate (e.g., the layered-substrate 10 and/or the substrate 100), or the strength at which the layered-substrate fractures or breaks under flexural load, as tested through methods such as ring-on-ring, ball-on-ring, or ball drop testing. "Average flexural strength" is measured using at least 5 samples, at least 10 samples or at least 15 samples or at least 20 samples. "Average flexural strength" can also include a mathematical average in terms of load, stress and other measurement parameters known in the art. More broadly, "average flexural strength" may also be defined by other tests such as a ball drop test, where the surface flexural strength is characterized by a ball drop height that can be tolerated without failure. Layered-substrate surface strength may also be tested in a device configuration, where an appliance or device containing the layered-substrate (e.g., the layered-substrate 10 and/or the substrate 100) article is dropped in different orientations that may create a surface flexural stress (i.e., drop tests). "Average flexural strength" may in some cases also incorporate the strength as tested by other methods known in the art, such as 3-point bend or 4-point bend testing. In some cases, these test methods may be significantly influenced by the edge strength of the article (e.g., the layered-substrate 10 and/or the substrate 100).

In one or more embodiments, the layered-substrate exhibits an average flexural strength, as measured by ring-on-ring testing and as described herein, after being abraded that is substantially the same as the average flexural strength of the layered-substrate before being abraded. The average flexural strength after a layered-substrate or substrate is abraded may be referred to as an "abraded strength". As used herein, the term "abraded" includes a process by which the surface of a substrate or layered-substrate is subjected to abrasion. The average flexural strength of such an abraded substrate or layered-substrate can provide an indication of the strength of the substrate or layered-substrate after the substrate or layered-substrate has been subjected to use. In other words, abraded strength provides an indication of how tolerant the substrate or layered-substrate is to flaws or surface damage, such that the average flexural strength of the substrate or layered-substrate remains above a target level in service after the introduction of flaws or surface damage. As used herein, one method of abrading the surface of a substrate or layered-substrate is described in ASTM Method C158-02, which generally provides for a method by which air is used to accelerate particles (e.g., SiC) such that they collide with the surface of the substrate or layered-substrate. The average flexural strength of the layered-substrate is measured by ring-on-ring failure testing.

Ring-on-ring failure testing includes placing the substrate or layered-substrate between a load ring and a support ring. In the case where the layered-substrate is being tested, the side of the layered-substrate on which the layer 200 is disposed, is held in tension between the load ring and the support ring. In the embodiments described herein, the load ring has a diameter of 0.5 inches and the support ring has a diameter of 1 inch. The testing parameters of such embodiments include a contact radius is about 1.6 mm and the cross-head speed of 1.2 mm/minute. To measure the average flexural strength, a load is applied to the load ring to determine the stress at which the substrate or layered-substrate fractures or breaks. Before the test is performed, an adhesive film may be placed on both sides of the substrate or layered-substrate to contain broken glass shards.

In one or more embodiments, the layered-substrate 10 exhibits a first average flexural strength before being abraded, and a second average flexural strength after being abraded, wherein the second average flexural strength is substantially the same, or is at least 80%, at least 82%, at least 84%, at least 86%, at least 88%, at least 90%, at least 92%, at least 94%, at least 96%, at least 98%, or at least 99% of the first average flexural strength.

Embodiments of the layered-substrate 10 disclosed herein demonstrate improved fracture resistance when subjected to repeated drop tests or when subjected to repeated tests in which objects are dropped onto a major surface of the layered-substrate. While the person of ordinary skill in the art may contemplate various experimental parameters for the drop test, the layered-substrate 10 described herein are able to withstand fracture when dropped in a drop test from a height of at least 100 cm onto a drop surface, or from a height of at least 150 cm, or from a height of at least 200 cm, or from a height of about 220 cm. In one or more embodiments, while the person of ordinary skill in the art may contemplate various experimental parameters for a test in which an object is dropped onto a major surface of the layered-substrate, the layered-substrates 10 described herein are able to withstand fracture when such objects are dropped onto the layered-substrate from a height of at least 10 cm, 20 cm, 30 cm, 40 cm, 50 cm, 60 cm, 70 cm, 80 cm, 90 cm, 100 cm, 110 cm, 120 cm, 130 cm, 140 cm, 150 cm, 160 cm, 170 cm, 180 cm, 190 cm, 200 cm, 210 cm, or 220 cm and all ranges and sub-ranges therebetween. This test may be similar or identical to the ball drop test or may use specific objects that are selected to simulate "real world" objects that could impact the surface of the layered-substrate (e.g., the object may have a specific hardness and/or a jagged or rough surface). As used herein, the term "fracture" includes cracks, chips or even mechanical defects in the layer 200, the substrate 100 and/or the layered-substrate 10.

Further demonstrating the improved survivability of the layered-substrate, the layered-substrate 10 is able to withstand fracture when the layered-substrate contacts the drop surface at a flat angle, at a non-flat angle, or both. As used herein, "flat angle" means 180° relative to the drop surface. Various angles relative to the drop surface are contemplated for the "non-flat angle." In the examples below, the non-flat angle is 30° relative to the drop surface. Similarly demonstrating the improved survivability of the layered-substrate, the layered-substrate 10 is able to withstand fracture when an object (e.g., a hard and/or sharp object) contacts the layered-substrate at a flat angle, at a non-flat angle, or both, as defined herein.

In one or more embodiments, where a drop test is contemplated, the drop surface is an abrasive surface configured to simulate damage that may result when an article and/or a device (e.g., an electronic device) is dropped on "real world" surfaces, such as asphalt. Surviving repeated drops onto the abrasive surface is an indication of better performance on asphalt, as well as other surfaces, e.g., concrete or granite. Various materials are contemplated for the abrasive surface. In a specific embodiment, the abrasive surface is sandpaper, such as SiC sandpaper, engineered sandpaper, or any abrasive material having comparable hardness and/or sharpness that is known to one of ordinary skill in the art, disposed on a support (e.g., steel plate). SiC sandpaper having 180 grit and an average particle size of about 80 μm may be used, because it has a known range of particle sharpness, a surface topography more consistent than concrete or asphalt, and a particle size and sharpness that produces the desired level of specimen surface damage. One non-limiting example of commercially available 180 grit SiC sandpaper that may be used in the drop tests described herein is Rhynowet® 180 grit SiC sandpaper produced by Indasa.

In the tests, the sandpaper may be replaced after each drop to avoid "aging" effects that have been observed in repeated use of concrete or asphalt drop surfaces. In addition to aging, different asphalt morphologies and/or different temperatures and humidity may affect the performance of asphalt. Unlike concrete or asphalt, the sandpaper abrasive surface delivers a consistent amount of damage across all samples.

Moreover, in the drop tests (examples of which are provided below), various drop heights are utilized. For example, the drop test may utilize a minimum drop height (for example, a drop height of about 1 meter). A sample set of about 20 layered-substrates are each then dropped from this drop height to observe whether or not each sample fractures. Once the layered-substrate (or substrate or other material being tested) is fractured, the test is stopped. As used herein, the term "fracture" includes the presence of a crack that penetrates the entire thickness of the layered substrate or the substrate alone (where the drop test is performed on a bare substrate). If the layered-substrate does not fracture after a drop from the drop height, the drop test may also be stopped, or the layered-substrate (or substrate or other material being tested) may be repeatedly dropped from that maximum height. The above drop test procedures may be the same where the layered-substrate, substrate or other material is included in a device, which is then subjected to the drop test in the same manner as the layered-substrate, substrate and/or other material. The orientation of the layered-substrate may be controlled to control the surface on which the impact between the layered-substrate and the drop surface occurs. Specifically, the orientation of the layered-substrate may be controlled so that the impact occurs on the surface on which the layer is disposed.

In tests in which an object is dropped onto the surface of the layered-substrate, the surface of the layered-substrate including the layer 200 is exposed to the object being dropped. In other words, the surface of the layered-substrate 10 including the layer 200 experiences the flexural stress imparted by the dropped object. As otherwise described herein, the object may be selected according to known ball drop test methods and/or may be selected for a specific hardness and/or sharp and/or jagged surface(s), so as to impart damage (e.g., scratch) onto the surface simultaneously or immediately before applying a flexural stress on the surface of the layered-substrate 10. In such embodiments, the surface of the layered-substrate 10 that includes the layer 200 experiences surface damage and flexural stress.

Other variations of a test in which the surface of the layered-substrate 10 is damaged simultaneously or immediately before a flexural stress is applied to the layered-substrate may be utilized. For example, the surface of the layered-substrate may be damaged by rubbing sandpaper along the surface, dropping or blasting sand particles onto the surface and the like, followed by subjecting the layered-substrate to a flexural stress test (e.g., ball drop, ring-on-ring, or ball-on-ring).

In the tests in which an object is dropped onto the surface of the layered-substrate 10, various drop heights for the object are utilized. For example, the test in which an object is dropped onto the layered-substrate 10 may utilize a minimum drop height to start (for example, a drop height of about 10-20 cm), and may increase the height by set or variable increments for successive drops. Once the layered-substrate (or substrate or other material being tested) breaks, the test is stopped. Alternatively, if the drop height reaches the maximum drop height (for example, a height of about 220 cm), and the layered-substrate (or substrate or other material being tested) is not fractured after the object has been dropped onto its surface, the test may also be stopped, or the layered-substrate (or substrate or other material being tested) may be subjected to repeated object drops from that maximum height. These test procedures may be the same where the layered-substrate, substrate or other material is included in a device or article, which is then subjected to the test in the same manner as the layered-substrate, substrate and/or other component.

In one or more embodiments, at least about 60% of the samples survive the drop tests described herein. In other embodiments, at least about 65%, at least about 70%, at least about 75%, at least about 80%, at least about 85%, or at least about 90% of the samples survive the drop tests described herein. In such embodiments, the layered substrate 10 is characterized as having at least a 60% survivability (or at least a 65% survivability, at least a 70% survivability, at least a 75% survivability, at least a 80% survivability, at least a 85% survivability, or at least a 90% survivability).

In one or more embodiments, the improved scratch resistance is exhibited by the layered-substrates 10 herein, regardless of the underlying substrate 100 utilized. Moreover, the fracture resistance of the layered-substrate 10 was also observed where the substrate included strengthened glass or glass that is not strengthened. The fracture resistance of the layered-substrate 10 may be observed whether the substrate includes a crystalline substrate and/or an amorphous substrate (including or excluding glass). Such improvements indicate that the layer 200 plays a role in preventing flaws present in the layer 200 (e.g., by deposition conditions or process or other cause) or introduced into the layer (e.g., by the impact between the layered-substrate 10 and the drop surface) from being introduced or penetrating into the substrate 100.

In one or more embodiments, the strength of the substrate 100, especially where the substrate includes a glass substrate, plays a role in the level of fracture resistance. As noted above, even glass substrates that are not strengthened and which are combined with the layer 200, exhibited improved fracture resistance in drop tests; however, the combination of a strengthened substrate with the layer 200 demonstrated an even greater improvement in fracture resistance in drop tests (over bare glass substrates and/or substrates that are not strengthened but are combined with a layer 200). In one or more embodiments, materials including glass substrates with a deep depth of layer (e.g., >50 μm) and/or is strengthened such that there is some CS at a specific DOC, demonstrate even greater fracture resistance in drop tests.

In one or more embodiments, the layered-substrate 10 exhibits an average transmittance of 70% or greater, 75% or greater, 80% or greater, 85% or greater, or 90% or greater, determined over the visible range (e.g., 380 nm-780 nm). In some specific embodiments, the layered-substrate 10 exhibits an average transmittance of about 90.5% or greater, 91% or greater, 91.5% or greater, 92% or greater, 92.5% or greater, 93% or greater, 93.5% or greater, 94% or greater, 94.5% or greater, or 95% or greater. In some variants, the layered-substrate 10 is substantially opaque and/or may exhibit an average transmittance of about 10% or less, over the visible range (e.g., 380 nm-780 nm). For example, the average transmittance may be about 9% or less, about 8% or less, about 7% or less, about 6% or less, about 5% or less, about 4% or less, about 3% or less, about 2% or less, about 1% or less or even 0%, and all ranges and sub-ranges therebetween.

In one or more embodiments, the layered-substrate 10 has an average total reflectivity that 10% or less, over the visible range (e.g., 380 nm-780 nm). For example, the layered-substrate 10 may have a total reflectivity of 9% or less, 8% or less, 7% or less, 6% or less. In some specific embodiments, the layered-substrate 10 exhibits an average total reflectivity of 6.9% or less, 6.8% or less, 6.7% or less, 6.6% or less, 6.5% or less, 6.4% or less, 6.3% or less, 6.2% or less, 6.1% or less, 6.0% or less, 5.9% or less, 5.8% or less, 5.7% or less, 5.6% or less, 5.5%, or less. In accordance with one or more embodiments, the layered-substrate 10 has a total reflectivity that is the same or less than the total reflectivity of the substrate 100.

The layered-substrate 10 may include one or more functional layer(s) disposed on the layer 200 or on the opposite surface of the substrate 100 from the layer 200 (e.g., on the second opposing major surface 112, shown in FIG. 1). Such functional layer(s) may include an IR blocking layer, a UV blocking layer, a conducting layer, a semiconducting layer, an electronics layer, a thin-film-transistor layer, a touch-sensing layer, an image-display layer, a fluorescent layer, a phosphorescent layer, a light-emitting layer, a wavelength-selective reflecting layer, a heads-up display layer, an anti-reflection layer, an anti-glare layer, a dirt-resistant layer, a self-cleaning layer, a barrier layer, a passivation layer, a hermetic layer, a diffusion-blocking layer, a fingerprint resistant layer or combinations thereof.

A second aspect of this disclosure pertains to devices and/or articles that include the layered-substrates 10 described herein. The layered-substrate 10 may be used as part or all of the housing of a device and/or articles. The layered-substrate 10 may also be used as the cover for a display included in a device and/or articles. Exemplary devices include electronic devices (e.g., mobile phones, smart phones, tablets, video players, information terminal devices, laptop computer, etc.), architectural structures (e.g., countertops or walls), appliances (e.g., cooktops, refrigerator and dishwasher doors, etc.), information displays (e.g., whiteboards), automotive components (e.g., dashboard panels, windshields, window components, etc.) and the like.

Another aspect of this disclosure pertains to a method for forming an article and/or device, as described herein. In one or more embodiments, the method includes providing a substrate, as described herein, comprising opposing major surfaces and disposing a layer 200 on a first opposing major surface to form a layered-substrate that is able to withstand fracture when assembled with the article and/or device and the device is in a drop test from a height of at least 100 cm onto a drop surface or is subjected to a test in which an object is dropped onto the layered-substrate at a height of at least 100 cm. The method also includes assembling the layered-substrate with the device. In one or more embodiments, the method includes disposing the layer by atomic layer deposition, chemical vapor deposition, physical vapor deposition, thermal evaporation or a combination thereof. In some embodiments, the method includes disposing the layer by methods other than atomic layer deposition. In one or more specific embodiments, the resulting layer is not as conformal as layers formed by atomic layer deposition.

EXAMPLES

Various embodiments will be further clarified by the following examples.

Example 1

Examples A and B, and Comparative Examples C and D were prepared, as shown in Table 1. Five samples were made according to Example A by providing five strengthened glass substrates each having a thickness of 1 mm, a length of 110 mm and a width of 56 mm. The glass substrates included an aluminoborosilicate glass having a composition that includes at least about 50 mol % $SiO_2$, from about 12 mol % to about 22 mol % $Al_2O_3$; from about 4.5 mol % to about 10 mol % $B_2O_3$; from about 10 mol % to about 20 mol % $Na_2O$; from 0 mol % to about 5 mol % $K_2O$; at least about 0.1 mol % MgO, ZnO, or combinations thereof, wherein 0 mol %≤MgO≤6 and 0≤ZnO≤6 mol %. The glass substrates were strengthened to exhibit a CS of at least about 700 MPa and a DOL of at least about 40 μm using an ion-exchange process in which the glass substrates were immersed in a molten potassium nitrate ($KNO_3$) bath that was heated to a temperature in the range from about 350° C. to 450° C. for a duration of 3-8 hours. A $Si_3N_4$ layer was deposited onto one side of each of the glass substrates via ion assist DC sputtering process using a DC Magnetron system. The layer was sputtered from a target at a pressure of about 0.5 mTorr and temperature of about 109.6° C. in the presence of argon flowed at a rate of about 60 sccm, with DC power supplied at 2.1 kW. The ion beam was generated at a power of 0.2 kW using a 100 sccm of nitrogen. The resulting $Si_3N_4$ layer on the samples of Example A had a thickness of about 2 μm.

Ten samples were made according to Example B by providing ten glass substrates having the same composition and dimensions as the substrates of Example A. The glass substrates were not strengthened. A $Si_3N_4$ layer identical to the layer utilized in the samples of Example A was formed on one side of each of the glass substrates of Example B in the same manner as Example A. The resulting $Si_3N_4$ layer on the samples of Example B had a thickness of about 2 μm.

Ten samples were made according to Comparative Example C by providing ten glass substrates identical in composition, dimensions, CS and DOL as the glass substrates of Example A. The glass substrates used for the samples of Comparative Example C were not combined with any layer or coating.

One sample was made according to Comparative Example D by providing a glass substrate having the same composition and dimensions as the substrates of Example A. The glass substrate was not strengthened or combined with any layer or coating.

TABLE 1

Examples A and B and Comparative Examples C and D

|  | Example A | Example B | Comparative Example C | Comparative Example D |
|---|---|---|---|---|
| Substrate | Strengthened glass | Not strengthened glass | Strengthened glass | Not strengthened glass |
| Layer | $Si_3N_4$ | $Si_3N_4$ | None | None |

Figure 9:
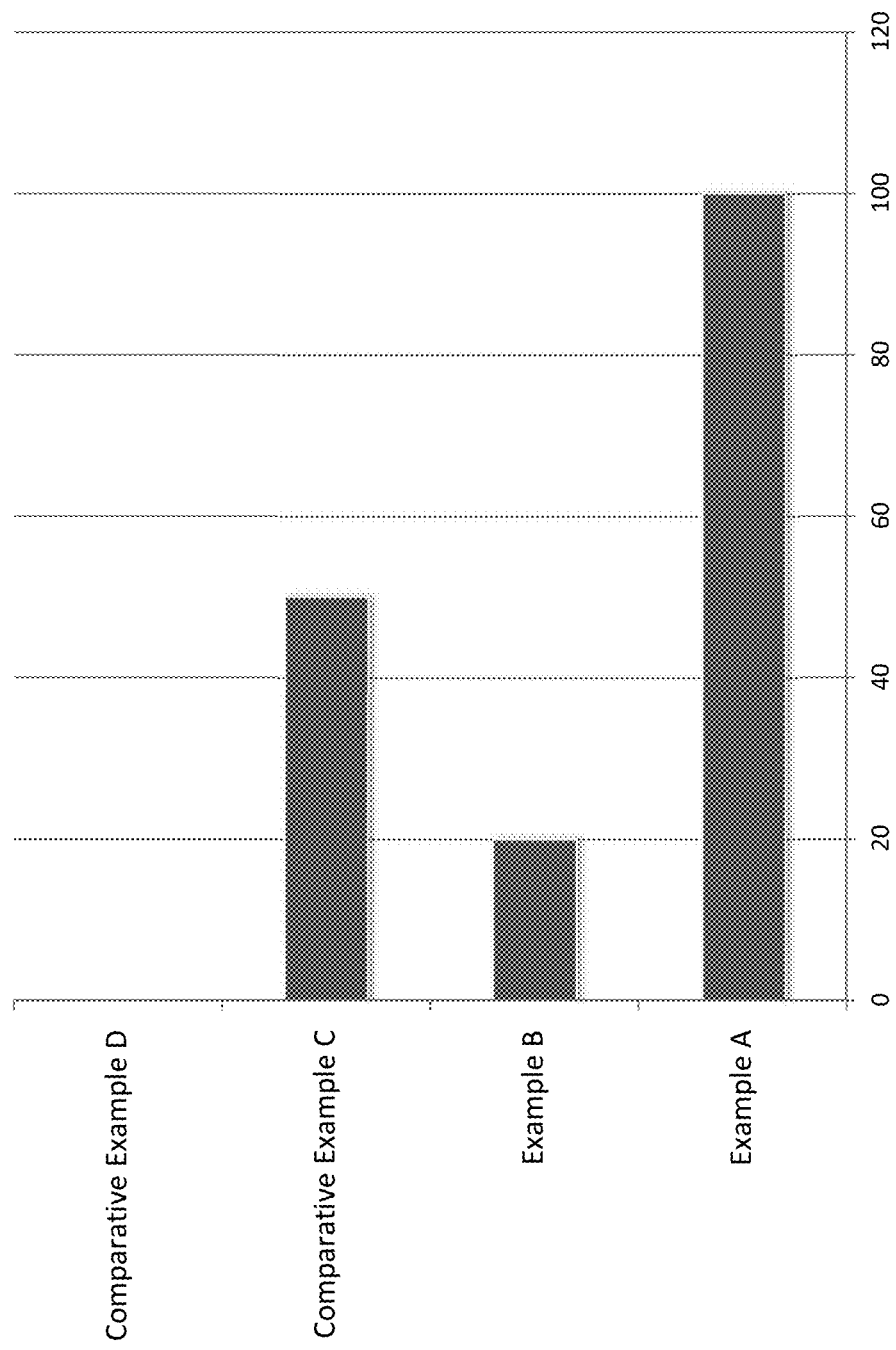
FIG. 9 shows the drop test performance of layered-substrates according to one or more embodiments and known substrates.

Each of the samples according to Example A, Example B, Comparative Example C and Comparative Example D were assembled in a mobile phone. The mobile phones were tested using the drop test using an asphalt drop surface. FIG. 9 illustrates the percentage of samples that survived the drop test (along the x-axis) after each mobile phone sample was dropped from a height of 1 meter, using different orientations or positions, including at least one orientation where the layered-substrate or substrate contacted the drop surface.

Comparative Example D failed when dropped on the asphalt drop surface as provided above. Half of the samples of Comparative Example C failed when dropped on an asphalt drop surface. Twenty percent of the samples of Example B survived when dropped on the asphalt surface. All of the samples according to Example A survived being dropped on asphalt drop surface.

Example 2

Example E was prepared into nine samples, eight of which were abraded, as indicated below, using Berkeley Sand and SiC particles. The nine samples were prepared by providing nine strengthened glass substrates each having a thickness of 1 mm, a length of 50 mm and width of 50 mm. The glass substrates utilized had the same composition as Example 1 and were strengthened in the same manner as the glass substrates of Example 1 and exhibited the same CS and DOL. A $Si_3N_4$ layer was formed on one side of each of the glass substrates via DC sputtering process using a DC Magnetron system. The layer was sputtered from a target at a pressure of about $6.9 \times 10^{-4}$ Torr in the presence of argon flowed at a rate of about 75 sccm, with DC power supplied at 4 kW. The ion beam was generated at a power of 0.310 kW in the presence of nitrogen flowed at 115 sccm. The deposition rate was 1.4 Å/second and the total deposition time was 230 minutes. The resulting $Si_3N_4$ layer had a thickness of about 2 μm.

The average flexural strength of the sample 1 of Example E was measured using ring-on-ring strength testing without being abraded to provide a baseline average flexural strength. Samples 2-9 of Example E were abraded and then subjected to ring-on-ring strength testing, as shown in Table 2. The ring-on-ring strength testing procedures used are disclosed in this disclosure. Berkeley Sand was used to abrade samples 2-5 and was sourced from Berkeley Springs, W. Va. by U.S. Silica and was screened to 70-100 mesh. Samples 6-9 were abraded using 90-grit SiC particles available under the tradename Carborex C-6, from Washington Mills, in Niagara Falls, N.Y.

TABLE 2

Abraded strength using Berkeley Sand and SiC particles Example E

| Sample | Abrasion Pressure (psi) | Abrasive Material | Volume of Abrasive Material |
|---|---|---|---|
| 1 | Not abraded (indicated by 0 psi in FIG. 10) | None |  |
| 2 | 1 | Berkeley Sand | 1 milliliters |
| 3 | 2 | Berkeley Sand | 1 milliliters |
| 4 | 3 | Berkeley Sand | 1 milliliters |
| 5 | 4 | Berkeley Sand | 1 milliliters |
| 6 | 1 | SiC particles | 1 milliliters |
| 7 | 2 | SiC particles | 1 milliliters |
| 8 | 3 | SiC particles | 1 milliliters |
| 9 | 4 | SiC particles | 1 milliliters |

Figure 10:
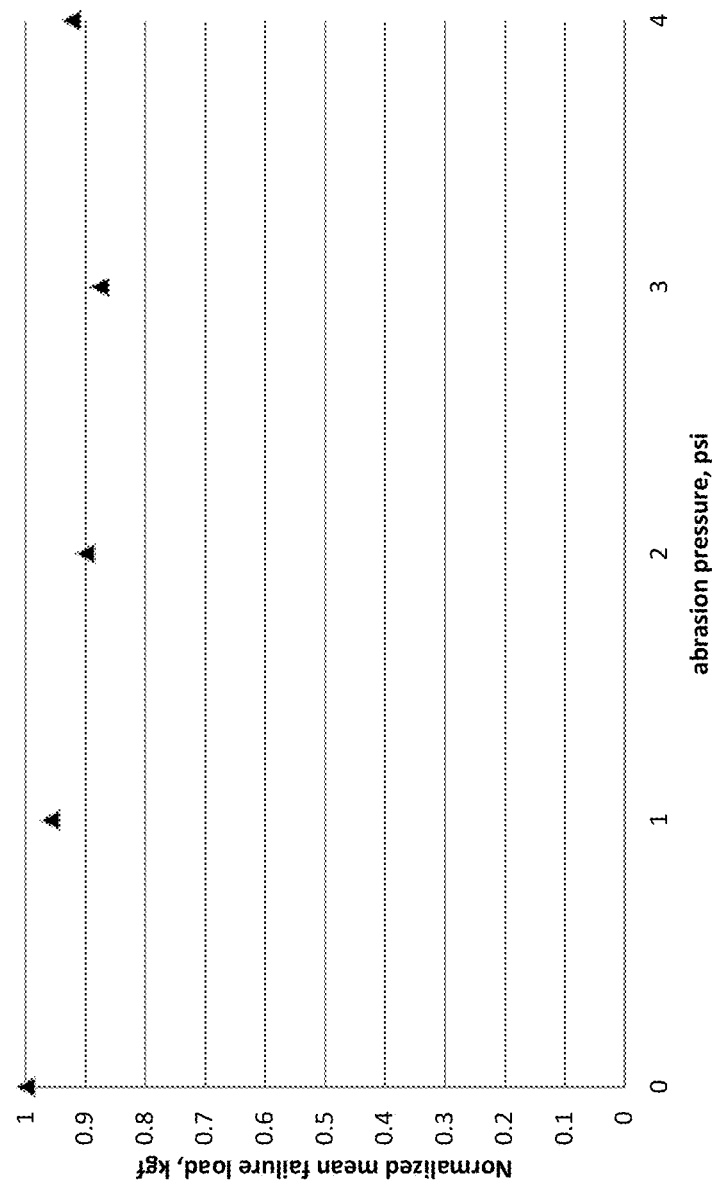
FIG. 10 illustrates the abraded strength of layered-substrates according to one or more embodiments and the abraded strength of known substrates.
Figure 11:
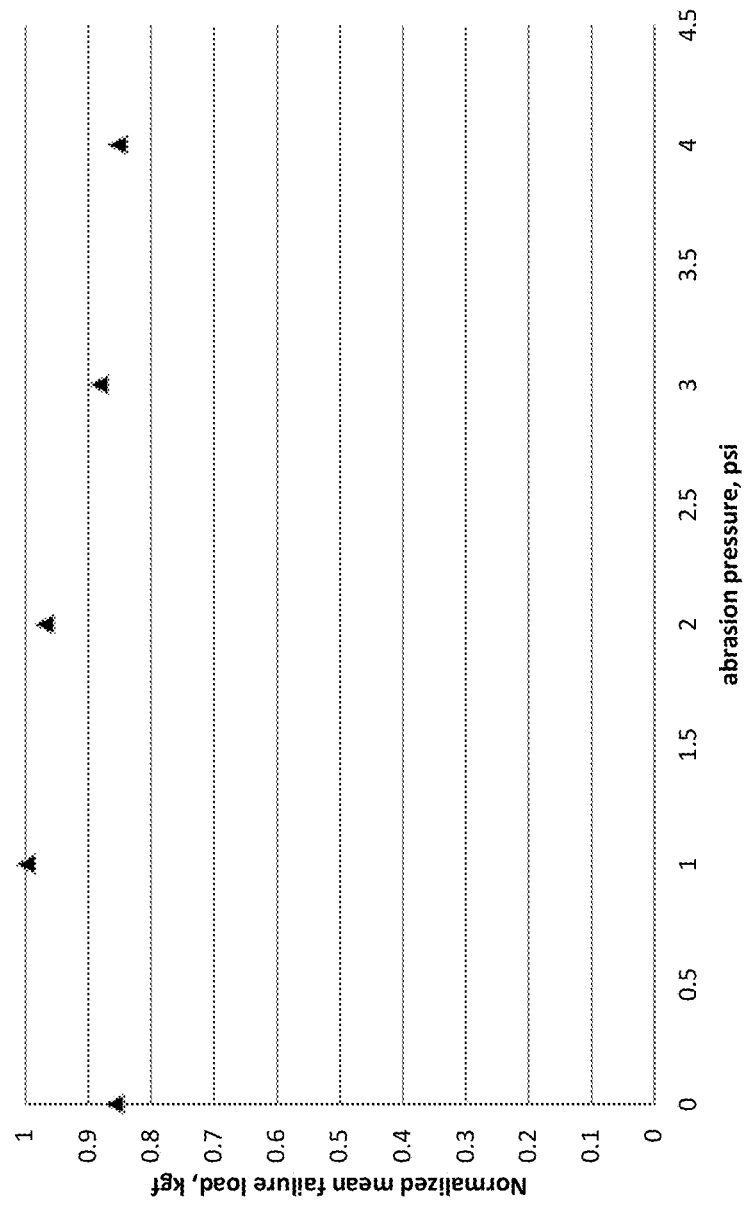
FIG. 11 illustrates the abraded strength of layered-substrates according to one or more embodiments and the abraded strength of known substrates.

FIG. 10 illustrates the average flexural strength of samples 1-5 of Example E. FIG. 11 illustrates the average flexural strength of samples 1 and 6-9 of Example E. For both FIGS. 10 and 11, the mean failure load (kgf) has been normalized to the sample 1 (the non-abraded sample). In other words, the mean failure load of each of the abraded samples (e.g., samples 2-9) was divided by the mean failure load of sample 1 (the non-abraded sample). The normalized plots shown in FIGS. 10 and 11 illustrate the relative change in the mean failure load when the samples are not abraded and then abraded using different abrasives and abrasion pressures. FIGS. 10 and 11 also illustrate the percentage of strength that is maintained after the samples are subjected to abrading using different abrasives and abrasion pressures. As shown in FIG. 10 and FIG. 11, the average flexural strength of the samples according to Example E was substantially the same before and after being abraded.

Example 3

Three samples each of Example F and Comparative Example G were prepared to illustrate improved scratch resistance of the layered-substrates disclosed herein in terms of exhibiting shallower scratch depths and narrower scratch widths, when compared to bare substrates.

Four samples each of Example F were prepared by providing three chemically strengthened glass substrates each having opposing major surfaces and forming a layer comprising SiOxNy on one major surface of each sample. The glass substrates included a composition identical to the glass substrates used in Examples 1 and 2 and were chemically strengthened to exhibit a CS of at least about 700 MPa and a DOL of at least about 40 μm. The glass substrates had a thickness of about 1 mm, a length of about 50 mm and a width of about 50 mm. The SiOxNy layer had a thickness of about 2 μm and was deposited via ion assist DC sputtering process using a DC Magnetron system using the same conditions used to form the SiOxNy layer of Example 2. Four samples each of Comparative Example G were prepared by providing three chemically strengthened glass substrates having the same composition, dimensions, compressive stress and compressive stress layer thicknesses (DOL) as the glass substrates utilized in the samples of Example F. Each of the samples of Example F and Comparative Example G were scratched at four different loads using a diamond Berkovich indenter at a speed of 10 μm/second for a length of at least 100 μm or at least about 1 mm along the surface of the sample. For the samples of Example F, the side of the glass substrate including the layer was scratched. The width and depth of the scratch on each of the samples were measured and are provided in Table 3.

TABLE 3

Scratch loads and width and depth measurements of layered-substrates including a SiOxNy layer.

| Sample # | | Width (μm) | Depth (nm) | Width Reduction | Depth Reduction |
|---|---|---|---|---|---|
| Example F | 1 (160 mN load) | 6.67 | 270 | 37% | 40% |
| Comparative Example G | 1 (160 mN load) | 10.61 | 451 | | |
| Example F | 2 (120 mN load) | 5.46 | 218 | 39% | 42% |
| Comparative Example G | 2 (120 mN load) | 9.00 | 374 | | |
| Example F | 3 (60 mN load) | 3.81 | 130 | 31% | 40% |
| Comparative Example G | 3 (60 mN load) | 5.56 | 216 | | |
| Example F | 4 (30 mN load) | 2.72 | 83 | 34% | 39% |
| Comparative Example G | 4 (30 mN load) | 4.15 | 135 | | |

TABLE 4

Scratch loads and width and depth measurements of layered-substrates including an AlN layer.

| Sample | | Width (μm) | Depth (nm) | Width Reduction | Depth Reduction |
|---|---|---|---|---|---|
| Example H | 1 (160 mN load) | 4.42 | 145 | 12% | 23% |
| Comparative Example I | 1 (160 mN load) | 5.05 | 189 | | |
| Example H | 2 (120 mN load) | 3.71 | 130 | 22% | 20% |
| Comparative Example I | 2 (120 mN load) | 4.74 | 163 | | |
| Example H | 3 (60 mN load) | 2.45 | 65 | 26% | 40% |
| Comparative Example I | 3 (60 mN load) | 3.32 | 108 | | |
| Example H | 3 (30 mN load) | 0.95 | 33 | 57% | 45% |
| Comparative Example I | 3 (30 mN load) | 2.21 | 60 | | |

Example 4

Four samples were prepared according Example H and Comparative Example I to illustrate improved scratch resistance of the layered-substrates disclosed herein in terms of exhibiting shallower scratch depths and narrower scratch widths, when compared to bare substrates.

Four samples each of Example H were prepared by providing four chemically strengthened glass substrates each having opposing major surfaces and forming a layer comprising MN on one major surface of each sample. The glass substrates included a composition identical to the glass substrates used in Examples 1 and 2 and were chemically strengthened to exhibit a CS of at least about 700 MPa and a DOL of at least about 40 μm. The glass substrates had a thickness of about 1 mm, a length of about 50 mm and a width of about 50 mm. The MN layer disposed on each of the glass substrates had a thickness of about 2 μm and was deposited via ion assist DC sputtering process using a DC Magnetron system. The MN layer was sputtered from a target at a pressure of about $5.88 \times 10^{-4}$ Torr and temperature of about 160° C. in the presence of argon flowed at a rate of about 74.91 sccm, with DC power supplied at 3.9 kW. The ion beam was generated at a power of 0.224 kW in the presence of nitrogen and argon flowed at 98.84 sccm and 24.66 sccm, respectively. The deposition rate was 1.4 Å/second and the total deposition time was 113 minutes. The resulting MN layer on the samples of Example H had a thickness of about 1.175 μm.

Four samples each of Comparative Example I were prepared by providing four chemically strengthened glass substrates having the same composition, dimensions, compressive stress and compressive stress layer thicknesses as the glass substrates utilized in the samples of Example H. Each of the samples of Example H and Comparative Example I were scratched at four different loads using a diamond Berkovich indenter at a speed of 10 μm/second for a length of at least 100 μm or at least about 1 mm along the surface of the sample. For the samples of Example H, the side of the glass substrate including the MN layer was scratched. The width and depth of the scratch on each of the samples were measured and are provided in Table 4.

Example 5

Examples J and K were prepared to illustrate improved mechanical properties (e.g., scratch depth reduction) and associated optical properties (e.g., colorless transmittance and/or reflectance) of the layered-substrates disclosed herein. The results are shown in Table 5 and Table 6.

Two samples according to Example J were prepared and included a glass substrate with a layer comprising AlN having a thickness of about 2 μm (Example J1) and a layer comprising SiOxNy having a thickness of about 2 μm (Example J2), as shown below in Table 5. The substrates used to form the two samples were identical to the substrates used in Examples 1 and 2. The substrates had a length and width of 2"×2" and included a thickness of about 1 mm.

Example J1 was prepared by depositing the AlN layer via ion assist DC sputtering process using a DC Magnetron system. The AlN layer was sputtered from a target at a pressure of 1.7 mTorr in the presence of argon flowed at a rate of about 100 sccm, with DC power supplied at about 4 kW. The ion beam was generated at a power in the range from about 0.434 kW to about 0.345 kW using a mixture of argon and nitrogen gases flowed at a rate of about 50 sccm and 75 sccm, respectively. The deposition time was 120 minutes and the deposition rate was about 3 Å/second.

The sample according to Example J2 including a SiOxNy layer was prepared by depositing the layer via ion assist DC sputtering process using a DC Magnetron system. The SiOxNy layer was sputtered from a target at a pressure of about 0.5 mTorr in the presence of argon flowed at a rate of about 60 sccm, with DC power supplied at 6 kW. The ion beam was generated at a power of 0.18 kW using a mixture of nitrogen and oxygen gases.

One sample each of Examples K1 and K2 were prepared and utilized substrates identical to the substrates used in Examples 1 and 2 (having a length and width of 2"×2" and thickness of about 1 mm). The substrate of Example K1 was then combined with an AlOxNy layer, a first additional layer of $Al_2O_3$ disposed between the AlOxNy layer and the substrate and a second additional layer of $SiO_2$ disposed on the AlOxNy layer. The $Al_2O_3$ additional layer was formed via ion assist DC sputtering process using a DC Magnetron system. The $Al_2O_3$ additional layer was sputtered from a target at a pressure of 0.4 mTorr in the presence of argon flowed at a rate of about 50 sccm, with DC power supplied at about 4 kW; an ion beam was generated at a power of about 0.6 kW using a mixture of argon (flowed at a rate of about 10 sccm) and oxygen (flowed at a rate of about 40 sccm). The deposition rate for the $Al_2O_3$ layer was about 3 Å/second and the resulting thickness was 300 nm. The AlOxNy layer was formed on the $Al_2O_3$ additional layer via ion assist DC sputtering process using a DC Magnetron system. The AlOxNy layer was sputtered from a target at a pressure of about 0.95 mTorr in the presence of argon flowed at a rate of about 75 sccm, with DC power supplied at about 4 kW; an ion beam was generated at a power of about 0.18 kW using a mixture of argon (flowed at a rate of about 25 sccm), oxygen (flowed at a rate of about 2 sccm) and nitrogen (flowed at a rate of about 50 sccm). The deposition rate for the AlOxNy layer was 1.6 Å/seconds and the resulting layer had a thickness of about 2 μm. The SiO2 additional layer was formed by e-beam using a power of about 0.8 kW in the presence of argon and oxygen, flowed at a rate of 30 sccm and 15 sccm, respectively. The deposition rate for the SiO2 additional layer was 5 Å/second and the thickness was 83 nm.

The substrate of example K2 was combined with a SiOxNy layer formed via ion assist DC sputtering process using DC Magnetron. The SiOxNy layer formed in 14 sequential deposition cycle, with each cycle separated by a cleaning step using an ion beam generated at a pressure of about 0.76 mTorr in the presence of argon (flowed at 40 sccm) and nitrogen (flowed at 20 sccm). The first deposition cycle included sputtering the SiOxNy layer from a target at a pressure of about 0.86 mTorr in the presence of argon flowed at a rate of about 75 sccm, with DC power supplied at about 4 kW; an ion beam was generated in the presence of oxygen (flowed at a rate of about 10 sccm) and nitrogen (flowed at a rate of about 115 sccm). The first deposition cycle had a deposition rate of about 1.4 Å/second and a total deposition time of 10 minutes. The next ten deposition cycles included sputtering the SiOxNy layer from a target at a pressure in the range from about 0.75 mTorr to about 8.88 mTorr in the presence of argon flowed at a rate of about 75 sccm, with DC power supplied at about 4 kW; an ion beam was generated in the presence of oxygen (flowed at a rate of about 5 sccm) and nitrogen (flowed at a rate of about 115 sccm). These ten deposition cycles had a deposition rate of about 1.3 Å/second and a deposition time of 28 minutes for each cycle. The twelfth and fourteenth deposition cycles included sputtering the SiOxNy layer from a target at pressures of about 0.84 mTorr and 0.82 mTorr, respectively, in the presence of argon flowed at a rate of about 75 sccm, with DC power supplied at about 4 kW; an ion beam was generated in the presence of oxygen (flowed at a rate of about 2 sccm) and nitrogen (flowed at a rate of about 115 sccm). The twelfth and fourteenth deposition cycles each had a deposition rate of about 1.3 Å/second and a deposition time of 21 minutes and 4 minutes, respectively. The thirteenth deposition cycle included sputtering the SiOxNy layer from a target at a pressure of about 0.68 mTorr in the presence of argon flowed at a rate of about 60 sccm, with DC power supplied at about 4 kW; an ion beam was generated in the presence of oxygen (flowed at a rate of about 100 sccm). The thirteenth deposition cycle had a deposition rate of about 0.5 Å/second and a total deposition time of 10 minutes. The resulting SiOxNy layer had at thickness of about 2.434 μm.

TABLE 5

Mechanical Properties of Example J.

| Example J | Example J1 - Layer: AlN Berkovich indenter load of 160 mN resulted in a 28% reduction in scratch depth, as compared to a bare substrate Berkovich indenter force of 60 mN resulted in a 35% reduction in scratch depth, as compared to a bare substrate | Example J2 - Layer: SiOxNy Berkovich indenter load of 160 mN resulted in a 35% reduction in depth, as compared to a bare substrate Berkovich indenter force of 60 mN resulted in a 63% reduction in scratch depth, as compared to a bare substrate |
|---|---|---|

TABLE 6

Mechanical and Optical Properties of Example K.

| Example K | Example K1 - Layer: AlOxNy; additional layer $Al_2O_3$ disposed between the substrate and the AlOxNy layer and additional layer $SiO_2$ disposed on the AlOxNy layer. Berkovich indenter load of 160 mN resulted in a 28% reduction in scratch depth, as compared to a bare substrate Berkovich indenter load of 60 mN resulted in a 46% reduction in scratch depth, as compared to a bare substrate CIELAB color coordinates (in transmittance): L* 96.4, A*0.079, B* 0.0071 CIELAB color coordinates (in reflectance): L* 42.8, A*0.203, B*0.70 | Example K2 - Layer: SiOxNy Berkovich indenter load of 160 mN resulted in a 48% reduction in scratch depth, as compared to a bare substrate. Berkovich indenter load of 60 mN resulted in a 65% reduction in scratch depth, as compared to a bare substrate CIELAB color coordinates (in transmittance): L* 95.2, A* 0.20, B* 2.82 CIELAB color coordinates (in reflectance): L* 36.0, A* −0.87, B* −3.82 |
|---|---|---|

With respect to the scratch depth reduction measurements shown in Table 5 and Table 6, the reduction in scratch depth exhibited by the samples according to Examples J and K are as compared to bare substrates. It will be understood that the bare substrates are identical to the substrates used to prepare the samples according to Examples J and K; however these comparative bare substrates do not include a layer. In addition, these comparative bare substrates were scratched in an identical manner as the samples according to Examples J and K to provide a baseline measurement against which the scratches formed on the samples according to Examples J and K were compared. The reduction in scratch depth was calculated using the baseline scratch depth measurements obtained for the bare substrates and the scratch depth measurements obtained for the samples according to Examples J and K.

The CIELAB color space coordinates shown in Table 6 were determined from specular reflectance measurements using a spectrophotometer, with illuminant D65.

Example 6

One hundred forty-three (143) samples of mobile phones were prepared to determine the fracture resistance of various substrates and layered-substrates, when assembled in a mobile phone. Table 7 describes the attributes of each sample.

Ten of the 143 total samples (Comparative Examples L1-L10) were commercially available mobile phones with no modifications made to the mobile phones.

Thirty-three of the mobile phone samples (Examples M1-M33) were commercially available mobile phones that were identical to Comparative Examples L1-L10 but the cover glass of each of mobile phones was replaced or retrofitted with a glass substrate that included a glass composition including about 60.1 mol % $SiO_2$, about 15.6 mol % $Al_2O_3$, about 16 mol % $Na_2O$, about 3 mol % MgO, about 5.1 mol % $P_2O_5$ and about 0.1 mol % $SnO_2$. The glass substrate had a length and width dimensions of 110 mm and 56 mm, respectively, and a thickness of about 1 mm. Each of the glass substrates retrofitted into the mobile phones of Examples M1-M33 was chemically strengthened prior to assembly in the mobile phones and exhibited a CS of about 900 MPa and a DOL in the range from about 40 μm to about 45 μm.

Fifteen mobile phone samples (Examples N1-N15) were prepared by providing fifteen glass substrates identical to the glass substrates used in Examples M1-M33 with respect to composition, size, CS and DOL. The fifteen glass substrates of Examples N1-N15 were coated with a silicon nitride layer having a thickness of 100 nm to form fifteen glass layered-substrates. The $Si_3N_4$ layer was deposited onto one side of each of the glass substrates of Examples N1-N15 via ion assist DC sputtering process using a DC Magnetron system. The layer was sputtered from a target at a pressure of about $5.73×10^{-4}$ Torr and temperature of about 99.9° C. in the presence of argon flowed at a rate of about 59.92 sccm, with DC power supplied at 2.04 kW. The ion beam was generated at a power of 0.186 kW using a 98.81 sccm of nitrogen. The fifteen glass layered-substrates were retrofitted into fifteen mobile phones that were identical to the mobile phones of Comparative Examples L1-L10.

Fifty-eight mobile phone samples (Examples O1-O58) were prepared by providing fifty-eight glass substrates identical in composition and size to the glass substrates used in Examples M1-M33. These glass substrates were combined with a layer and optionally additional layer(s) as provided in Table 7 to form layered-substrates that were each retrofitted in a mobile phone identical to the mobile phones of Comparative Examples L1-L10.

Fifteen glass substrates (utilized in Examples O1-O15) were chemically strengthened in the same manner as Examples M1-M33 and exhibited a CS of about 900 MPa and a DOL in the range from about 40 μm to about 45 μm. Examples O1-O15 were combined with a single AlOxNy layer. The AlOxNy layer was deposited onto one side of each of the glass substrates via ion assist DC sputtering process using a DC Magnetron system. The layer was sputtered from a target at a pressure of about $7.4×10^{-4}$ Torr and temperature of 200° C. in the presence of argon flowed at a rate of about 75 sccm, with DC power supplied at 4 kW. The ion beam was generated at a power of 0.15 kW in the presence of oxygen, argon and nitrogen flowed at a rate of 2 sccm, 25 sccm and 50 sccm respectively. The deposition rate was 1.3 Å/second and the deposition time was 275 minutes. The AlOxNy layer had a thickness of about 2 microns.

Fifteen glass substrates (utilized in Examples O16-O30) were chemically strengthened in a $KNO_3$ bath having a concentration of Na+ ions of about 29 wt % for 27 hours at 450° to provide a CS of 375 MPa and a DOL of about 100 μm. Examples O16-O30 were combined with a single AlON layer formed on the glass substrates using the same process as Examples O1-O15. The resulting AlOxNy layer had a thickness of about 2 microns.

Nine of the glass substrates (utilized in Examples O03-O39) were chemically strengthened in the same manner as Examples O16-O30, however thereafter, the glass substrates were immersed in a second bath to provide a CS of about 375 MPa, a DOL of about 75 μm and a spike in CS at the surface of the glass substrates. Each of the glass substrates used in Examples O31-O39 were combined with a layer of AlOxNy, a first additional layer of $Al_2O_3$ disposed between the AlOxNy layer and the glass substrate and a second additional layer of $SiO_2$ disposed on the AlOxNy layer. The layer, the first additional layer of $Al_2O_3$ and the second additional layer of $SiO_2$ were formed on one side of each of the glass substrates via ion assist DC sputtering process using a DC Magnetron system. The first additional layer was sputtered at a pressure of $6.5×10^{-4}$ Torr and temperature of 200° C. in the presence of argon flowed at a rate of about 75 sccm, with DC power supplied at 4 kW. The ion beam was generated at a power of 0.155 kW in the presence of argon and oxygen flowed at a rate of 20 sccm and 40 sccm respectively. The deposition rate was 3 Å/second and the deposition time was 8 minutes. The $Al_2O_3$ layer had a thickness of 88.7 nm. The AlOxNy layer was sputtered at a pressure of $7.6×10^{-4}$ Torr and temperature of 200° C. in the presence of argon flowed at a rate of about 75 sccm, with DC power supplied at 4 kW. The ion beam was generated at a power of 0.180 kW in the presence of argon, oxygen and nitrogen flowed at a rate of 25 sccm, 4 sccm, and 50 sccm respectively. The deposition rate was 1.5 Å/second and the deposition time was 217 minutes. The AlOxNy layer had a thickness of about 2 microns. The second additional layer of $SiO_2$ was formed by e-beam using a power of about 0.8 kW in the presence of argon and oxygen, flowed at a rate of 30 sccm and 15 sccm, respectively. The deposition rate for the $SiO_2$ additional layer was 5 Å/second, the deposition time was 3 minutes and the thickness was 33 nm.

Nine of the glass substrates (utilized in Examples O40-O48) were chemically strengthened in the same manner as Examples O03-O39; however the duration the ion exchange process(es) and/or composition of the bath was modified to provide a CS of about 375 MPa, a DOL of about 125 μm and a spike in CS at the surface of the glass substrates. The glass substrates were then combined with a layer of AlOxNy, a first additional layer of $Al_2O_3$ disposed between the AlOxNy layer and the glass substrate and a second additional layer of $SiO_2$ disposed on the AlOxNy layer. The AlOxNy layer, the first additional layer and the second additional layer were formed on each glass substrate using the same conditions as Examples O31-O39. The resulting thicknesses of the layer, the first additional layer and the second additional layer were also the same as Examples O31-O39.

Ten glass substrates (utilized in Examples O49-O58) were identical in composition, CS and DOL as Examples O1-O15. Each of the glass substrates used in Examples O49-O58 were combined with a layer of AlOxNy, a first additional layer of $Al_2O_3$ disposed between the AlOxNy layer and the glass substrate and a second additional layer of $SiO_2$ disposed on the AlOxNy layer. The layer, the first additional layer and the second additional layer were formed on one side of each of the glass substrates via ion assist DC sputtering process using a DC Magnetron system. The first additional layer was sputtered at a pressure of $7.5 \times 10^{-4}$ Torr and temperature of 200° C. in the presence of argon flowed at a rate of about 75 sccm, with DC power supplied at 4 kW. The ion beam was generated at a power of 0.2 kW in the presence of argon and oxygen flowed at a rate of 20 sccm and 40 sccm respectively. The deposition rate was 2.5 Å/second and the deposition time was 8 minutes. The $Al_2O_3$ layer had a thickness of 88.6 nm. The AlOxNy layer was sputtered at a pressure of $7.5 \times 10^{-4}$ Torr and temperature of 200° C. in the presence of argon flowed at a rate of about 75 sccm, with DC power supplied at 4 kW. The ion beam was generated at a power of 0.180 kW in the presence of argon, oxygen and nitrogen flowed at a rate of 25 sccm, 4 sccm, and 50 sccm respectively. The deposition rate was 1.6 Å/second. The AlOxNy layer had a thickness of about 2 microns. The second additional layer of $SiO_2$ was formed by e-beam using a power of about 0.8 kW in the presence of argon and oxygen, flowed at a rate of 30 sccm and 15 sccm, respectively. The deposition rate for the $SiO_2$ additional layer was 5 Å/second, the deposition time was 3 minutes, and the thickness was 33 nm.

Twenty-seven mobile phone samples (Examples P1-P27) were prepared by providing glass substrates identical in composition, size, CS and DOL as Examples O16-O30). The glass substrates were not combined with a layer or additional layer. Each of the glass substrates was retrofitted in a mobile phone identical to the mobile phones of Comparative Examples L1-L10.

Each of the mobile phone samples of Examples L, M, N, O and P were then dropped at different orientations from a height of 1 m onto an asphalt drop surface. Table 8 includes the percent of samples surviving including and excluding samples experiencing edge failure. The percent of samples surviving including samples experiencing edge failure ("survival % (including samples that experienced edge failure)") included mobile phone samples in which the glass substrate or layered-substrate (including a glass substrate, layer and, optionally, additional layer(s)) experienced any type of fracture. The percent of samples surviving excluding samples experiencing edge failure ("survival % excluding samples that experienced edge failure") was calculating by excluding the number of samples that experienced edge failure were excluded from 1) the total number of samples tested, and 2) the number of samples that survived, because failure at an edge was not attributed to the fracture resistance of the glass substrate or layered-substrate (including a glass substrate, layer and, optionally, additional layer(s)). Accordingly, the survival % excluding samples experiencing edge failure indicates the number of mobile phone samples that experienced no fracture on the major surface of the glass substrate or layered-substrate (including a glass substrate, layer and, optionally, additional layer(s)), from a population that also excluded mobile phone samples that experienced edge failure. Regarding Examples O1-O58, of the 58 mobile phone samples, 8 mobile phone samples experienced edge failure, reducing the total number of mobile phone samples to 50 and the number of those samples that experienced no fracture on the major surface of the glass substrate or layered-substrate (including a glass substrate, layer and, optionally, additional layer(s)) was 44. Accordingly, the survival % (44/50) of Examples O1-O58 was 88%. Where the "survival % including samples that experienced edge failure" is the same as the "survival % excluding samples that experienced edge failure", none of the failures were edge failures.

TABLE 7

Substrate and Coating attributes for Example 6.

| Samples | CS | DOL | Spike | Layer/Additional Layer(s) Composition | Layer/Additional Layer(s) Thickness |
|---|---|---|---|---|---|
| L1-L10 | Unknown | Unknown | Unknown | Unknown | Unknown |
| M1-M33 | 900 MPa | 40-45 μm | None | None | N/A |
| N1-N15 | 900 MPa | 40-45 μm | None | $Si_3N_4$ Single Layer | 100 nm |
| O1-O15 | 900 MPa | 40-45 μm | None | AlOxNy single layer | 2 μm |
| O16-O30 | 375 MPa | 100 μm | None | AlOxNy layer single layer | 2 μm |
| O31-O39 | 375 MPa | 75 μm | Yes | AlOxNy layer, $Al_2O_3$ first additional layer and $SiO_2$ second additional layer | AlOxNy: 2 μm $Al_2O_3$: 88.7 nm $SiO_2$: 33 nm |
| O40-O48 | 375 MPa | 125 μm | Yes | AlOxNy layer, $Al_2O_3$ first additional layer and $SiO_2$ second additional layer | AlOxNy: 2 μm $Al_2O_3$: 88.7 nm $SiO_2$: 33 nm |
| O49-O58 | 900 MPa | 40-45 μm | None | AlOxNy layer, $Al_2O_3$ first additional layer and $SiO_2$ second additional layer | AlOxNy: 2 μm $Al_2O_3$: 88.6 nm $SiO_2$: 33 nm |
| P1-27 | 375 MPa | 100 μm | None | None | N/A |

TABLE 8

Results from Drop Test of Examples L, M, N, O and P.

| Samples | Total No. of Samples Tested | Survival % (including samples that experienced edge failure) | Survival % (excluding samples that experienced edge failure) |
|---|---|---|---|
| L1-L10 | 10 | 50% | 50% |
| M1-M33 | 33 | 59% | 59% |
| N1-N15 | 15 | 73% | 100% |
| O1-O15 | 15 | 73% | 100% |
| O16-O30 | 15 | 73% | 100% |
| O31-O39 | 9 | 67% | 75% |
| O40-O48 | 9 | 78% | 100% |
| O49-O58 | 10 | 90% | 90% |
| P1-27 | 27 | 86% | 86% |

Figure 12:
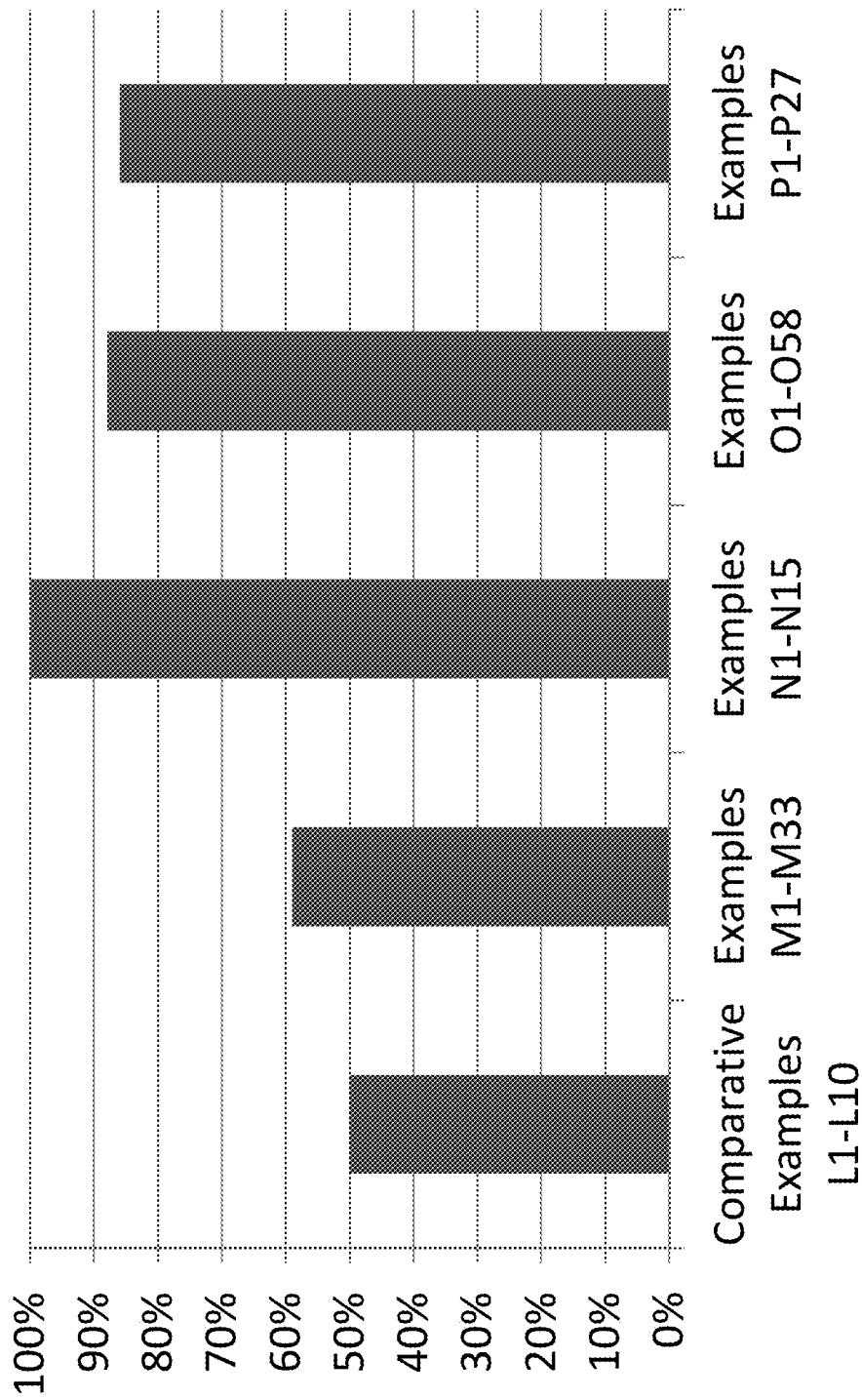
FIG. 12 illustrates the survival % of mobile phone samples according to Example 6.

FIG. 12 graphically illustrates the survival % (excluding edge failures) of Examples L, M, N, O and P.

Figure 13:
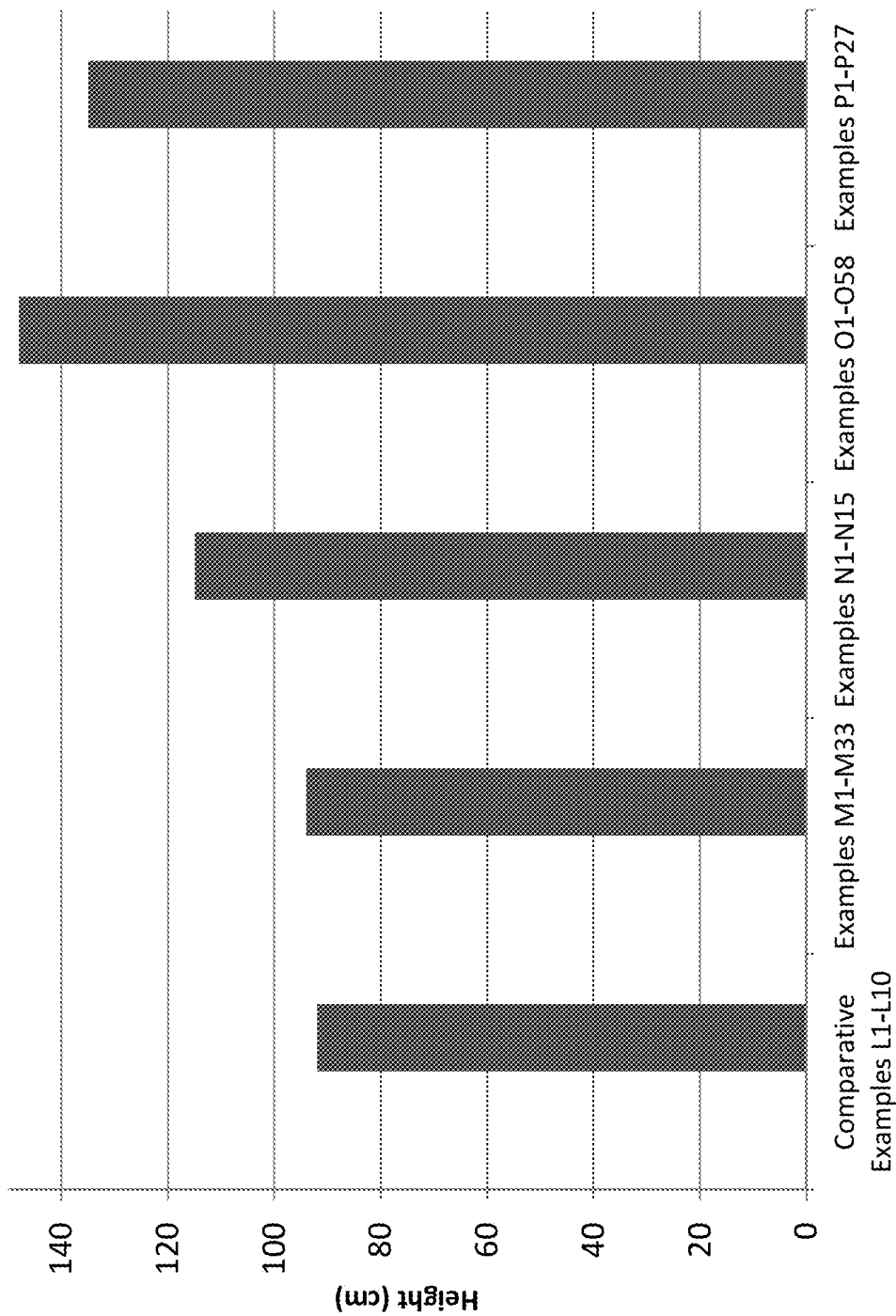
FIG. 13 illustrates the height to failure of some of the mobile phone samples of Example 6.

The mobile phone samples that survived the drop test at 1 m onto an asphalt surface were then dropped from increasing heights, starting at 30 cm, onto an asphalt surface. These mobile phone samples were dropped so that the layered-substrate (including a glass substrate, layer and, optionally, additional layer(s)) or glass substrate contacts the asphalt surface first and directly. The drop height was increased by 10 cm increments for each surviving mobile phone sample. The average height to failure of samples tested are provided below in Table 9 and graphically illustrated in FIG. 13.

| Samples | Height (cm) |
|---|---|
| Comparative Examples L1-L10 | 92 |
| Examples M1-M33 | 94 |
| Examples N1-N15 | 115 |
| Examples O1-O58 | 148 |
| Examples P1-P27 | 135 |

Figure 14:
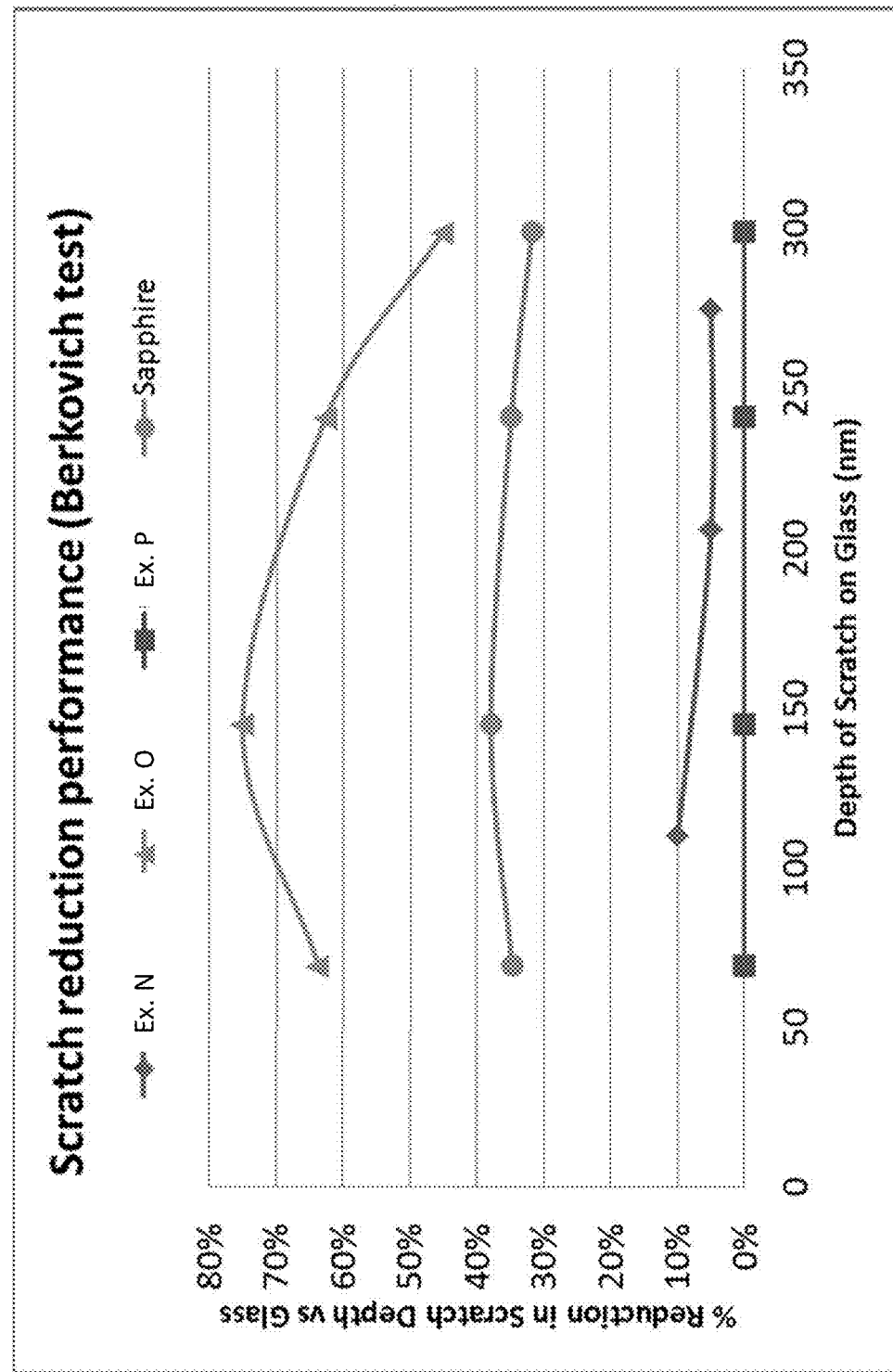
FIG. 14 shows the scratch depth reductions of Examples N, O and P and a bare crystalline substrate, as compared to a bare glass substrate.

The scratch resistance of Examples N, O and P and a bare crystalline substrate was compared to a bare glass substrate. At least one layered-substrate (including a glass substrate, layer and, optionally, additional layer(s)) used in Examples N and O, at least one glass substrate used in Example P, at least one bare sapphire substrate and at least one bare glass substrate were scratched using a Berkovich indenter using identical procedures. The depths of the resulting scratches in each of the layered-substrates (including a glass substrate, layer and, optionally, additional layer(s)), sapphire substrate and glass substrates were compared. The depths of the scratches were measured by atomic force microscopy (AFM), using known methods in the art. In FIG. 14, the reduction in scratch depth of Examples N, O and P were compared to bare glass substrate. In addition, the reduction in scratch depth of a sapphire substrate was compared to the same glass substrate. As shown in FIG. 14, the sapphire substrate exhibited a 35-38% reduction in scratch depth as compared to a bare glass substrate. Example N exhibited a reduction in scratch depth in the range from about 5% to about 10%. Example O exhibited a reduction in scratch depth in the range from about 45% to about 75%. Example P, which is also a bare glass substrate, did not exhibit any reduction in scratch depth when compared to the comparative bare glass substrate.

Figure 15B:
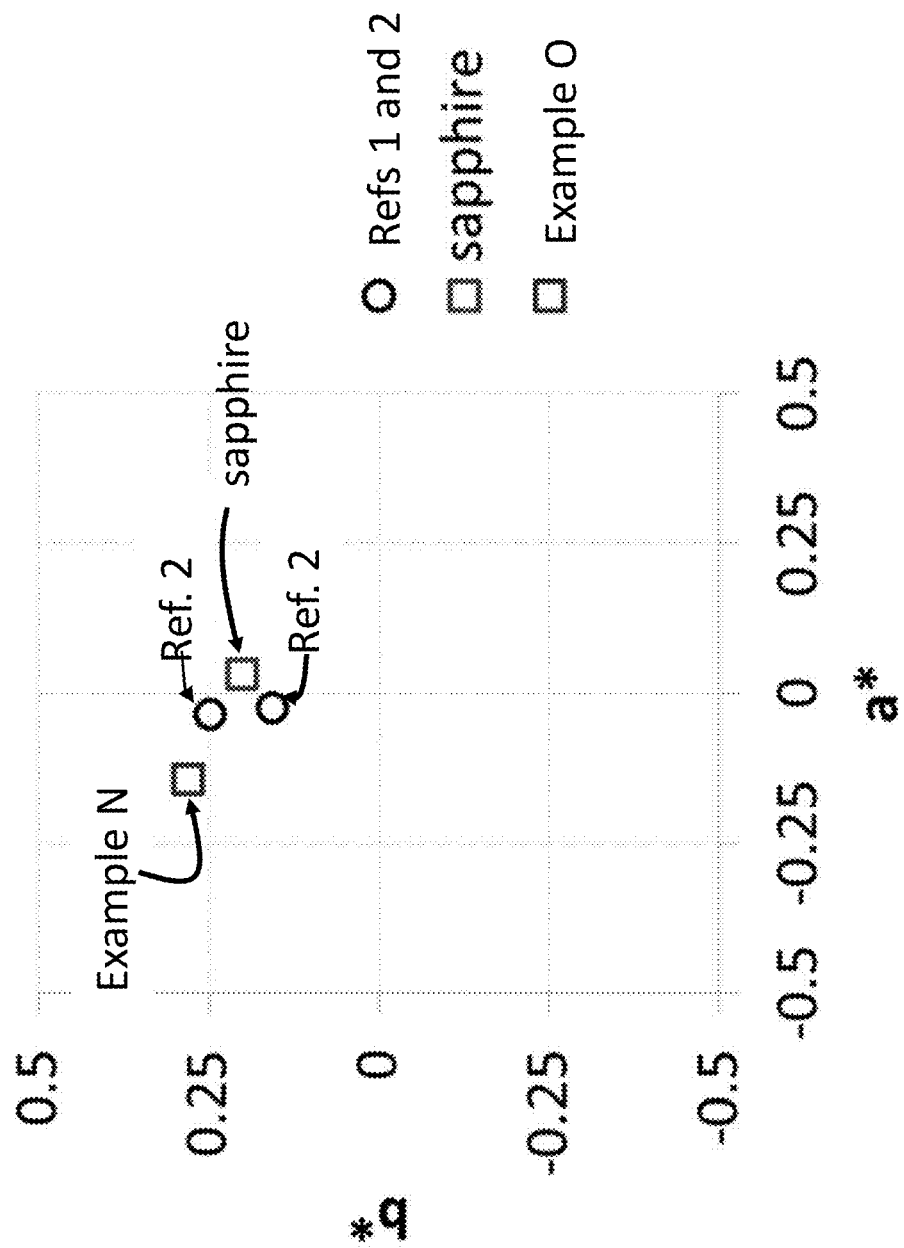
FIG. 15B is a plot of the transmittance color coordinates a* and b* in the L*a*b* color space of select substrates and Example 0, according to Example 6.
Figure 15C:
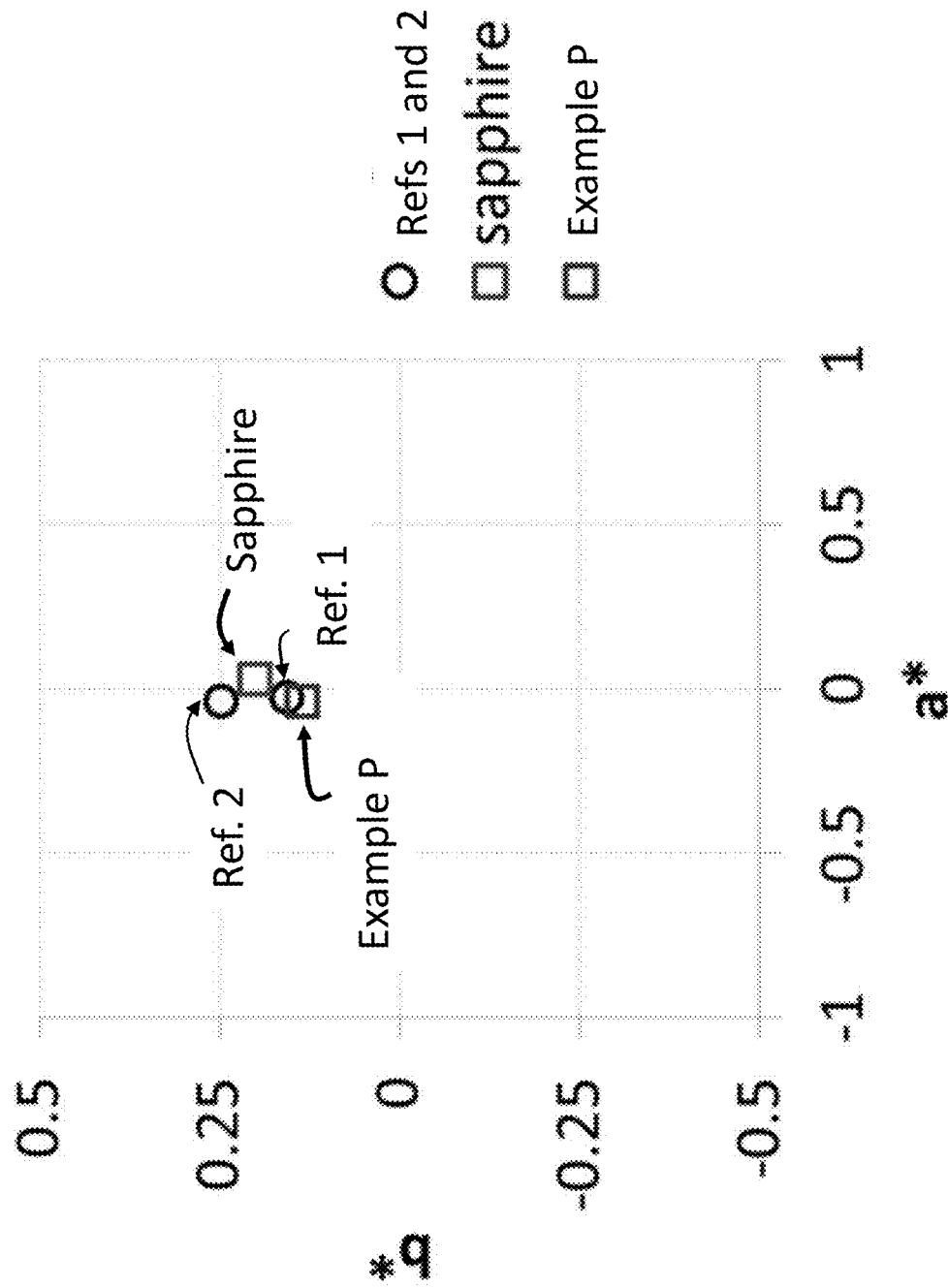
FIG. 15C is a plot of the transmittance color coordinates a* and b* in the L*a*b* color space of select substrates and Example P, according to Example 6.

The color in transmittance of the layered-substrates (including a glass substrate, layer and, optionally, additional layer(s)) used in Examples N and O, the glass substrate used in Example P and a sapphire substrate were compared to the color in transmittance of a first glass substrate (Reference 1) and a second glass substrate (Reference 2). The first glass substrate had a nominal composition of about 65 mol % $SiO_2$, about 14 mol % $Al_2O_3$; about 5 mol % $B_2O_3$; about 14 mol % $Na_2O$; and about 2.5 mol % MgO. The first glass substrate was also strengthened to exhibit a CS of at least about 700 MPa and a DOL of at least about 40 μm. The second glass substrate (Reference 2) had a nominal composition of about 65 mol. % $SiO_2$; about 14 mol. % $Al_2O_3$; about 7 mol. % $B_2O_3$; about 14 mol. % $Na_2O$; and about 0.5 mol. % $K_2O$. The color in transmittance of the layered-substrates (including a glass substrate, layer and, optionally, additional layer(s)) of Examples N and O, the glass substrate used in Example P, the sapphire substrate, the first glass substrate and the second glass was presented in CIELAB color space coordinates in transmittance, determined from specular reflectance measurements using a spectrophotometer, with illuminant D65, as illustrated in FIGS. 15A, 15B and 15C.

It will be apparent to those skilled in the art that various modifications and variations can be made without departing from the spirit or scope of the invention.

What is claimed is:

1. A layered-substrate comprising:
    a substrate comprising an outwardly-facing surface;
    a layer disposed on the outwardly-facing surface, wherein the layered-substrate exhibits a hardness of at least about 12 GPa, as measured by the Berkovich Indenter Hardness Test, along an indentation depth of about 100 nm or greater and wherein the layered-substrate is able to withstand fracture when assembled in a device and the device is dropped from a height of at least 100 cm onto a drop surface, wherein the layer comprises 55 or more % by weight of a metal oxynitride, and;
    an additional layer comprising metal oxide, wherein the additional layer is disposed directly on the layer so that the layer is disposed between the substrate and the additional layer.

2. The layered-substrate of claim 1, wherein the outwardly facing surface comprises at least one of opposing major surfaces, and the substrate exhibits an average strain-to-failure at a surface of one or more of the opposing major surfaces that is 0.5% or greater.

3. The layered-substrate of claim 1, wherein the substrate is chemically strengthened and comprises a compressive stress (CS) layer with a CS of at least 250 MPa extending to a depth of layer (DOL) of at least 10 μm.

4. The layered-substrate of claim 1, wherein the layer exhibits a hardness of at least about 20 GPa, as measured by a Berkovich Indenter Hardness Test, along an indentation depth of about 100 nm or greater, and has a thickness of at least about 500 nm.

5. The layered-substrate of claim 1, wherein the layered-substrate exhibits a transmittance of at least about 85%, or of less than about 10%, over the visible spectrum.

6. The layered-substrate of claim 1, wherein the layer has a first index of refraction, the additional layer has a second index of refraction, and further wherein the first index of refraction is higher than the second index of refraction.

7. The layered-substrate of claim 1, further comprising a second additional layer comprising metal oxide, wherein the second additional layer is disposed directly on the substrate so that the second additional layer is disposed between the layer and the substrate.

8. The layered-substrate of claim 7, wherein the metal oxynitride comprises silicon oxynitride, and the metal oxide comprises silicon oxide.

9. A fracture-resistant article comprising:

a substrate comprising opposing major surfaces;

a layer disposed on a first opposing major surface of the substrate, wherein the article exhibits a hardness of at least about 10 GPa as measured by a Berkovich Indenter Hardness Test along an indentation depth of about 100 nm or greater, and is able to withstand fracture when assembled with a device that is dropped in a drop test from a height of at least 100 cm onto a drop surface, wherein the layer comprises 55 or more % by weight of a metal oxynitride, and;

an additional layer comprising metal oxide, wherein the additional layer is disposed directly on the layer so that the layer is disposed between the substrate and the additional layer.

10. The fracture-resistant article of claim 9, wherein the drop surface comprises asphalt or 180 grit sandpaper.

11. The fracture-resistant article of claim 9, wherein the substrate exhibits an average strain-to-failure at a surface of one or more of the opposing major surfaces that is 0.5% or greater.

12. The fracture-resistant article of claim 9, wherein the substrate is chemically strengthened and comprises a compressive stress (CS) layer with a CS of at least 250 MPa extending to a depth of layer (DOL) of at least 10 μm.

13. The fracture-resistant article of claim 9, wherein the metal of the metal oxynitride is selected from the group consisting of B, Al Si, Ti, V, Cr, Y, Zr, Nb, Mo, Sn, Hf, Ta and W.

14. The fracture-resistant article of claim 9, further exhibiting resistance to flaw penetration of one or more flaws from the layer, wherein the one or more flaws from the layer comprise at least one of:

flaws that are introduced into the layer by contact between the layered-substrate and the drop surface; and flaws that are present in the layer prior to being dropped.

15. The fracture-resistant article of claim 14, wherein the layer substantially prevents the introduction of new flaws into the substrate.

16. The layered-substrate of claim 9, wherein the layer has a first index of refraction, the additional layer has a second index of refraction, and further wherein the first index of refraction is higher than the second index of refraction.

17. The layered-substrate of claim 9, further comprising a second additional layer comprising metal oxide, wherein the second additional layer is disposed directly on the substrate so that the second additional layer is disposed between the layer and the substrate.

18. The layered-substrate of claim 17, wherein the metal oxynitride comprises silicon oxynitride, and the metal oxide comprises silicon oxide.

19. A portable device comprising:

a substrate having a major surface providing a user interface and having an initial scratch resistance and an initial impact resistance;

a layer on the major surface forming a layered-substrate exhibiting an enhanced scratch resistance and enhanced impact resistance, wherein the enhanced impact resistance comprises an average flexural strength after abrading the layered-substrate that is at least 80% of an average flexural strength before abrading the layered-substrate, and wherein said enhanced scratch resistance comprises a hardness of at least about 10 GPa, as measured by a Berkovich Indenter Hardness Test, along an indentation depth of about 100 nm or greater, wherein the layer comprises 55 or more % by weight of a metal oxynitride, and;

an additional layer comprising metal oxide, wherein the additional layer is disposed directly on the layer so that the layer is disposed between the substrate and the additional layer.

20. A device comprising:

a substrate comprising opposing major surfaces;

a layer disposed on a first opposing major surface of the substrate to form a layered-substrate, wherein the layered-substrate is able to withstand fracture when the device is dropped from a height of at least 100 cm onto a drop surface, wherein the layer comprises 55 or more by weight of a metal oxynitride, and;

an additional layer comprising metal oxide, wherein the additional layer is disposed directly on the layer so that the layer is disposed between the substrate and the additional layer.

* * * * *

UNITED STATES PATENT AND TRADEMARK OFFICE
CERTIFICATE OF CORRECTION

Page 1 of 1

PATENT NO. : 10,160,688 B2
APPLICATION NO. : 14/482250
DATED : December 25, 2018
INVENTOR(S) : Jaymin Amin et al.

It is certified that error appears in the above-identified patent and that said Letters Patent is hereby corrected as shown below:

On the Title Page

On page 3, Column 1, item (56), other publications, Line 17, delete "Incluence" and insert -- Influence --, therefor.

On page 3, Column 1, item (56), other publications, Line 37, delete "Interconects" and insert -- Interconnects --, therefor.

On page 3, Column 1, item (56), other publications, Line 59, delete "Characatization" and insert -- Characterization --, therefor.

On page 3, Column 1, item (56), other publications, Line 61, delete "Physices" and insert -- Physics --, therefor.

On page 3, Column 2, item (56), other publications, Line 8, delete "Sceince" and insert -- Science --, therefor.

On page 3, Column 2, item (56), other publications, Line 33, delete "Internat onal" and insert -- International --, therefor.

On page 3, Column 2, item (56), other publications, Line 40, delete "Fomiation" and insert -- Formation --, therefor.

In the Claims

In Column 41, Line 28, Claim 13, delete "Al Si," and insert -- Al, Si, --, therefor.

In Column 42, Line 37, Claim 20, after "more" insert -- % --.

Signed and Sealed this
Thirty-first Day of March, 2020

Andrei Iancu
*Director of the United States Patent and Trademark Office*